US011155845B2

(12) United States Patent
Tabata et al.

(10) Patent No.: US 11,155,845 B2
(45) Date of Patent: Oct. 26, 2021

(54) METHOD FOR PRODUCING THEANINE

(71) Applicant: KYOWA HAKKO BIO CO., LTD., Tokyo (JP)

(72) Inventors: Kazuhiko Tabata, Tokyo (JP); Shoto Ohno, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 0 days.

(21) Appl. No.: 16/603,827

(22) PCT Filed: Apr. 12, 2018

(86) PCT No.: PCT/JP2018/015372
§ 371 (c)(1),
(2) Date: Oct. 8, 2019

(87) PCT Pub. No.: WO2018/190398
PCT Pub. Date: Oct. 18, 2018

(65) Prior Publication Data
US 2020/0131546 A1  Apr. 30, 2020

(30) Foreign Application Priority Data

Apr. 13, 2017 (JP) .............................. JP2017-079893

(51) Int. Cl.
*C12P 13/00* (2006.01)
*C12N 9/10* (2006.01)
*C12N 9/00* (2006.01)
*C12N 1/21* (2006.01)
*C12P 13/04* (2006.01)
*C12N 1/20* (2006.01)

(52) U.S. Cl.
CPC ............... *C12P 13/04* (2013.01); *C12N 1/20* (2013.01); *C12Y 305/01002* (2013.01)

(58) Field of Classification Search
None
See application file for complete search history.

(56) References Cited

U.S. PATENT DOCUMENTS

| 8,211,674 B2 | 7/2012 | Okada et al. | |
| 2010/0192985 A1* | 8/2010 | Aehle | C11D 3/38645 134/26 |
| 2014/0120587 A1* | 5/2014 | Haas | C12P 17/04 435/122 |

FOREIGN PATENT DOCUMENTS

| JP | H05-068578 A | 3/1993 |
| JP | H08-089266 A | 4/1996 |
| JP | H11-225789 A | 8/1999 |
| JP | 2007-185132 A | 7/2007 |
| JP | 2009-225705 A | 10/2009 |
| WO | WO 2005/118719 A1 | 12/2005 |
| WO | WO 2006/001296 A1 | 1/2006 |

OTHER PUBLICATIONS

Liu et al., Process Biochem. 51:1458-1463, 2016 (Year: 2016).*
Zhou et al., Cell Mol Life Sci 63:2260-2290, 2006 (Year: 2006).*
Kozak, M., Gene 234:187-208, 1999 (Year: 1999).*
Zhang et al., Structure 26:1474-1485, 2018 (Year: 2018).*
Clark et al., J. Bacteriol. 144:179-184, 1980 (Year: 1980).*
Kim et al., J. Bacteriol. 192:5304-5311,2010 (Year: 2010).*
De Azevedo Wäsch et al., "Transformation of Isopropylamine to $_L$-Alaninol by *Pseudomonas* sp. Strain KIE171 Involves N-Glutamylated Intermediates," *Appl. Environ. Microbiol.*, 68(5): 2368-2375 (2002).
Genbank Database, "Aminotransferase [Pseudomonas chlororaphis subsp. aurantiaca]," Accession No. AI510430.1 (2014) [obtained at: https://www.ncbi.nlm.nih.gov/protein/692336513].
Genbank Database, "Omega-Amino Acid—Pyruvate Aminotransferase [Pseudomonas fluorescens SBW25]," Accession No. CAY46943.1 (2015) [obtained at: https://www.ncbi.nlm.nih.gov/protein/229360089].
Genbank Database, "Polyamine: pyruvate transaminase [Pseudomonas putida KT2440]," Accession No. NP_747283.1 (2016) [obtained at: https://www.ncbi.nlm.nih.gov/protein/NP_747283.1].
Gruffaz et al., "Genes of the N-Methylglutamate Pathway Are Essential for Growth of *Methylobacterium extorquens* DM4 with Monomethylamine," *Appl. Environ. Mircrobiol.*, 80(11): 3541-3550 (2014).
Klatte et al., "Role of L-alanine for redox self-sufficient amination of alcohols," *Microb. Cell Fact.*, 14: 9 (2015).
Rodriguez et al., "Isobutyraldehyde production from *Escherichia coli* by removing aldehyde reductase activity," *Microb. Cell Fact.*, 11: 90 (2012).
Seo et al., "Computational Selection, Identification and Structural Analysis of ω-Aminotransferases with Various Substrate Specificities from the Genome Sequence of Mesorhizobium Loti MAFF303099," *Biosci. Biotechnol. Biochem.*, 76(7): 1308-1314 (2012).
Tachiki, "Studies on Biosynthetic Systems of Glutamine and Glutamic Acid in Bacteria and Their Application in a New Fermentation Process," *Japan Society for Bioscience, Biotechnology, and Argochemistry*, 57(11): 1155-1164 (1983).
Zhu et al., "Coproduction of Acetaldehyde and Hydrogen during Glucose Fermentation by *Escherichia coli*," *Appl. Environ. Microbiol.*, 77(18): 6441-6450 (2011).
Japanese Patent Office, International Search Report in International Patent Application No. PCT/JP2018/015372 (dated Jun. 26, 2018).
Japanese Patent Office, International Preliminary Report on Patentability in International Patent Application No. PCT/JP2018/015372 (dated Oct. 15, 2019).

* cited by examiner

*Primary Examiner* — David Steadman
(74) *Attorney, Agent, or Firm* — Leydig, Voit & Mayer, Ltd.

(57) ABSTRACT

According to the present invention, theanine can efficiently be produced without exogenously adding ethylamine and without accumulation or leftover of ethylamine as a byproduct, by using a microorganism having enhanced activity to produce ethylamine with acetaldehyde and alanine as substrates and having enhanced activity of γ-glutamylmethylamide synthetase or glutaminase.

10 Claims, 2 Drawing Sheets

Specification includes a Sequence Listing.

SEQUENCE LISTING

```
<160> NUMBER OF SEQ ID NOS: 50

<210> SEQ ID NO 1
<211> LENGTH: 1362
<212> TYPE: DNA
<213> ORGANISM: Pseudomonas putida
<220> FEATURE:
<221> NAME/KEY: CDS
<222> LOCATION: (1)..(1359)

<400> SEQUENCE: 1 atg agc gtc aac aac ccg caa acc cgt gaa tgg caa acc ctg agc ggg      48
Met Ser Val Asn Asn Pro Gln Thr Arg Glu Trp Gln Thr Leu Ser Gly
1               5                   10                  15 gag cat cac ctc gca cct ttc agt gac tac aag cag ctg aag gag aag      96
Glu His His Leu Ala Pro Phe Ser Asp Tyr Lys Gln Leu Lys Glu Lys
```

```
                       20                  25                  30
ggg ccg cgc atc atc acc aag gcc cag ggt gtg cat ttg tgg gat agc    144
Gly Pro Arg Ile Ile Thr Lys Ala Gln Gly Val His Leu Trp Asp Ser
             35                  40                  45 gag ggg cac aag atc ctc gac ggc atg gcc ggt cta tgg tgc gtg gcg    192
Glu Gly His Lys Ile Leu Asp Gly Met Ala Gly Leu Trp Cys Val Ala
 50                  55                  60 gtc ggc tac gga cgt gaa gag ctg gtg cag gcg gcg gaa aaa cag atg    240
Val Gly Tyr Gly Arg Glu Glu Leu Val Gln Ala Ala Glu Lys Gln Met
 65                  70                  75                  80 cgc gag ctg ccg tac tac aac ctg ttc ttc cag acc gct cac ccg cct    288
Arg Glu Leu Pro Tyr Tyr Asn Leu Phe Phe Gln Thr Ala His Pro Pro
                 85                  90                  95 gcg ctc gag ctg gcc aag gcg atc acc gac gtg gcg ccg aaa ggt atg    336
Ala Leu Glu Leu Ala Lys Ala Ile Thr Asp Val Ala Pro Lys Gly Met
            100                 105                 110 acc cat gtg ttc ttc acc ggc tcc ggc tcc gaa ggc aac gac act gtg    384
Thr His Val Phe Phe Thr Gly Ser Gly Ser Glu Gly Asn Asp Thr Val
                115                 120                 125 ctg cgc atg gtg cgt cac tac tgg gcg ctg aag ggc aaa ccg cac aag    432
Leu Arg Met Val Arg His Tyr Trp Ala Leu Lys Gly Lys Pro His Lys
            130                 135                 140 cag acc atc atc ggc cgc atc aac ggt tac cac ggc tcc acc ttc gcc    480
Gln Thr Ile Ile Gly Arg Ile Asn Gly Tyr His Gly Ser Thr Phe Ala
145                 150                 155                 160 ggt gca tgc ctg ggc ggt atg agc ggc atg cac gag cag ggt ggc ctg    528
Gly Ala Cys Leu Gly Gly Met Ser Gly Met His Glu Gln Gly Gly Leu
                165                 170                 175 ccg atc ccg ggc atc gtg cac atc cct cag ccg tac tgg ttc ggc gag    576
Pro Ile Pro Gly Ile Val His Ile Pro Gln Pro Tyr Trp Phe Gly Glu
            180                 185                 190 gga ggc gac atg acc cct gac gaa ttc ggt gtc tgg gcc gcc gag cag    624
Gly Gly Asp Met Thr Pro Asp Glu Phe Gly Val Trp Ala Ala Glu Gln
                195                 200                 205 ttg gag aag aag atc ctc gaa gtc ggc gaa gac aac gtc gcg gcc ttc    672
Leu Glu Lys Lys Ile Leu Glu Val Gly Glu Asp Asn Val Ala Ala Phe
            210                 215                 220 atc gcc gag ccg atc cag ggc gct ggt ggc gtg atc atc ccg ccg gaa    720
Ile Ala Glu Pro Ile Gln Gly Ala Gly Gly Val Ile Ile Pro Pro Glu
225                 230                 235                 240 acc tac tgg ccg aag gtg aag gag atc ctc gcc agg tac gac atc ctg    768
Thr Tyr Trp Pro Lys Val Lys Glu Ile Leu Ala Arg Tyr Asp Ile Leu
                245                 250                 255 ttc gtc gcc gac gag gtg atc tgc ggc ttc ggc cgt acc ggc gag tgg    816
Phe Val Ala Asp Glu Val Ile Cys Gly Phe Gly Arg Thr Gly Glu Trp
            260                 265                 270 ttc ggc tcg gac tac tac gac ctc aag ccc gac ctg atg acc atc gcg    864
Phe Gly Ser Asp Tyr Tyr Asp Leu Lys Pro Asp Leu Met Thr Ile Ala
                275                 280                 285 aaa ggc ctg acc tcc ggt tac atc ccc atg ggc ggt gtg atc gtg cgt    912
Lys Gly Leu Thr Ser Gly Tyr Ile Pro Met Gly Gly Val Ile Val Arg
            290                 295                 300 gac acc gtg gcc aag gtg atc agc gaa ggc ggc gac ttc aac cac ggt    960
Asp Thr Val Ala Lys Val Ile Ser Glu Gly Gly Asp Phe Asn His Gly
305                 310                 315                 320 ttc acc tac tcc ggc cac ccg gtg gcg gcc gcg gtg ggc ctg gaa aac   1008
Phe Thr Tyr Ser Gly His Pro Val Ala Ala Ala Val Gly Leu Glu Asn
                325                 330                 335 ctg cgc att ctg cgt gac gag aaa att gtc gag aag gcg cgc acg gaa   1056
```

```
Leu Arg Ile Leu Arg Asp Glu Lys Ile Val Glu Lys Ala Arg Thr Glu
                340                 345                 350 gcg gca ccg tat ttg caa aag cgt ttg cgc gag ctg caa gac cat cca    1104
Ala Ala Pro Tyr Leu Gln Lys Arg Leu Arg Glu Leu Gln Asp His Pro
        355                 360                 365 ctg gtg ggt gaa gtg cgc ggc ctg ggc atg ctg gga gcg atc gag ctg    1152
Leu Val Gly Glu Val Arg Gly Leu Gly Met Leu Gly Ala Ile Glu Leu
370                 375                 380 gtc aag gac aag gca acc cgc agc cgt tac gag ggc aag ggc gtt ggc    1200
Val Lys Asp Lys Ala Thr Arg Ser Arg Tyr Glu Gly Lys Gly Val Gly
385                 390                 395                 400 atg atc tgt cgc acc ttc tgc ttc gag aac ggc ctg atc atg cgt gcg    1248
Met Ile Cys Arg Thr Phe Cys Phe Glu Asn Gly Leu Ile Met Arg Ala
                405                 410                 415 gtg ggt gac acc atg atc atc gcg ccg ccg ctg gta atc agc cat gcg    1296
Val Gly Asp Thr Met Ile Ile Ala Pro Pro Leu Val Ile Ser His Ala
                420                 425                 430 gag atc gac gaa ctg gtg gaa aag gcg cgc aag tgc ctg gac ctg acc    1344
Glu Ile Asp Glu Leu Val Glu Lys Ala Arg Lys Cys Leu Asp Leu Thr
                435                 440                 445 ctt gag gcg att caa taa                                            1362
Leu Glu Ala Ile Gln
        450

<210> SEQ ID NO 2
<211> LENGTH: 453
<212> TYPE: PRT
<213> ORGANISM: Pseudomonas putida

<400> SEQUENCE: 2

Met Ser Val Asn Asn Pro Gln Thr Arg Glu Trp Gln Thr Leu Ser Gly
1               5                   10                  15

Glu His Leu Ala Pro Phe Ser Asp Tyr Lys Gln Leu Lys Glu Lys
            20                  25                  30

Gly Pro Arg Ile Ile Thr Lys Ala Gln Gly Val His Leu Trp Asp Ser
        35                  40                  45

Glu Gly His Lys Ile Leu Asp Gly Met Ala Gly Leu Trp Cys Val Ala
    50                  55                  60

Val Gly Tyr Gly Arg Glu Glu Leu Val Gln Ala Ala Glu Lys Gln Met
65                  70                  75                  80

Arg Glu Leu Pro Tyr Tyr Asn Leu Phe Phe Gln Thr Ala His Pro Pro
                85                  90                  95

Ala Leu Glu Leu Ala Lys Ala Ile Thr Asp Val Ala Pro Lys Gly Met
            100                 105                 110

Thr His Val Phe Phe Thr Gly Ser Gly Ser Glu Gly Asn Asp Thr Val
        115                 120                 125

Leu Arg Met Val Arg His Tyr Trp Ala Leu Lys Gly Lys Pro His Lys
    130                 135                 140

Gln Thr Ile Ile Gly Arg Ile Asn Gly Tyr His Gly Ser Thr Phe Ala
145                 150                 155                 160

Gly Ala Cys Leu Gly Gly Met Ser Gly Met His Glu Gln Gly Gly Leu
                165                 170                 175

Pro Ile Pro Gly Ile Val His Ile Pro Gln Pro Tyr Trp Phe Gly Glu
            180                 185                 190

Gly Gly Asp Met Thr Pro Asp Glu Phe Gly Val Trp Ala Ala Glu Gln
        195                 200                 205

Leu Glu Lys Lys Ile Leu Glu Val Gly Glu Asp Asn Val Ala Ala Phe
```

```
            210                 215                 220
Ile Ala Glu Pro Ile Gln Gly Ala Gly Gly Val Ile Pro Pro Glu
225                 230                 235                 240

Thr Tyr Trp Pro Lys Val Lys Glu Ile Leu Ala Arg Tyr Asp Ile Leu
                245                 250                 255

Phe Val Ala Asp Glu Val Ile Cys Gly Phe Gly Arg Thr Gly Glu Trp
                260                 265                 270

Phe Gly Ser Asp Tyr Tyr Asp Leu Lys Pro Asp Leu Met Thr Ile Ala
            275                 280                 285

Lys Gly Leu Thr Ser Gly Tyr Ile Pro Met Gly Gly Val Ile Val Arg
        290                 295                 300

Asp Thr Val Ala Lys Val Ile Ser Glu Gly Gly Asp Phe Asn His Gly
305                 310                 315                 320

Phe Thr Tyr Ser Gly His Pro Val Ala Ala Val Gly Leu Glu Asn
                325                 330                 335

Leu Arg Ile Leu Arg Asp Glu Lys Ile Val Glu Lys Ala Arg Thr Glu
                340                 345                 350

Ala Ala Pro Tyr Leu Gln Lys Arg Leu Arg Glu Leu Gln Asp His Pro
            355                 360                 365

Leu Val Gly Glu Val Arg Gly Leu Gly Met Leu Gly Ala Ile Glu Leu
        370                 375                 380

Val Lys Asp Lys Ala Thr Arg Ser Arg Tyr Glu Gly Lys Gly Val Gly
385                 390                 395                 400

Met Ile Cys Arg Thr Phe Cys Phe Glu Asn Gly Leu Ile Met Arg Ala
                405                 410                 415

Val Gly Asp Thr Met Ile Ile Ala Pro Pro Leu Val Ile Ser His Ala
            420                 425                 430

Glu Ile Asp Glu Leu Val Glu Lys Ala Arg Lys Cys Leu Asp Leu Thr
        435                 440                 445

Leu Glu Ala Ile Gln
    450

<210> SEQ ID NO 3
<211> LENGTH: 1347
<212> TYPE: DNA
<213> ORGANISM: Pseudomonas putida
<220> FEATURE:
<221> NAME/KEY: CDS
<222> LOCATION: (1)..(1344)

<400> SEQUENCE: 3 atg aac atg ccc gaa act ggt cct gcc ggt atc gcc agc cag ctc aag    48
Met Asn Met Pro Glu Thr Gly Pro Ala Gly Ile Ala Ser Gln Leu Lys
1               5                   10                  15 ctg gac gcc cac tgg atg ccc tac acc gcc aac cgc aac ttc cag cgc    96
Leu Asp Ala His Trp Met Pro Tyr Thr Ala Asn Arg Asn Phe Gln Arg
            20                  25                  30 gac cca cgc ctg atc gtg gcg gcc gaa ggc aac tac ctg gtc gat gac   144
Asp Pro Arg Leu Ile Val Ala Ala Glu Gly Asn Tyr Leu Val Asp Asp
        35                  40                  45 cac ggg cgc aag atc ttc gac gcc ctg tcc ggc ctg tgg acc tgc ggc   192
His Gly Arg Lys Ile Phe Asp Ala Leu Ser Gly Leu Trp Thr Cys Gly
    50                  55                  60 gca ggg cac act cgc aag gaa atc gct gac gcg gtg acc cgt caa ctg   240
Ala Gly His Thr Arg Lys Glu Ile Ala Asp Ala Val Thr Arg Gln Leu
65                  70                  75                  80 agt acg ctg gac tac tcc cca gcg ttc cag ttc ggc cac ccg ctg tcg   288
```

|   |   |   |   |   |   |   |   |   |   |   |   |   |   |   |   |   |
|---|---|---|---|---|---|---|---|---|---|---|---|---|---|---|---|---|
| Ser | Thr | Leu | Asp | Tyr | Ser | Pro | Ala | Phe | Gln | Phe | Gly | His | Pro | Leu | Ser | |
|     |     |     |     | 85  |     |     |     | 90  |     |     |     |     | 95  |     |     | |

```
ttc cag ctg gcg gaa aag atc gcc gag ctg gtt ccg ggc aat ctg aat       336
Phe Gln Leu Ala Glu Lys Ile Ala Glu Leu Val Pro Gly Asn Leu Asn
            100                 105                 110 cac gtc ttc tat acc aac tcc ggt tcc gag tgc gcc gat acc gca ctg       384
His Val Phe Tyr Thr Asn Ser Gly Ser Glu Cys Ala Asp Thr Ala Leu
            115                 120                 125 aag atg gtg cgt gcc tac tgg cgc ctg aaa ggc cag gca acc aag acc       432
Lys Met Val Arg Ala Tyr Trp Arg Leu Lys Gly Gln Ala Thr Lys Thr
130                 135                 140 aag atc atc ggc cgt gcc cgt ggt tac cat ggc gtg aac atc gcc ggt       480
Lys Ile Ile Gly Arg Ala Arg Gly Tyr His Gly Val Asn Ile Ala Gly
145                 150                 155                 160 acc agc ctg ggt ggc gtc aac ggt aac cgc aag atg ttt ggc cag ctg       528
Thr Ser Leu Gly Gly Val Asn Gly Asn Arg Lys Met Phe Gly Gln Leu
            165                 170                 175 ctg gac gtc gac cac ctg cct cac act gta ttg ccg gtg aac gcc ttc       576
Leu Asp Val Asp His Leu Pro His Thr Val Leu Pro Val Asn Ala Phe
            180                 185                 190 tcg aaa ggc ttg ccg gaa gag ggc ggt atc gcg ctg gct gac gaa atg       624
Ser Lys Gly Leu Pro Glu Glu Gly Gly Ile Ala Leu Ala Asp Glu Met
            195                 200                 205 ctc aag ctg atc gag ctg cac gat gcc tcc aac atc gca gca gtc atc       672
Leu Lys Leu Ile Glu Leu His Asp Ala Ser Asn Ile Ala Ala Val Ile
210                 215                 220 gtc gag ccg ctg gcc ggt tcg gcc ggt gtg ctg ccg ccg cca aag ggt       720
Val Glu Pro Leu Ala Gly Ser Ala Gly Val Leu Pro Pro Pro Lys Gly
225                 230                 235                 240 tac ctg aag cgc ctg cgt gaa atc tgc acc cag cac aac att ctg ctg       768
Tyr Leu Lys Arg Leu Arg Glu Ile Cys Thr Gln His Asn Ile Leu Leu
            245                 250                 255 atc ttc gac gaa gtg atc aca ggc ttc ggc cgc atg ggc gcg atg acc       816
Ile Phe Asp Glu Val Ile Thr Gly Phe Gly Arg Met Gly Ala Met Thr
            260                 265                 270 ggc tcg gaa gcc ttc ggc gtt acc ccg gac ctg atg tgc atc gcc aag       864
Gly Ser Glu Ala Phe Gly Val Thr Pro Asp Leu Met Cys Ile Ala Lys
            275                 280                 285 cag gtg acc aac ggc gcc atc ccg atg ggc gca gtg att gcc agc agc       912
Gln Val Thr Asn Gly Ala Ile Pro Met Gly Ala Val Ile Ala Ser Ser
            290                 295                 300 gag atc tac cag acc ttc atg aac cag ccg acc ccg gaa tac gcc gtg       960
Glu Ile Tyr Gln Thr Phe Met Asn Gln Pro Thr Pro Glu Tyr Ala Val
305                 310                 315                 320 gaa ttc cca cac ggc tac acc tat tcg gcg cac ccg gta gcc tgt gcc      1008
Glu Phe Pro His Gly Tyr Thr Tyr Ser Ala His Pro Val Ala Cys Ala
            325                 330                 335 gcc ggt ctc gcc gcg ctg gac ctg ctg cag aag gaa aac ctg gtg cag      1056
Ala Gly Leu Ala Ala Leu Asp Leu Leu Gln Lys Glu Asn Leu Val Gln
            340                 345                 350 tcc gcg gct gaa ctg gcg ccg cat ttc gag aag ctg ctg cac ggc gtg      1104
Ser Ala Ala Glu Leu Ala Pro His Phe Glu Lys Leu Leu His Gly Val
            355                 360                 365 aag ggc acc aag aat atc gtc gat atc cgc aac tac ggc ctg gcc ggc      1152
Lys Gly Thr Lys Asn Ile Val Asp Ile Arg Asn Tyr Gly Leu Ala Gly
            370                 375                 380 gcc atc cag atc gcc gcc cgt gac ggt gat gcc atc gtt cgc cct tac      1200
Ala Ile Gln Ile Ala Ala Arg Asp Gly Asp Ala Ile Val Arg Pro Tyr
385                 390                 395                 400
```

```
gaa gcg gcc atg aag ctg tgg aaa gcg ggc ttc tat gta cgc ttt ggt    1248
Glu Ala Ala Met Lys Leu Trp Lys Ala Gly Phe Tyr Val Arg Phe Gly
            405                 410                 415 ggc gac acc ctg cag ttc ggc cca acc ttc aat acc aag ccg cag gaa    1296
Gly Asp Thr Leu Gln Phe Gly Pro Thr Phe Asn Thr Lys Pro Gln Glu
        420                 425                 430 ctg gac cgc ttg ttc gat gct gtt ggc gaa acc ctg aac ctg atc gac    1344
Leu Asp Arg Leu Phe Asp Ala Val Gly Glu Thr Leu Asn Leu Ile Asp
    435                 440                 445 tga                                                                1347

<210> SEQ ID NO 4
<211> LENGTH: 448
<212> TYPE: PRT
<213> ORGANISM: Pseudomonas putida

<400> SEQUENCE: 4

Met Asn Met Pro Glu Thr Gly Pro Ala Gly Ile Ala Ser Gln Leu Lys
1               5                   10                  15

Leu Asp Ala His Trp Met Pro Tyr Thr Ala Asn Arg Asn Phe Gln Arg
            20                  25                  30

Asp Pro Arg Leu Ile Val Ala Ala Glu Gly Asn Tyr Leu Val Asp Asp
        35                  40                  45

His Gly Arg Lys Ile Phe Asp Ala Leu Ser Gly Leu Trp Thr Cys Gly
    50                  55                  60

Ala Gly His Thr Arg Lys Glu Ile Ala Asp Ala Val Thr Arg Gln Leu
65                  70                  75                  80

Ser Thr Leu Asp Tyr Ser Pro Ala Phe Gln Phe Gly His Pro Leu Ser
                85                  90                  95

Phe Gln Leu Ala Glu Lys Ile Ala Glu Leu Val Pro Gly Asn Leu Asn
            100                 105                 110

His Val Phe Tyr Thr Asn Ser Gly Ser Glu Cys Ala Asp Thr Ala Leu
        115                 120                 125

Lys Met Val Arg Ala Tyr Trp Arg Leu Lys Gly Gln Ala Thr Lys Thr
    130                 135                 140

Lys Ile Ile Gly Arg Ala Arg Gly Tyr His Gly Val Asn Ile Ala Gly
145                 150                 155                 160

Thr Ser Leu Gly Gly Val Asn Gly Asn Arg Lys Met Phe Gly Gln Leu
                165                 170                 175

Leu Asp Val Asp His Leu Pro His Thr Val Leu Pro Val Asn Ala Phe
            180                 185                 190

Ser Lys Gly Leu Pro Glu Glu Gly Ile Ala Leu Ala Asp Glu Met
        195                 200                 205

Leu Lys Leu Ile Glu Leu His Asp Ala Ser Asn Ile Ala Ala Val Ile
    210                 215                 220

Val Glu Pro Leu Ala Gly Ser Ala Gly Val Leu Pro Pro Lys Gly
225                 230                 235                 240

Tyr Leu Lys Arg Leu Arg Glu Ile Cys Thr Gln His Asn Ile Leu Leu
                245                 250                 255

Ile Phe Asp Glu Val Ile Thr Gly Phe Gly Arg Met Gly Ala Met Thr
            260                 265                 270

Gly Ser Glu Ala Phe Gly Val Thr Pro Asp Leu Met Cys Ile Ala Lys
        275                 280                 285

Gln Val Thr Asn Gly Ala Ile Pro Met Gly Ala Val Ile Ala Ser Ser
    290                 295                 300
```

```
Glu Ile Tyr Gln Thr Phe Met Asn Gln Pro Thr Pro Glu Tyr Ala Val
305                 310                 315                 320

Glu Phe Pro His Gly Tyr Thr Tyr Ser Ala His Pro Val Ala Cys Ala
            325                 330                 335

Ala Gly Leu Ala Ala Leu Asp Leu Leu Gln Lys Glu Asn Leu Val Gln
        340                 345                 350

Ser Ala Ala Glu Leu Ala Pro His Phe Glu Lys Leu Leu His Gly Val
        355                 360                 365

Lys Gly Thr Lys Asn Ile Val Asp Ile Arg Asn Tyr Gly Leu Ala Gly
    370                 375                 380

Ala Ile Gln Ile Ala Ala Arg Asp Gly Asp Ala Ile Val Arg Pro Tyr
385                 390                 395                 400

Glu Ala Ala Met Lys Leu Trp Lys Ala Gly Phe Tyr Val Arg Phe Gly
                405                 410                 415

Gly Asp Thr Leu Gln Phe Gly Pro Thr Phe Asn Thr Lys Pro Gln Glu
            420                 425                 430

Leu Asp Arg Leu Phe Asp Ala Val Gly Glu Thr Leu Asn Leu Ile Asp
            435                 440                 445

<210> SEQ ID NO 5
<211> LENGTH: 1365
<212> TYPE: DNA
<213> ORGANISM: Pseudomonas chlororaphis
<220> FEATURE:
<221> NAME/KEY: CDS
<222> LOCATION: (1)..(1362)

<400> SEQUENCE: 5 atg acc agc aac aac ccg caa acc cgt gag tgg caa acc ctc agc agc    48
Met Thr Ser Asn Asn Pro Gln Thr Arg Glu Trp Gln Thr Leu Ser Ser
1               5                   10                  15 gag cac cac ctg gca ccg ttc agc gac ttc aag cag ttg aag gag aag    96
Glu His His Leu Ala Pro Phe Ser Asp Phe Lys Gln Leu Lys Glu Lys
                20                  25                  30 ggg ccg cgg atc atc acc aat gcc gag ggc gtt tac ctc tgg gac agc   144
Gly Pro Arg Ile Ile Thr Asn Ala Glu Gly Val Tyr Leu Trp Asp Ser
            35                  40                  45 gag ggc aac aag atc ctc gac ggc atg gcc ggg ctg tgg tgc gtg gcg   192
Glu Gly Asn Lys Ile Leu Asp Gly Met Ala Gly Leu Trp Cys Val Ala
    50                  55                  60 atc ggt tac ggc cgc gaa gaa ctg gcc gaa gcc gcc agc aag cag atg   240
Ile Gly Tyr Gly Arg Glu Glu Leu Ala Glu Ala Ala Ser Lys Gln Met
65                  70                  75                  80 cgc gag ctg ccg tac tac aac ctg ttc ttc cag acc gct cac ccg ccg   288
Arg Glu Leu Pro Tyr Tyr Asn Leu Phe Phe Gln Thr Ala His Pro Pro
                85                  90                  95 gcg ctg gaa ctg gcc aag gcc atc tcc gat gtt gcc ccg cag ggc atg   336
Ala Leu Glu Leu Ala Lys Ala Ile Ser Asp Val Ala Pro Gln Gly Met
                100                 105                 110 aat cat gtg ttc ttc acc ggt tcc ggt tcc gaa ggc aac gac acc atg   384
Asn His Val Phe Phe Thr Gly Ser Gly Ser Glu Gly Asn Asp Thr Met
            115                 120                 125 ctg cgc atg gtt cgc cac tac tgg gcg atc aag ggc cag ccg aag aag   432
Leu Arg Met Val Arg His Tyr Trp Ala Ile Lys Gly Gln Pro Lys Lys
        130                 135                 140 aaa acc atc atc agc cgg gtc aac ggc tat cac ggc tcc acc gtg gcc   480
Lys Thr Ile Ile Ser Arg Val Asn Gly Tyr His Gly Ser Thr Val Ala
145                 150                 155                 160 ggc gcg agc ctg ggc ggc atg acc tat atg cac gaa cag ggc gac ttg   528
```

```
                Gly Ala Ser Leu Gly Gly Met Thr Tyr Met His Glu Gln Gly Asp Leu
                                165                 170                 175 ccg atc ccg ggc atc gtg cat atc cca cag cct tac tgg ttc ggt gaa             576
Pro Ile Pro Gly Ile Val His Ile Pro Gln Pro Tyr Trp Phe Gly Glu
            180                 185                 190 ggc ggc gac atg acc ccg gac gag ttc ggg acc tgg gcg gcc aac cag             624
Gly Gly Asp Met Thr Pro Asp Glu Phe Gly Thr Trp Ala Ala Asn Gln
            195                 200                 205 ctg gaa gag aag att ctc gaa ctc ggc gtc gat aac gtc ggc gcc ttc             672
Leu Glu Glu Lys Ile Leu Glu Leu Gly Val Asp Asn Val Gly Ala Phe
    210                 215                 220 att gcc gag ccg atc cag ggt gcg ggc ggc gtg atc gtg ccg ccg gac             720
Ile Ala Glu Pro Ile Gln Gly Ala Gly Gly Val Ile Val Pro Pro Asp
225                 230                 235                 240 agc tac tgg ccg cga atc aag gaa atc ctc gcc aag tac gac atc ctg             768
Ser Tyr Trp Pro Arg Ile Lys Glu Ile Leu Ala Lys Tyr Asp Ile Leu
                245                 250                 255 ttc gtc gcc gac gag gtg atc tgt ggg ttc ggg cgt acc ggt gag tgg             816
Phe Val Ala Asp Glu Val Ile Cys Gly Phe Gly Arg Thr Gly Glu Trp
            260                 265                 270 ttc ggt agc gat ttc tac gac ctc aag ccg gac atg atg acc atc gcc             864
Phe Gly Ser Asp Phe Tyr Asp Leu Lys Pro Asp Met Met Thr Ile Ala
            275                 280                 285 aag ggc ctg acc tcc ggc tac atc ccc atg ggt ggc ctg gtg gtg cgc             912
Lys Gly Leu Thr Ser Gly Tyr Ile Pro Met Gly Gly Leu Val Val Arg
    290                 295                 300 gac gaa gtg gtg gcg gtg ctc aac gag ggc ggc gat ttc aac cac ggt             960
Asp Glu Val Val Ala Val Leu Asn Glu Gly Gly Asp Phe Asn His Gly
305                 310                 315                 320 ttc act tat tcc ggg cac ccg gtg gcc gcc gcc gtg gcc ctg gaa aac            1008
Phe Thr Tyr Ser Gly His Pro Val Ala Ala Ala Val Ala Leu Glu Asn
                325                 330                 335 atc cgc atc atg cgc gac gag aaa att atc gag cgc gtc aag gca gaa            1056
Ile Arg Ile Met Arg Asp Glu Lys Ile Ile Glu Arg Val Lys Ala Glu
            340                 345                 350 acg gca ccc tat ttg cag aaa cgt ctg cgg gaa ctg aac gat cac ccg            1104
Thr Ala Pro Tyr Leu Gln Lys Arg Leu Arg Glu Leu Asn Asp His Pro
            355                 360                 365 ctg gtg ggt gag gtt cgc gga gtc ggc ctg ttg ggc gcc atc gag ctg            1152
Leu Val Gly Glu Val Arg Gly Val Gly Leu Leu Gly Ala Ile Glu Leu
    370                 375                 380 gtt cag gac aag gcc acc cgt gcg cgg tat gtc gga aaa ggc gtc ggc            1200
Val Gln Asp Lys Ala Thr Arg Ala Arg Tyr Val Gly Lys Gly Val Gly
385                 390                 395                 400 atg atc tgc cgg cag ttc tgc ttc gac aac ggc ctg atc atg cgc gcc            1248
Met Ile Cys Arg Gln Phe Cys Phe Asp Asn Gly Leu Ile Met Arg Ala
                405                 410                 415 gtg ggc gac acc atg atc att gct ccg ccc ctg gtg atc acc aag gag            1296
Val Gly Asp Thr Met Ile Ile Ala Pro Pro Leu Val Ile Thr Lys Glu
            420                 425                 430 gag atc gat gag ctg gtg agc aag gcc cgc aag tgc ctg gac ctg acc            1344
Glu Ile Asp Glu Leu Val Ser Lys Ala Arg Lys Cys Leu Asp Leu Thr
            435                 440                 445 ttg agt gcg ttg cag ggc taa                                                1365
Leu Ser Ala Leu Gln Gly
        450

<210> SEQ ID NO 6
<211> LENGTH: 454
<212> TYPE: PRT
```

<213> ORGANISM: Pseudomonas chlororaphis

<400> SEQUENCE: 6

```
Met Thr Ser Asn Asn Pro Gln Thr Arg Glu Trp Gln Thr Leu Ser Ser
1               5                   10                  15

Glu His His Leu Ala Pro Phe Ser Asp Phe Lys Gln Leu Lys Glu Lys
            20                  25                  30

Gly Pro Arg Ile Ile Thr Asn Ala Glu Gly Val Tyr Leu Trp Asp Ser
        35                  40                  45

Glu Gly Asn Lys Ile Leu Asp Gly Met Ala Gly Leu Trp Cys Val Ala
    50                  55                  60

Ile Gly Tyr Gly Arg Glu Glu Leu Ala Glu Ala Ser Lys Gln Met
65                  70                  75                  80

Arg Glu Leu Pro Tyr Tyr Asn Leu Phe Phe Gln Thr Ala His Pro Pro
                85                  90                  95

Ala Leu Glu Leu Ala Lys Ala Ile Ser Asp Val Ala Pro Gln Gly Met
            100                 105                 110

Asn His Val Phe Phe Thr Gly Ser Gly Ser Glu Gly Asn Asp Thr Met
            115                 120                 125

Leu Arg Met Val Arg His Tyr Trp Ala Ile Lys Gly Gln Pro Lys Lys
130                 135                 140

Lys Thr Ile Ile Ser Arg Val Asn Gly Tyr His Gly Ser Thr Val Ala
145                 150                 155                 160

Gly Ala Ser Leu Gly Gly Met Thr Tyr Met His Glu Gln Gly Asp Leu
                165                 170                 175

Pro Ile Pro Gly Ile Val His Ile Pro Gln Pro Tyr Trp Phe Gly Glu
            180                 185                 190

Gly Gly Asp Met Thr Pro Asp Glu Phe Gly Thr Trp Ala Ala Asn Gln
        195                 200                 205

Leu Glu Glu Lys Ile Leu Glu Leu Gly Val Asp Asn Val Gly Ala Phe
210                 215                 220

Ile Ala Glu Pro Ile Gln Gly Ala Gly Gly Val Ile Val Pro Pro Asp
225                 230                 235                 240

Ser Tyr Trp Pro Arg Ile Lys Glu Ile Leu Ala Lys Tyr Asp Ile Leu
                245                 250                 255

Phe Val Ala Asp Glu Val Ile Cys Gly Phe Gly Arg Thr Gly Glu Trp
            260                 265                 270

Phe Gly Ser Asp Phe Tyr Asp Leu Lys Pro Asp Met Met Thr Ile Ala
        275                 280                 285

Lys Gly Leu Thr Ser Gly Tyr Ile Pro Met Gly Gly Leu Val Val Arg
    290                 295                 300

Asp Glu Val Val Ala Val Leu Asn Glu Gly Gly Asp Phe Asn His Gly
305                 310                 315                 320

Phe Thr Tyr Ser Gly His Pro Val Ala Ala Val Ala Leu Glu Asn
                325                 330                 335

Ile Arg Ile Met Arg Asp Glu Lys Ile Ile Glu Arg Val Lys Ala Glu
            340                 345                 350

Thr Ala Pro Tyr Leu Gln Lys Arg Leu Arg Glu Leu Asn Asp His Pro
        355                 360                 365

Leu Val Gly Glu Val Arg Gly Val Gly Leu Leu Gly Ala Ile Glu Leu
    370                 375                 380

Val Gln Asp Lys Ala Thr Arg Ala Arg Tyr Val Gly Lys Gly Val Gly
385                 390                 395                 400
```

```
Met Ile Cys Arg Gln Phe Cys Phe Asp Asn Gly Leu Ile Met Arg Ala
            405                 410                 415

Val Gly Asp Thr Met Ile Ile Ala Pro Pro Leu Val Ile Thr Lys Glu
            420                 425                 430

Glu Ile Asp Glu Leu Val Ser Lys Ala Arg Lys Cys Leu Asp Leu Thr
            435                 440                 445

Leu Ser Ala Leu Gln Gly
        450

<210> SEQ ID NO 7
<211> LENGTH: 1350
<212> TYPE: DNA
<213> ORGANISM: Pseudomonas fluorescens
<220> FEATURE:
<221> NAME/KEY: CDS
<222> LOCATION: (1)..(1347)

<400> SEQUENCE: 7 atg aac atg ccc gaa aac gcc cca tcg tcc ctg gcc agc caa ttg aag     48
Met Asn Met Pro Glu Asn Ala Pro Ser Ser Leu Ala Ser Gln Leu Lys
1               5                   10                  15 ctg gac gct cac tgg atg ccg tac acg gcc aac cgt aac ttt cag cga     96
Leu Asp Ala His Trp Met Pro Tyr Thr Ala Asn Arg Asn Phe Gln Arg
            20                  25                  30 gac ccg cgc ctg atc gtg gcg gct gaa ggt agt tgg ttg att gat gac    144
Asp Pro Arg Leu Ile Val Ala Ala Glu Gly Ser Trp Leu Ile Asp Asp
        35                  40                  45 aag ggg cgc aag gtg tat gac tcg ttg tcg ggc ctg tgg acc tgc ggc    192
Lys Gly Arg Lys Val Tyr Asp Ser Leu Ser Gly Leu Trp Thr Cys Gly
    50                  55                  60 gcc ggg cac acg cgt aag gag atc cag gaa gcg gtc gcc aag caa ctg    240
Ala Gly His Thr Arg Lys Glu Ile Gln Glu Ala Val Ala Lys Gln Leu
65                  70                  75                  80 ggg act ttg gac tac tcg ccg ggc ttc cag tac ggt cat ccg ttg tcc    288
Gly Thr Leu Asp Tyr Ser Pro Gly Phe Gln Tyr Gly His Pro Leu Ser
                85                  90                  95 ttc caa ttg gcg gaa aag atc acc gac ctg acc cct ggc aac ctg aat    336
Phe Gln Leu Ala Glu Lys Ile Thr Asp Leu Thr Pro Gly Asn Leu Asn
            100                 105                 110 cat gtg ttc ttc acc gat tcc ggc tcc gag tgc gcc gat acc gcg gtg    384
His Val Phe Phe Thr Asp Ser Gly Ser Glu Cys Ala Asp Thr Ala Val
        115                 120                 125 aaa atg gtg cgt gcg tac tgg cgc ctc aaa ggc cag gcc acc aag acc    432
Lys Met Val Arg Ala Tyr Trp Arg Leu Lys Gly Gln Ala Thr Lys Thr
    130                 135                 140 aag atg atc ggt cgc gcc cgt ggt tat cac ggt gtg aac atc gcc ggt    480
Lys Met Ile Gly Arg Ala Arg Gly Tyr His Gly Val Asn Ile Ala Gly
145                 150                 155                 160 acc agc ctg ggt ggc gtc aac ggt aac cgt aag tta ttt ggc cag ggc    528
Thr Ser Leu Gly Gly Val Asn Gly Asn Arg Lys Leu Phe Gly Gln Gly
                165                 170                 175 ttg atg gac gtt gac cat ctg ccg cac acg ttg ctg gca agc aat gcc    576
Leu Met Asp Val Asp His Leu Pro His Thr Leu Leu Ala Ser Asn Ala
            180                 185                 190 ttc tcc cgc ggc atg ccg gag cag ggt ggt atc gcg ttg gcc gat gag    624
Phe Ser Arg Gly Met Pro Glu Gln Gly Gly Ile Ala Leu Ala Asp Glu
        195                 200                 205 ctg ctc aag ctg att gaa ttg cac gat gcg tcg aac atc gct gcg gtg    672
Leu Leu Lys Leu Ile Glu Leu His Asp Ala Ser Asn Ile Ala Ala Val
    210                 215                 220
```

-continued

```
ttt gtc gag ccg atg gcg ggt tcc gct ggc gtg ctg gtg ccg cct cag      720
Phe Val Glu Pro Met Ala Gly Ser Ala Gly Val Leu Val Pro Pro Gln
225                 230                 235                 240 ggt tac ctc aag cgc ctg cgt gag atc tgc gat caa cac aac atc ctg      768
Gly Tyr Leu Lys Arg Leu Arg Glu Ile Cys Asp Gln His Asn Ile Leu
            245                 250                 255 ctg gtg ttc gat gaa gtg atc acc ggt ttc ggc cgt act ggc tcg atg      816
Leu Val Phe Asp Glu Val Ile Thr Gly Phe Gly Arg Thr Gly Ser Met
        260                 265                 270 ttc ggt gcc gac agc ttc ggc gtg acc ccg gac ctg atg tgc atc gcc      864
Phe Gly Ala Asp Ser Phe Gly Val Thr Pro Asp Leu Met Cys Ile Ala
    275                 280                 285 aag caa gtc acc aac ggc gcc atc ccg atg ggc gcg gtg atc gcc agc      912
Lys Gln Val Thr Asn Gly Ala Ile Pro Met Gly Ala Val Ile Ala Ser
290                 295                 300 agc gag atc tat cag acg ttc atg aac cag gcg acg ccg gag tac gca      960
Ser Glu Ile Tyr Gln Thr Phe Met Asn Gln Ala Thr Pro Glu Tyr Ala
305                 310                 315                 320 gtt gag ttt ccg cac ggc tac acc tat tcg gcg cac ccg gta gcc tgc     1008
Val Glu Phe Pro His Gly Tyr Thr Tyr Ser Ala His Pro Val Ala Cys
            325                 330                 335 gcc gcc ggc ctg gct gca ttg gag ctg ttg cag aag gaa aac ctg gtg     1056
Ala Ala Gly Leu Ala Ala Leu Glu Leu Leu Gln Lys Glu Asn Leu Val
        340                 345                 350 cag agc gtc gcc gaa gtc gcc ccg cac ttt gag aat gcg ctg cat ggc     1104
Gln Ser Val Ala Glu Val Ala Pro His Phe Glu Asn Ala Leu His Gly
    355                 360                 365 ctg aag ggc agc aag aac gtc atc gac atc cgc aac tac ggg ctt gcg     1152
Leu Lys Gly Ser Lys Asn Val Ile Asp Ile Arg Asn Tyr Gly Leu Ala
370                 375                 380 ggc gct atc cag att gcc ccg cgt gac ggt gat gcg atc gtg cgc ccc     1200
Gly Ala Ile Gln Ile Ala Pro Arg Asp Gly Asp Ala Ile Val Arg Pro
385                 390                 395                 400 ttt gag gcc ggc atg gcc ttg tgg aaa gcc ggt ttc tac gtg cgt ttt     1248
Phe Glu Ala Gly Met Ala Leu Trp Lys Ala Gly Phe Tyr Val Arg Phe
            405                 410                 415 ggt ggc gac acc ctg cag ttc ggg cca acc ttc aac agc aag ccg cag     1296
Gly Gly Asp Thr Leu Gln Phe Gly Pro Thr Phe Asn Ser Lys Pro Gln
        420                 425                 430 gac ctg gat cgc ctg ttc gat gcg gtc ggc gaa gtg ctg aac aag atc     1344
Asp Leu Asp Arg Leu Phe Asp Ala Val Gly Glu Val Leu Asn Lys Ile
    435                 440                 445 gac tga                                                              1350
Asp

<210> SEQ ID NO 8
<211> LENGTH: 449
<212> TYPE: PRT
<213> ORGANISM: Pseudomonas fluorescens

<400> SEQUENCE: 8

Met Asn Met Pro Glu Asn Ala Pro Ser Ser Leu Ala Ser Gln Leu Lys
1               5                   10                  15

Leu Asp Ala His Trp Met Pro Tyr Thr Ala Asn Arg Asn Phe Gln Arg
            20                  25                  30

Asp Pro Arg Leu Ile Val Ala Ala Glu Gly Ser Trp Leu Ile Asp Asp
        35                  40                  45

Lys Gly Arg Lys Val Tyr Asp Ser Leu Ser Gly Leu Trp Thr Cys Gly
    50                  55                  60
```

```
Ala Gly His Thr Arg Lys Glu Ile Gln Glu Ala Val Ala Lys Gln Leu
 65                  70                  75                  80

Gly Thr Leu Asp Tyr Ser Pro Gly Phe Gln Tyr Gly His Pro Leu Ser
                 85                  90                  95

Phe Gln Leu Ala Glu Lys Ile Thr Asp Leu Thr Pro Gly Asn Leu Asn
            100                 105                 110

His Val Phe Phe Thr Asp Ser Gly Ser Glu Cys Ala Asp Thr Ala Val
        115                 120                 125

Lys Met Val Arg Ala Tyr Trp Arg Leu Lys Gly Gln Ala Thr Lys Thr
130                 135                 140

Lys Met Ile Gly Arg Ala Arg Gly Tyr His Gly Val Asn Ile Ala Gly
145                 150                 155                 160

Thr Ser Leu Gly Gly Val Asn Gly Asn Arg Lys Leu Phe Gly Gln Gly
                165                 170                 175

Leu Met Asp Val Asp His Leu Pro His Thr Leu Leu Ala Ser Asn Ala
            180                 185                 190

Phe Ser Arg Gly Met Pro Glu Gln Gly Ile Ala Leu Ala Asp Glu
        195                 200                 205

Leu Leu Lys Leu Ile Glu Leu His Asp Ala Ser Asn Ile Ala Ala Val
210                 215                 220

Phe Val Glu Pro Met Ala Gly Ser Ala Gly Val Leu Val Pro Pro Gln
225                 230                 235                 240

Gly Tyr Leu Lys Arg Leu Arg Glu Ile Cys Asp Gln His Asn Ile Leu
                245                 250                 255

Leu Val Phe Asp Glu Val Ile Thr Gly Phe Gly Arg Thr Gly Ser Met
            260                 265                 270

Phe Gly Ala Asp Ser Phe Gly Val Thr Pro Asp Leu Met Cys Ile Ala
        275                 280                 285

Lys Gln Val Thr Asn Gly Ala Ile Pro Met Gly Ala Val Ile Ala Ser
290                 295                 300

Ser Glu Ile Tyr Gln Thr Phe Met Asn Gln Ala Thr Pro Glu Tyr Ala
305                 310                 315                 320

Val Glu Phe Pro His Gly Tyr Thr Tyr Ser Ala His Pro Val Ala Cys
                325                 330                 335

Ala Ala Gly Leu Ala Ala Leu Glu Leu Leu Gln Lys Glu Asn Leu Val
            340                 345                 350

Gln Ser Val Ala Glu Val Ala Pro His Phe Glu Asn Ala Leu His Gly
        355                 360                 365

Leu Lys Gly Ser Lys Asn Val Ile Asp Ile Arg Asn Tyr Gly Leu Ala
370                 375                 380

Gly Ala Ile Gln Ile Ala Pro Arg Asp Gly Asp Ala Ile Val Arg Pro
385                 390                 395                 400

Phe Glu Ala Gly Met Ala Leu Trp Lys Ala Gly Phe Tyr Val Arg Phe
                405                 410                 415

Gly Gly Asp Thr Leu Gln Phe Gly Pro Thr Phe Asn Ser Lys Pro Gln
            420                 425                 430

Asp Leu Asp Arg Leu Phe Asp Ala Val Gly Glu Val Leu Asn Lys Ile
        435                 440                 445

Asp

<210> SEQ ID NO 9
<211> LENGTH: 1335
<212> TYPE: DNA
<213> ORGANISM: Pseudomonas syringae
```

```
<220> FEATURE:
<221> NAME/KEY: CDS
<222> LOCATION: (1)..(1332)

<400> SEQUENCE: 9 atg ttg cca ccc gaa aca cag cgt ctg atc gaa cag cac ggc atc aag      48
Met Leu Pro Pro Glu Thr Gln Arg Leu Ile Glu Gln His Gly Ile Lys
1               5                   10                  15 tac gta ctg gct cag ttc gtc gac att cat ggt tcg gcc aag acc aaa      96
Tyr Val Leu Ala Gln Phe Val Asp Ile His Gly Ser Ala Lys Thr Lys
            20                  25                  30 tcg gtt cct gtg aca ggt ctg gaa atg gtt gca gag gac ggt gcc ggc     144
Ser Val Pro Val Thr Gly Leu Glu Met Val Ala Glu Asp Gly Ala Gly
        35                  40                  45 ttt gcc ggt ttc gcg atc tgc ggg atg ggc atg gag cct cat ggg ccg     192
Phe Ala Gly Phe Ala Ile Cys Gly Met Gly Met Glu Pro His Gly Pro
    50                  55                  60 gac ttc atg gcc agg ggt gat ctg tcg tcg ctg acc ccg gtg cca tgg     240
Asp Phe Met Ala Arg Gly Asp Leu Ser Ser Leu Thr Pro Val Pro Trp
65                  70                  75                  80 cag ccg ggc tat gga cgg gtg gtg tgc atc ggc cat gtg gat ggc aaa     288
Gln Pro Gly Tyr Gly Arg Val Val Cys Ile Gly His Val Asp Gly Lys
                85                  90                  95 ccc tgg ccc tat gac agc cgc tat gtg ctg cag cag cag gtc gaa cgc     336
Pro Trp Pro Tyr Asp Ser Arg Tyr Val Leu Gln Gln Gln Val Glu Arg
            100                 105                 110 ctc agt cag cgt ggc tgg agc ctc aat acc ggc ctg gag ccc gag ttc     384
Leu Ser Gln Arg Gly Trp Ser Leu Asn Thr Gly Leu Glu Pro Glu Phe
        115                 120                 125 agc ctg ttc aag cgc gat gtc acc ggc agc ctg cag atg gtc gat gcc     432
Ser Leu Phe Lys Arg Asp Val Thr Gly Ser Leu Gln Met Val Asp Ala
    130                 135                 140 agc gat aac ctc gac aag cct tgc tac gac tac aag ggg ctg tcg cgc     480
Ser Asp Asn Leu Asp Lys Pro Cys Tyr Asp Tyr Lys Gly Leu Ser Arg
145                 150                 155                 160 tct cgc gag ttt ctc gag cgc ctg acc gag gca ttg cag ccg gtg ggt     528
Ser Arg Glu Phe Leu Glu Arg Leu Thr Glu Ala Leu Gln Pro Val Gly
                165                 170                 175 ttc gac att tat cag atc gat cat gaa gac gcc aac ggc cag ttc gag     576
Phe Asp Ile Tyr Gln Ile Asp His Glu Asp Ala Asn Gly Gln Phe Glu
            180                 185                 190 atc aat tac acc tac agc gag gcc atg gaa tcg gct gac cgt ttc acc     624
Ile Asn Tyr Thr Tyr Ser Glu Ala Met Glu Ser Ala Asp Arg Phe Thr
        195                 200                 205 ttc ttc cgc atg gcc gcc ggt gag atc gcc aat gac atg ggc atg atc     672
Phe Phe Arg Met Ala Ala Gly Glu Ile Ala Asn Asp Met Gly Met Ile
    210                 215                 220 tgc tcg ttc atg ccc aag ccc gat ccc aaa cgg gcc ggc aat ggc atg     720
Cys Ser Phe Met Pro Lys Pro Asp Pro Lys Arg Ala Gly Asn Gly Met
225                 230                 235                 240 cac ttt cac ttg tcg atc gcc agt gcc agt aac aag aac ctg ttc cac     768
His Phe His Leu Ser Ile Ala Ser Ala Ser Asn Lys Asn Leu Phe His
                245                 250                 255 gat gcc agc gat ccg agc ggc atg ggg ttg tcg acg ctg gcc tat cac     816
Asp Ala Ser Asp Pro Ser Gly Met Gly Leu Ser Thr Leu Ala Tyr His
            260                 265                 270 ttc gct gcg ggc ctg ctg gct cac ggg cct gcg ctg tgc gcc ttt gcg     864
Phe Ala Ala Gly Leu Leu Ala His Gly Pro Ala Leu Cys Ala Phe Ala
        275                 280                 285 gca ccc acg gtc aac tcc tac aaa cgc ctg gtg gtc ggc aac tca ctg     912
```

```
Ala Pro Thr Val Asn Ser Tyr Lys Arg Leu Val Val Gly Asn Ser Leu
    290                 295                 300 tcg ggc gcc acc tgg gcc ccg gcg ttt att gcc ttc ggc gcc aac aac      960
Ser Gly Ala Thr Trp Ala Pro Ala Phe Ile Ala Phe Gly Ala Asn Asn
305                 310                 315                 320 cgc tcg gcg atg gtg cgc gtg ccc tat ggc cgc ctg gag ttt cgt ctg     1008
Arg Ser Ala Met Val Arg Val Pro Tyr Gly Arg Leu Glu Phe Arg Leu
                325                 330                 335 ccc gac gcc ggt tgc aat ccg tat ctg gtc agc gcc gca atc att gcc     1056
Pro Asp Ala Gly Cys Asn Pro Tyr Leu Val Ser Ala Ala Ile Ile Ala
            340                 345                 350 gca ggc ctg gac ggt atc gac cgg caa ctg gag atc gat cac gtc tgc     1104
Ala Gly Leu Asp Gly Ile Asp Arg Gln Leu Glu Ile Asp His Val Cys
        355                 360                 365 aac gag aac ctc tac aaa ttg agc ctc gaa gag atc gcc gca cgg ggc     1152
Asn Glu Asn Leu Tyr Lys Leu Ser Leu Glu Glu Ile Ala Ala Arg Gly
    370                 375                 380 atc aag acc ctg ccg cag tcg ctc aac gaa gcc tgc gac gcg ctg caa     1200
Ile Lys Thr Leu Pro Gln Ser Leu Asn Glu Ala Cys Asp Ala Leu Gln
385                 390                 395                 400 gcc gac ccg ttg ttt ggc gaa gtg ctg ggc agc gag att gtc gat gaa     1248
Ala Asp Pro Leu Phe Gly Glu Val Leu Gly Ser Glu Ile Val Asp Glu
                405                 410                 415 ttc atc cgc ctc aag cgc atg gag tgg gtg gaa tac agc cgc cac gtg     1296
Phe Ile Arg Leu Lys Arg Met Glu Trp Val Glu Tyr Ser Arg His Val
            420                 425                 430 agc gat tgg gaa gtg aag cgc tat atc gaa ttt ttc tag                  1335
Ser Asp Trp Glu Val Lys Arg Tyr Ile Glu Phe Phe
        435                 440
```

<210> SEQ ID NO 10
<211> LENGTH: 444
<212> TYPE: PRT
<213> ORGANISM: Pseudomonas syringae

<400> SEQUENCE: 10

```
Met Leu Pro Pro Glu Thr Gln Arg Leu Ile Glu Gln His Gly Ile Lys
1               5                   10                  15

Tyr Val Leu Ala Gln Phe Val Asp Ile His Gly Ser Ala Lys Thr Lys
            20                  25                  30

Ser Val Pro Val Thr Gly Leu Glu Met Val Ala Glu Asp Gly Ala Gly
        35                  40                  45

Phe Ala Gly Phe Ala Ile Cys Gly Met Gly Met Glu Pro His Gly Pro
    50                  55                  60

Asp Phe Met Ala Arg Gly Asp Leu Ser Ser Leu Thr Pro Val Pro Trp
65              70                  75                  80

Gln Pro Gly Tyr Gly Arg Val Val Cys Ile Gly His Val Asp Gly Lys
                85                  90                  95

Pro Trp Pro Tyr Asp Ser Arg Tyr Val Leu Gln Gln Gln Val Glu Arg
            100                 105                 110

Leu Ser Gln Arg Gly Trp Ser Leu Asn Thr Gly Leu Glu Pro Glu Phe
        115                 120                 125

Ser Leu Phe Lys Arg Asp Val Thr Gly Ser Leu Gln Met Val Asp Ala
    130                 135                 140

Ser Asp Asn Leu Asp Lys Pro Cys Tyr Asp Tyr Lys Gly Leu Ser Arg
145                 150                 155                 160

Ser Arg Glu Phe Leu Glu Arg Leu Thr Glu Ala Leu Gln Pro Val Gly
                165                 170                 175
```

```
Phe Asp Ile Tyr Gln Ile Asp His Glu Asp Ala Asn Gly Gln Phe Glu
            180                 185                 190

Ile Asn Tyr Thr Tyr Ser Glu Ala Met Glu Ser Ala Asp Arg Phe Thr
        195                 200                 205

Phe Phe Arg Met Ala Ala Gly Glu Ile Ala Asn Asp Met Gly Met Ile
210                 215                 220

Cys Ser Phe Met Pro Lys Pro Asp Pro Lys Arg Ala Gly Asn Gly Met
225                 230                 235                 240

His Phe His Leu Ser Ile Ala Ser Ala Ser Asn Lys Asn Leu Phe His
            245                 250                 255

Asp Ala Ser Asp Pro Ser Gly Met Gly Leu Ser Thr Leu Ala Tyr His
        260                 265                 270

Phe Ala Ala Gly Leu Leu Ala His Gly Pro Ala Leu Cys Ala Phe Ala
    275                 280                 285

Ala Pro Thr Val Asn Ser Tyr Lys Arg Leu Val Val Gly Asn Ser Leu
290                 295                 300

Ser Gly Ala Thr Trp Ala Pro Ala Phe Ile Ala Phe Gly Ala Asn Asn
305                 310                 315                 320

Arg Ser Ala Met Val Arg Val Pro Tyr Gly Arg Leu Glu Phe Arg Leu
            325                 330                 335

Pro Asp Ala Gly Cys Asn Pro Tyr Leu Val Ser Ala Ala Ile Ile Ala
        340                 345                 350

Ala Gly Leu Asp Gly Ile Asp Arg Gln Leu Glu Ile Asp His Val Cys
    355                 360                 365

Asn Glu Asn Leu Tyr Lys Leu Ser Leu Glu Glu Ile Ala Ala Arg Gly
370                 375                 380

Ile Lys Thr Leu Pro Gln Ser Leu Asn Glu Ala Cys Asp Ala Leu Gln
385                 390                 395                 400

Ala Asp Pro Leu Phe Gly Glu Val Leu Gly Ser Glu Ile Val Asp Glu
            405                 410                 415

Phe Ile Arg Leu Lys Arg Met Glu Trp Val Glu Tyr Ser Arg His Val
        420                 425                 430

Ser Asp Trp Glu Val Lys Arg Tyr Ile Glu Phe Phe
    435                 440

<210> SEQ ID NO 11
<211> LENGTH: 2676
<212> TYPE: DNA
<213> ORGANISM: Escherichia coli
<220> FEATURE:
<221> NAME/KEY: CDS
<222> LOCATION: (1)..(2673)

<400> SEQUENCE: 11 atg gct gtt act aat gtc gct gaa ctt aac gca ctc gta gag cgt gta      48
Met Ala Val Thr Asn Val Ala Glu Leu Asn Ala Leu Val Glu Arg Val
1               5                   10                  15 aaa aaa gcc cag cgt gaa tat gcc agt ttc act caa gag caa gta gac      96
Lys Lys Ala Gln Arg Glu Tyr Ala Ser Phe Thr Gln Glu Gln Val Asp
            20                  25                  30 aaa atc ttc cgc gcc gcc gct ctg gct gct gca gat gct cga atc cca     144
Lys Ile Phe Arg Ala Ala Ala Leu Ala Ala Ala Asp Ala Arg Ile Pro
        35                  40                  45 ctc gcg aaa atg gcc gtt gcc gaa tcc ggc atg ggt atc gtc gaa gat     192
Leu Ala Lys Met Ala Val Ala Glu Ser Gly Met Gly Ile Val Glu Asp
    50                  55                  60
```

-continued

| | | |
|---|---|---|
| aaa gtg atc aaa aac cac ttt gct tct gaa tat atc tac aac gcc tat<br>Lys Val Ile Lys Asn His Phe Ala Ser Glu Tyr Ile Tyr Asn Ala Tyr<br>65                          70                       75                       80 | 240 |
| aaa gat gaa aaa acc tgt ggt gtt ctg tct gaa gac gac act ttt ggt<br>Lys Asp Glu Lys Thr Cys Gly Val Leu Ser Glu Asp Asp Thr Phe Gly<br>                     85                       90                       95 | 288 |
| acc atc act atc gct gaa cca atc ggt att att tgc ggt atc gtt ccg<br>Thr Ile Thr Ile Ala Glu Pro Ile Gly Ile Ile Cys Gly Ile Val Pro<br>                 100                   105                   110 | 336 |
| acc act aac ccg act tca act gct atc ttc aaa tcg ctg atc agt ctg<br>Thr Thr Asn Pro Thr Ser Thr Ala Ile Phe Lys Ser Leu Ile Ser Leu<br>          115                   120                   125 | 384 |
| aag acc cgt aac gcc att atc ttc tcc ccg cac ccg cgt gca aaa gat<br>Lys Thr Arg Asn Ala Ile Ile Phe Ser Pro His Pro Arg Ala Lys Asp<br>130                       135                   140 | 432 |
| gcc acc aac aaa gcg gct gat atc gtt ctg cag gct gct atc gct gcc<br>Ala Thr Asn Lys Ala Ala Asp Ile Val Leu Gln Ala Ala Ile Ala Ala<br>145                       150                   155                   160 | 480 |
| ggt gct ccg aaa gat ctg atc ggc tgg atc gat caa cct tct gtt gaa<br>Gly Ala Pro Lys Asp Leu Ile Gly Trp Ile Asp Gln Pro Ser Val Glu<br>                     165                   170                   175 | 528 |
| ctg tct aac gca ctg atg cac cac cca gac atc aac ctg atc ctc gcg<br>Leu Ser Asn Ala Leu Met His His Pro Asp Ile Asn Leu Ile Leu Ala<br>             180                   185                   190 | 576 |
| act ggt ggt ccg ggc atg gtt aaa gcc gca tac agc tcc ggt aaa cca<br>Thr Gly Gly Pro Gly Met Val Lys Ala Ala Tyr Ser Ser Gly Lys Pro<br>         195                   200                   205 | 624 |
| gct atc ggt gta ggc gcg ggc aac act cca gtt gtt atc gat gaa act<br>Ala Ile Gly Val Gly Ala Gly Asn Thr Pro Val Val Ile Asp Glu Thr<br>210                       215                   220 | 672 |
| gct gat atc aaa cgt gca gtt gca tct gta ctg atg tcc aaa acc ttc<br>Ala Asp Ile Lys Arg Ala Val Ala Ser Val Leu Met Ser Lys Thr Phe<br>225                       230                   235                   240 | 720 |
| gac aac ggc gta atc tgt gct tct gaa cag tct gtt gtt gtt gtt gac<br>Asp Asn Gly Val Ile Cys Ala Ser Glu Gln Ser Val Val Val Val Asp<br>                     245                   250                   255 | 768 |
| tct gtt tat gac gct gta cgt gaa cgt ttt gca acc cac ggc ggc tat<br>Ser Val Tyr Asp Ala Val Arg Glu Arg Phe Ala Thr His Gly Gly Tyr<br>             260                   265                   270 | 816 |
| ctg ttg cag ggt aaa gag ctg aaa gct gtt cag gat gtt atc ctg aaa<br>Leu Leu Gln Gly Lys Glu Leu Lys Ala Val Gln Asp Val Ile Leu Lys<br>         275                   280                   285 | 864 |
| aac ggt gcg ctg aac gcg gct atc gtt ggt cag cca gcc tat aaa att<br>Asn Gly Ala Leu Asn Ala Ala Ile Val Gly Gln Pro Ala Tyr Lys Ile<br>290                       295                   300 | 912 |
| gct gaa ctg gca ggc ttc tct gta cca gaa aac acc aag att ctg atc<br>Ala Glu Leu Ala Gly Phe Ser Val Pro Glu Asn Thr Lys Ile Leu Ile<br>305                       310                   315                   320 | 960 |
| ggt gaa gtg acc gtt gtt gat gaa agc gaa ccg ttc gca cat gaa aaa<br>Gly Glu Val Thr Val Val Asp Glu Ser Glu Pro Phe Ala His Glu Lys<br>                     325                   330                   335 | 1008 |
| ctg tcc ccg act ctg gca atg tac cgc gct aaa gat ttc gaa gac gcg<br>Leu Ser Pro Thr Leu Ala Met Tyr Arg Ala Lys Asp Phe Glu Asp Ala<br>             340                   345                   350 | 1056 |
| gta gaa aaa gca gag aaa ctg gtt gct atg ggc ggt atc ggt cat acc<br>Val Glu Lys Ala Glu Lys Leu Val Ala Met Gly Gly Ile Gly His Thr<br>         355                   360                   365 | 1104 |
| tct tgc ctg tac act gac cag gat aac caa ccg gct cgc gtt tct tac<br>Ser Cys Leu Tyr Thr Asp Gln Asp Asn Gln Pro Ala Arg Val Ser Tyr<br>370                       375                   380 | 1152 |

-continued

```
ttc ggt cag aaa atg aaa acg gcg cgt atc ctg att aac acc cca gcg      1200
Phe Gly Gln Lys Met Lys Thr Ala Arg Ile Leu Ile Asn Thr Pro Ala
385                 390                 395                 400 tct cag ggt ggt atc ggt gac ctg tat aac ttc aaa ctc gca cct tcc      1248
Ser Gln Gly Gly Ile Gly Asp Leu Tyr Asn Phe Lys Leu Ala Pro Ser
            405                 410                 415 ctg act ctg ggt tgt ggt tct tgg ggt ggt aac tcc atc tct gaa aac      1296
Leu Thr Leu Gly Cys Gly Ser Trp Gly Gly Asn Ser Ile Ser Glu Asn
        420                 425                 430 gtt ggt ccg aaa cac ctg atc aac aag aaa acc gtt gct aag cga gct      1344
Val Gly Pro Lys His Leu Ile Asn Lys Lys Thr Val Ala Lys Arg Ala
    435                 440                 445 gaa aac atg ttg tgg cac aaa ctt ccg aaa tct atc tac ttc cgc cgt      1392
Glu Asn Met Leu Trp His Lys Leu Pro Lys Ser Ile Tyr Phe Arg Arg
450                 455                 460 ggc tcc ctg cca atc gcg ctg gat gaa gtg att act gat ggc cac aaa      1440
Gly Ser Leu Pro Ile Ala Leu Asp Glu Val Ile Thr Asp Gly His Lys
465                 470                 475                 480 cgt gcg ctc atc gtg act gac cgc ttc ctg ttc aac aat ggt tat gct      1488
Arg Ala Leu Ile Val Thr Asp Arg Phe Leu Phe Asn Asn Gly Tyr Ala
            485                 490                 495 gat cag atc act tcc gta ctg aaa gca gca ggc gtt gaa act gaa gtc      1536
Asp Gln Ile Thr Ser Val Leu Lys Ala Ala Gly Val Glu Thr Glu Val
        500                 505                 510 ttc ttc gaa gta gaa gcg gac ccg acc ctg agc atc gtt cgt aaa ggt      1584
Phe Phe Glu Val Glu Ala Asp Pro Thr Leu Ser Ile Val Arg Lys Gly
    515                 520                 525 gca gaa ctg gca aac tcc ttc aaa cca gac gtg att atc gcg ctg ggt      1632
Ala Glu Leu Ala Asn Ser Phe Lys Pro Asp Val Ile Ile Ala Leu Gly
530                 535                 540 ggt ggt tcc ccg atg gac gcc gcg aag atc atg tgg gtt atg tac gaa      1680
Gly Gly Ser Pro Met Asp Ala Ala Lys Ile Met Trp Val Met Tyr Glu
545                 550                 555                 560 cat ccg gaa act cac ttc gaa gag ctg gcg ctg cgc ttt atg gat atc      1728
His Pro Glu Thr His Phe Glu Glu Leu Ala Leu Arg Phe Met Asp Ile
            565                 570                 575 cgt aaa cgt atc tac aag ttc ccg aaa atg ggc gtg aaa gcg aaa atg      1776
Arg Lys Arg Ile Tyr Lys Phe Pro Lys Met Gly Val Lys Ala Lys Met
        580                 585                 590 atc gct gtc acc acc act tct ggt aca ggt tct gaa gtc act ccg ttt      1824
Ile Ala Val Thr Thr Thr Ser Gly Thr Gly Ser Glu Val Thr Pro Phe
    595                 600                 605 gcg gtt gta act gac gac gct act ggt cag aaa tat ccg ctg gca gac      1872
Ala Val Val Thr Asp Asp Ala Thr Gly Gln Lys Tyr Pro Leu Ala Asp
610                 615                 620 tat gcg ctg act ccg gat atg gcg att gtc gac gcc aac ctg gtt atg      1920
Tyr Ala Leu Thr Pro Asp Met Ala Ile Val Asp Ala Asn Leu Val Met
625                 630                 635                 640 gac atg ccg aag tcc ctg tgt gct ttc ggt ggt ctg gac gca gta act      1968
Asp Met Pro Lys Ser Leu Cys Ala Phe Gly Gly Leu Asp Ala Val Thr
            645                 650                 655 cac gcc atg gaa gct tat gtt tct gta ctg gca tct gag ttc tct gat      2016
His Ala Met Glu Ala Tyr Val Ser Val Leu Ala Ser Glu Phe Ser Asp
        660                 665                 670 ggt cag gct ctg cag gca ctg aaa ctg ctg aaa gaa tat ctg cca gcg      2064
Gly Gln Ala Leu Gln Ala Leu Lys Leu Leu Lys Glu Tyr Leu Pro Ala
    675                 680                 685 tcc tac cac gaa ggg tct aaa aat ccg gta gcg cgt gaa cgt gtt cac      2112
Ser Tyr His Glu Gly Ser Lys Asn Pro Val Ala Arg Glu Arg Val His
```

```
                                                                      690                     695                     700
         agt gca gcg act atc gcg ggt atc gcg ttt gcg aac gcc ttc ctg ggt       2160
         Ser Ala Ala Thr Ile Ala Gly Ile Ala Phe Ala Asn Ala Phe Leu Gly
         705                 710                     715                 720 gta tgt cac tca atg gcg cac aaa ctg ggt tcc cag ttc cat att ccg       2208
         Val Cys His Ser Met Ala His Lys Leu Gly Ser Gln Phe His Ile Pro
                         725                     730                 735 cac ggt ctg gca aac gcc ctg ctg att tgt aac gtt att cgc tac aat       2256
         His Gly Leu Ala Asn Ala Leu Leu Ile Cys Asn Val Ile Arg Tyr Asn
                     740                     745                 750 gcg aac gac aac ccg acc aag cag act gca ttc agc cag tat gac cgt       2304
         Ala Asn Asp Asn Pro Thr Lys Gln Thr Ala Phe Ser Gln Tyr Asp Arg
                 755                     760                     765 ccg cag gct cgc cgt cgt tat gct gaa att gcc gac cac ttg ggt ctg       2352
         Pro Gln Ala Arg Arg Arg Tyr Ala Glu Ile Ala Asp His Leu Gly Leu
             770                     775                     780 agc gca ccg ggc gac cgt act gct gct aag atc gag aaa ctg ctg gca       2400
         Ser Ala Pro Gly Asp Arg Thr Ala Ala Lys Ile Glu Lys Leu Leu Ala
         785                 790                     795                 800 tgg ctg gaa acg ctg aaa gct gaa ctg ggt att ccg aaa tct atc cgt       2448
         Trp Leu Glu Thr Leu Lys Ala Glu Leu Gly Ile Pro Lys Ser Ile Arg
                         805                     810                 815 gaa gct ggc gtt cag gaa gca gac ttc ctg gcg aac gtg gat aaa ctg       2496
         Glu Ala Gly Val Gln Glu Ala Asp Phe Leu Ala Asn Val Asp Lys Leu
                     820                     825                 830 tct gaa gat gca ttc gat gac cag tgc acc ggc gct aac ccg cgt tac       2544
         Ser Glu Asp Ala Phe Asp Asp Gln Cys Thr Gly Ala Asn Pro Arg Tyr
                 835                     840                     845 ccg ctg atc tcc gag ctg aaa cag att ctg ctg gat acc tac tac ggt       2592
         Pro Leu Ile Ser Glu Leu Lys Gln Ile Leu Leu Asp Thr Tyr Tyr Gly
             850                     855                     860 cgt gat tat gta gaa ggt gaa act gca gcg aag aaa gaa gct gct ccg       2640
         Arg Asp Tyr Val Glu Gly Glu Thr Ala Ala Lys Lys Glu Ala Ala Pro
         865                 870                     875                 880 gct aaa gct gag aaa aaa gcg aaa aaa tcc gct taa                       2676
         Ala Lys Ala Glu Lys Lys Ala Lys Lys Ser Ala
                         885                     890

<210> SEQ ID NO 12
<211> LENGTH: 891
<212> TYPE: PRT
<213> ORGANISM: Escherichia coli

<400> SEQUENCE: 12

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Leu Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Thr Phe Gly
            85                  90                  95

Thr Ile Thr Ile Ala Glu Pro Ile Gly Ile Ile Cys Gly Ile Val Pro
        100                 105                 110
```

```
Thr Thr Asn Pro Thr Ser Thr Ala Ile Phe Lys Ser Leu Ile Ser Leu
            115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
    290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Ala Arg Val Ser Tyr
    370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
    450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
        515                 520                 525

Ala Glu Leu Ala Asn Ser Phe Lys Pro Asp Val Ile Ile Ala Leu Gly
```

```
                530             535             540
Gly Gly Ser Pro Met Asp Ala Ala Lys Ile Met Trp Val Met Tyr Glu
545                 550                 555                 560

His Pro Glu Thr His Phe Glu Leu Ala Leu Arg Phe Met Asp Ile
                565                 570                 575

Arg Lys Arg Ile Tyr Lys Phe Pro Lys Met Gly Val Lys Ala Lys Met
                580                 585                 590

Ile Ala Val Thr Thr Thr Ser Gly Thr Gly Ser Glu Val Thr Pro Phe
                595                 600                 605

Ala Val Val Thr Asp Asp Ala Thr Gly Gln Lys Tyr Pro Leu Ala Asp
                610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
                675                 680                 685

Ser Tyr His Glu Gly Ser Lys Asn Pro Val Ala Arg Glu Arg Val His
690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
                740                 745                 750

Ala Asn Asp Asn Pro Thr Lys Gln Thr Ala Phe Ser Gln Tyr Asp Arg
                755                 760                 765

Pro Gln Ala Arg Arg Arg Tyr Ala Glu Ile Ala Asp His Leu Gly Leu
                770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
                820                 825                 830

Ser Glu Asp Ala Phe Asp Asp Gln Cys Thr Gly Ala Asn Pro Arg Tyr
                835                 840                 845

Pro Leu Ile Ser Glu Leu Lys Gln Ile Leu Leu Asp Thr Tyr Tyr Gly
                850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 13
<211> LENGTH: 1164
<212> TYPE: DNA
<213> ORGANISM: Escherichia coli
<220> FEATURE:
<221> NAME/KEY: CDS
<222> LOCATION: (1)..(1161)

<400> SEQUENCE: 13
```

```
atg aac aac ttt aat ctg cac acc cca acc cgc att ctg ttt ggt aaa    48
Met Asn Asn Phe Asn Leu His Thr Pro Thr Arg Ile Leu Phe Gly Lys
1               5                   10                  15 ggc gca atc gct ggt tta cgc gaa caa att cct cac gat gct cgc gta    96
Gly Ala Ile Ala Gly Leu Arg Glu Gln Ile Pro His Asp Ala Arg Val
            20                  25                  30 ttg att acc tac ggc ggc ggc agc gtg aaa aaa acc ggc gtt ctc gat   144
Leu Ile Thr Tyr Gly Gly Gly Ser Val Lys Lys Thr Gly Val Leu Asp
        35                  40                  45 caa gtt ctg gat gcc ctg aaa ggc atg gac gtg ctg gaa ttt ggt ggt   192
Gln Val Leu Asp Ala Leu Lys Gly Met Asp Val Leu Glu Phe Gly Gly
    50                  55                  60 att gag cca aac ccg gct tat gaa acg ctg atg aac gcc gtg aaa ctg   240
Ile Glu Pro Asn Pro Ala Tyr Glu Thr Leu Met Asn Ala Val Lys Leu
65                  70                  75                  80 gtt cgc gaa cag aaa gtg act ttc ctg ctg gcg gtt ggc ggt tct       288
Val Arg Glu Gln Lys Val Thr Phe Leu Leu Ala Val Gly Gly Gly Ser
                85                  90                  95 gta ctg gac ggc acc aaa ttt atc gcc gca gcg gct aac tat ccg gaa   336
Val Leu Asp Gly Thr Lys Phe Ile Ala Ala Ala Ala Asn Tyr Pro Glu
            100                 105                 110 aat atc gat ccg tgg cac att ctg caa acg ggc ggt aaa gag att aaa   384
Asn Ile Asp Pro Trp His Ile Leu Gln Thr Gly Gly Lys Glu Ile Lys
        115                 120                 125 agc gcc atc ccg atg ggc tgt gtg ctg acg ctg cca gca acc ggt tca   432
Ser Ala Ile Pro Met Gly Cys Val Leu Thr Leu Pro Ala Thr Gly Ser
    130                 135                 140 gaa tcc aac gca ggc gcg gtg atc tcc cgt aaa acc aca ggc gac aag   480
Glu Ser Asn Ala Gly Ala Val Ile Ser Arg Lys Thr Thr Gly Asp Lys
145                 150                 155                 160 cag gcg ttc cat tct gcc cat gtt cag ccg gta ttt gcc gtg ctc gat   528
Gln Ala Phe His Ser Ala His Val Gln Pro Val Phe Ala Val Leu Asp
                165                 170                 175 ccg gtt tat acc tac acc ctg ccg ccg cgt cag gtg gct aac ggc gta   576
Pro Val Tyr Thr Tyr Thr Leu Pro Pro Arg Gln Val Ala Asn Gly Val
            180                 185                 190 gtg gac gcc ttt gta cac acc gtg gaa cag tat gtt acc aaa ccg gtt   624
Val Asp Ala Phe Val His Thr Val Glu Gln Tyr Val Thr Lys Pro Val
        195                 200                 205 gat gcc aaa att cag gac cgt ttc gca gaa ggc att ttg ctg acg cta   672
Asp Ala Lys Ile Gln Asp Arg Phe Ala Glu Gly Ile Leu Leu Thr Leu
    210                 215                 220 atc gaa gat ggt ccg aaa gcc ctg aaa gag cca gaa aac tac gat gtg   720
Ile Glu Asp Gly Pro Lys Ala Leu Lys Glu Pro Glu Asn Tyr Asp Val
225                 230                 235                 240 cgc gcc aac gtc atg tgg gcg gcg act cag gcg ctg aac ggt ttg att   768
Arg Ala Asn Val Met Trp Ala Ala Thr Gln Ala Leu Asn Gly Leu Ile
                245                 250                 255 ggc gct ggc gta ccg cag gac tgg gca acg cat atg ctg ggc cac gaa   816
Gly Ala Gly Val Pro Gln Asp Trp Ala Thr His Met Leu Gly His Glu
            260                 265                 270 ctg act gcg atg cac ggt ctg gat cac gcg caa aca ctg gct atc gtc   864
Leu Thr Ala Met His Gly Leu Asp His Ala Gln Thr Leu Ala Ile Val
        275                 280                 285 ctg cct gca ctg tgg aat gaa aaa cgc gat acc aag cgc gct aag ctg   912
Leu Pro Ala Leu Trp Asn Glu Lys Arg Asp Thr Lys Arg Ala Lys Leu
    290                 295                 300 ctg caa tat gct gaa cgc gtc tgg aac atc act gaa ggt tcc gat gat   960
Leu Gln Tyr Ala Glu Arg Val Trp Asn Ile Thr Glu Gly Ser Asp Asp
305                 310                 315                 320
```

```
gag cgt att gac gcc gcg att gcc gca acc cgc aat ttc ttt gag caa      1008
Glu Arg Ile Asp Ala Ala Ile Ala Ala Thr Arg Asn Phe Phe Glu Gln
            325                 330                 335 tta ggc gtg ccg acc cac ctc tcc gac tac ggt ctg gac ggc agc tcc      1056
Leu Gly Val Pro Thr His Leu Ser Asp Tyr Gly Leu Asp Gly Ser Ser
        340                 345                 350 atc ccg gct ttg ctg aaa aaa ctg gaa gag cac ggc atg acc caa ctg      1104
Ile Pro Ala Leu Leu Lys Lys Leu Glu Glu His Gly Met Thr Gln Leu
    355                 360                 365 ggc gaa aat cat gac att acg ttg gat gtc agc cgc cgt ata tac gaa      1152
Gly Glu Asn His Asp Ile Thr Leu Asp Val Ser Arg Arg Ile Tyr Glu
370                 375                 380 gcc gcc cgc taa                                                      1164
Ala Ala Arg
385
```

<210> SEQ ID NO 14
<211> LENGTH: 387
<212> TYPE: PRT
<213> ORGANISM: Escherichia coli

<400> SEQUENCE: 14

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270
```

```
Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
        290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
                340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
370                 375                 380

Ala Ala Arg
385

<210> SEQ ID NO 15
<211> LENGTH: 1404
<212> TYPE: DNA
<213> ORGANISM: Escherichia coli
<220> FEATURE:
<221> NAME/KEY: CDS
<222> LOCATION: (1)..(1401)

<400> SEQUENCE: 15 atg aat caa cag gat att gaa cag gtg gtg aaa gcg gta ctg ctg aaa      48
Met Asn Gln Gln Asp Ile Glu Gln Val Val Lys Ala Val Leu Leu Lys
1               5                   10                  15 atg caa agc agt gac acg ccg tcc gcc gcc gtt cat gag atg ggc gtt      96
Met Gln Ser Ser Asp Thr Pro Ser Ala Ala Val His Glu Met Gly Val
                20                  25                  30 ttc gcg tcc ctg gat gac gcc gtt gcg gca gcc aaa gtc gcc cag caa     144
Phe Ala Ser Leu Asp Asp Ala Val Ala Ala Ala Lys Val Ala Gln Gln
            35                  40                  45 ggg tta aaa agc gtg gca atg cgc cag tta gcc att gct gcc att cgt     192
Gly Leu Lys Ser Val Ala Met Arg Gln Leu Ala Ile Ala Ala Ile Arg
        50                  55                  60 gaa gca ggc gaa aaa cac gcc aga gat tta gcg gaa ctt gcc gtc agt     240
Glu Ala Gly Glu Lys His Ala Arg Asp Leu Ala Glu Leu Ala Val Ser
65                  70                  75                  80 gaa acc ggc atg ggg cgc gtt gaa gat aaa ttt gca aaa aac gtc gct     288
Glu Thr Gly Met Gly Arg Val Glu Asp Lys Phe Ala Lys Asn Val Ala
                85                  90                  95 cag gcg cgc ggc aca cca ggc gtt gag tgc ctc tct ccg caa gtg ctg     336
Gln Ala Arg Gly Thr Pro Gly Val Glu Cys Leu Ser Pro Gln Val Leu
            100                 105                 110 act ggc gac aac ggc ctg acc cta att gaa aac gca ccc tgg ggc gtg     384
Thr Gly Asp Asn Gly Leu Thr Leu Ile Glu Asn Ala Pro Trp Gly Val
        115                 120                 125 gtg gct tcg gtg acg cct tcc act aac ccg gcg gca acc gta att aac     432
Val Ala Ser Val Thr Pro Ser Thr Asn Pro Ala Ala Thr Val Ile Asn
130                 135                 140 aac gcc atc agc ctg att gcc gcg ggc aac agc gtc att ttt gcc ccg     480
Asn Ala Ile Ser Leu Ile Ala Ala Gly Asn Ser Val Ile Phe Ala Pro
145                 150                 155                 160 cat ccg gcg gcg aaa aaa gtc tcc cag cgg gcg att acg ctg ctc aac     528
His Pro Ala Ala Lys Lys Val Ser Gln Arg Ala Ile Thr Leu Leu Asn
                165                 170                 175
```

```
cag gcg att gtt gcc gca ggt ggg ccg gaa aac tta ctg gtt act gtg       576
Gln Ala Ile Val Ala Ala Gly Gly Pro Glu Asn Leu Leu Val Thr Val
            180                 185                 190 gca aat ccg gat atc gaa acc gcg caa cgc ttg ttc aag ttt ccg ggt       624
Ala Asn Pro Asp Ile Glu Thr Ala Gln Arg Leu Phe Lys Phe Pro Gly
195                 200                 205 atc ggc ctg ctg gtg gta acc ggc ggc gaa gcg gta gta gaa gcg gcg       672
Ile Gly Leu Leu Val Val Thr Gly Gly Glu Ala Val Val Glu Ala Ala
210                 215                 220 cgt aaa cac acc aat aaa cgt ctg att gcc gca ggt gct ggc aac ccg       720
Arg Lys His Thr Asn Lys Arg Leu Ile Ala Ala Gly Ala Gly Asn Pro
225                 230                 235                 240 ccg gta gtg gtg gat gaa acc gcc gac ctc gcc cgt gcc gct cag tcc       768
Pro Val Val Val Asp Glu Thr Ala Asp Leu Ala Arg Ala Ala Gln Ser
                245                 250                 255 atc gtc aaa ggc gct tct ttc gat aac aac atc att tgt gcc gac gaa       816
Ile Val Lys Gly Ala Ser Phe Asp Asn Asn Ile Ile Cys Ala Asp Glu
            260                 265                 270 aag gta ctg att gtt gtt gat agc gta gcc gat gaa ctg atg cgt ctg       864
Lys Val Leu Ile Val Val Asp Ser Val Ala Asp Glu Leu Met Arg Leu
        275                 280                 285 atg gaa ggc cag cac gcg gtg aaa ctg acc gca gaa cag gcg cag cag       912
Met Glu Gly Gln His Ala Val Lys Leu Thr Ala Glu Gln Ala Gln Gln
        290                 295                 300 ctg caa ccg gtg ttg ctg aaa aat atc gac gag cgc gga aaa ggc acc       960
Leu Gln Pro Val Leu Leu Lys Asn Ile Asp Glu Arg Gly Lys Gly Thr
305                 310                 315                 320 gtc agc cgt gac tgg gtt ggt cgc gac gca ggc aaa atc gcg gcg gca      1008
Val Ser Arg Asp Trp Val Gly Arg Asp Ala Gly Lys Ile Ala Ala Ala
                325                 330                 335 atc ggc ctt aaa gtt ccg caa gaa acg cgc ctg ctg ttt gtg gaa acc      1056
Ile Gly Leu Lys Val Pro Gln Glu Thr Arg Leu Leu Phe Val Glu Thr
            340                 345                 350 acc gca gaa cat ccg ttt gcc gtg act gaa ctg atg atg ccg gtg ttg      1104
Thr Ala Glu His Pro Phe Ala Val Thr Glu Leu Met Met Pro Val Leu
        355                 360                 365 ccc gtc gtg cgc gtc gcc aac gtg gcg gat gcc att gcg cta gcg gtg      1152
Pro Val Val Arg Val Ala Asn Val Ala Asp Ala Ile Ala Leu Ala Val
370                 375                 380 aaa ctg gaa ggc ggt tgc cac cac acg gcg gca atg cac tcg cgc aac      1200
Lys Leu Glu Gly Gly Cys His His Thr Ala Ala Met His Ser Arg Asn
385                 390                 395                 400 atc gaa aac atg aac cag atg gcg aat gct att gat acc agc att ttc      1248
Ile Glu Asn Met Asn Gln Met Ala Asn Ala Ile Asp Thr Ser Ile Phe
                405                 410                 415 gtt aag aac gga ccg tgc att gcc ggg ctg ggg ctg ggc ggg gaa ggc      1296
Val Lys Asn Gly Pro Cys Ile Ala Gly Leu Gly Leu Gly Gly Glu Gly
            420                 425                 430 tgg acc acc atg acc atc acc acg cca acc ggt gaa ggg gta acc agc      1344
Trp Thr Thr Met Thr Ile Thr Thr Pro Thr Gly Glu Gly Val Thr Ser
        435                 440                 445 gcg cgt acg ttt gtc cgt ctg cgt cgc tgt gta tta gtc gat gcg ttt      1392
Ala Arg Thr Phe Val Arg Leu Arg Arg Cys Val Leu Val Asp Ala Phe
450                 455                 460 cgc att gtt taa                                                      1404
Arg Ile Val
465

<210> SEQ ID NO 16
```

```
<211> LENGTH: 467
<212> TYPE: PRT
<213> ORGANISM: Escherichia coli

<400> SEQUENCE: 16

Met Asn Gln Gln Asp Ile Glu Gln Val Val Lys Ala Val Leu Leu Lys
1               5                   10                  15

Met Gln Ser Ser Asp Thr Pro Ser Ala Ala Val His Glu Met Gly Val
            20                  25                  30

Phe Ala Ser Leu Asp Asp Ala Val Ala Ala Lys Val Ala Gln Gln
        35                  40                  45

Gly Leu Lys Ser Val Ala Met Arg Gln Leu Ala Ile Ala Ala Ile Arg
    50                  55                  60

Glu Ala Gly Glu Lys His Ala Arg Asp Leu Ala Glu Leu Ala Val Ser
65                  70                  75                  80

Glu Thr Gly Met Gly Arg Val Glu Asp Lys Phe Ala Lys Asn Val Ala
                85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
    130                 135                 140

Asn Ala Ile Ser Leu Ile Ala Ala Gly Asn Ser Val Ile Phe Ala Pro
145                 150                 155                 160

His Pro Ala Ala Lys Lys Val Ser Gln Arg Ala Ile Thr Leu Leu Asn
                165                 170                 175

Gln Ala Ile Val Ala Ala Gly Gly Pro Glu Asn Leu Leu Val Thr Val
            180                 185                 190

Ala Asn Pro Asp Ile Glu Thr Ala Gln Arg Leu Phe Lys Phe Pro Gly
        195                 200                 205

Ile Gly Leu Leu Val Val Thr Gly Gly Glu Ala Val Val Glu Ala Ala
    210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Ala Arg Ala Ala Gln Ser
                245                 250                 255

Ile Val Lys Gly Ala Ser Phe Asp Asn Asn Ile Ile Cys Ala Asp Glu
            260                 265                 270

Lys Val Leu Ile Val Val Asp Ser Val Ala Asp Glu Leu Met Arg Leu
        275                 280                 285

Met Glu Gly Gln His Ala Val Lys Leu Thr Ala Glu Gln Ala Gln Gln
    290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Lys Val Pro Gln Glu Thr Arg Leu Leu Phe Val Glu Thr
            340                 345                 350

Thr Ala Glu His Pro Phe Ala Val Thr Glu Leu Met Met Pro Val Leu
        355                 360                 365

Pro Val Val Arg Val Ala Asn Val Ala Asp Ala Ile Ala Leu Ala Val
    370                 375                 380

Lys Leu Glu Gly Gly Cys His His Thr Ala Ala Met His Ser Arg Asn
```

```
                385                 390                 395                 400
Ile Glu Asn Met Asn Gln Met Ala Asn Ala Ile Asp Thr Ser Ile Phe
                    405                 410                 415

Val Lys Asn Gly Pro Cys Ile Ala Gly Leu Gly Leu Gly Gly Glu Gly
                420                 425                 430

Trp Thr Thr Met Thr Ile Thr Thr Pro Thr Gly Glu Gly Val Thr Ser
                435                 440                 445

Ala Arg Thr Phe Val Arg Leu Arg Arg Cys Val Leu Val Asp Ala Phe
450                 455                 460

Arg Ile Val
465

<210> SEQ ID NO 17
<211> LENGTH: 1137
<212> TYPE: DNA
<213> ORGANISM: Bacillus subtilis
<220> FEATURE:
<221> NAME/KEY: CDS
<222> LOCATION: (1)..(1134)

<400> SEQUENCE: 17 atg atc ata ggg gtt cct aaa gag ata aaa aac aat gaa aac cgt gtc      48
Met Ile Ile Gly Val Pro Lys Glu Ile Lys Asn Asn Glu Asn Arg Val
1               5                   10                  15 gca tta aca ccc ggg ggc gtt tct cag ctc att tca aac ggc cac cgg      96
Ala Leu Thr Pro Gly Gly Val Ser Gln Leu Ile Ser Asn Gly His Arg
                20                  25                  30 gtg ctg gtt gaa aca ggc gcg ggc ctt gga agc gga ttt gaa aat gaa     144
Val Leu Val Glu Thr Gly Ala Gly Leu Gly Ser Gly Phe Glu Asn Glu
            35                  40                  45 gcc tat gag tca gca gga gcg gaa atc att gct gat ccg aag cag gtc     192
Ala Tyr Glu Ser Ala Gly Ala Glu Ile Ile Ala Asp Pro Lys Gln Val
        50                  55                  60 tgg gac gcc gaa atg gtc atg aaa gta aaa gaa ccg ctg ccg gaa gaa     240
Trp Asp Ala Glu Met Val Met Lys Val Lys Glu Pro Leu Pro Glu Glu
65                  70                  75                  80 tat gtt tat ttt cgc aaa gga ctt gtg ctg ttt acg tac ctt cat tta     288
Tyr Val Tyr Phe Arg Lys Gly Leu Val Leu Phe Thr Tyr Leu His Leu
                85                  90                  95 gca gct gag cct gag ctt gca cag gcc ttg aag gat aaa gga gta act     336
Ala Ala Glu Pro Glu Leu Ala Gln Ala Leu Lys Asp Lys Gly Val Thr
            100                 105                 110 gcc atc gca tat gaa acg gtc agt gaa ggc cgg aca ttg cct ctt ctg     384
Ala Ile Ala Tyr Glu Thr Val Ser Glu Gly Arg Thr Leu Pro Leu Leu
        115                 120                 125 acg cca atg tca gag gtt gcg ggc aga atg gca gcg caa atc ggc gct     432
Thr Pro Met Ser Glu Val Ala Gly Arg Met Ala Ala Gln Ile Gly Ala
130                 135                 140 caa ttc tta gaa aag cct aaa ggc gga aaa ggc att ctg ctt gcc ggg     480
Gln Phe Leu Glu Lys Pro Lys Gly Gly Lys Gly Ile Leu Leu Ala Gly
145                 150                 155                 160 gtg cct ggc gtt tcc cgc gga aaa gta aca att atc gga gga ggc gtt     528
Val Pro Gly Val Ser Arg Gly Lys Val Thr Ile Ile Gly Gly Gly Val
                165                 170                 175 gtc ggg aca aac gcg gcg aaa atg gct gtc ggc ctc ggt gca gat gtg     576
Val Gly Thr Asn Ala Ala Lys Met Ala Val Gly Leu Gly Ala Asp Val
            180                 185                 190 acg atc att gac tta aac gca gac cgc ttg cgc cag ctt gat gac atc     624
Thr Ile Ile Asp Leu Asn Ala Asp Arg Leu Arg Gln Leu Asp Asp Ile
        195                 200                 205
```

```
ttc ggc cat cag att aaa acg tta att tct aat ccg gtc aat att gct      672
Phe Gly His Gln Ile Lys Thr Leu Ile Ser Asn Pro Val Asn Ile Ala
    210                 215                 220 gat gct gtg gcg gaa gcg gat ctc ctc att tgc gcg gta tta att ccg      720
Asp Ala Val Ala Glu Ala Asp Leu Leu Ile Cys Ala Val Leu Ile Pro
225                 230                 235                 240 ggt gct aaa gct ccg act ctt gtc act gag gaa atg gta aaa caa atg      768
Gly Ala Lys Ala Pro Thr Leu Val Thr Glu Glu Met Val Lys Gln Met
                245                 250                 255 aaa ccc ggt tca gtt att gtt gat gta gcg atc gac caa ggc ggc atc      816
Lys Pro Gly Ser Val Ile Val Asp Val Ala Ile Asp Gln Gly Gly Ile
            260                 265                 270 gtc gaa act gtc gac cat atc aca aca cat gat cag cca aca tat gaa      864
Val Glu Thr Val Asp His Ile Thr Thr His Asp Gln Pro Thr Tyr Glu
        275                 280                 285 aaa cac ggg gtt gtg cat tat gct gta gcg aac atg cca ggc gca gtc      912
Lys His Gly Val Val His Tyr Ala Val Ala Asn Met Pro Gly Ala Val
    290                 295                 300 cct cgt aca tca aca atc gcc ctg act aac gtt act gtt cca tac gcg      960
Pro Arg Thr Ser Thr Ile Ala Leu Thr Asn Val Thr Val Pro Tyr Ala
305                 310                 315                 320 ctg caa atc gcg aac aaa ggg gca gta aaa gcg ctc gca gac aat acg     1008
Leu Gln Ile Ala Asn Lys Gly Ala Val Lys Ala Leu Ala Asp Asn Thr
                325                 330                 335 gca ctg aga gcg ggt tta aac acc gca aac gga cac gtg acc tat gaa     1056
Ala Leu Arg Ala Gly Leu Asn Thr Ala Asn Gly His Val Thr Tyr Glu
            340                 345                 350 gct gta gca aga gat cta ggc tat gag tat gtt cct gcc gag aaa gct     1104
Ala Val Ala Arg Asp Leu Gly Tyr Glu Tyr Val Pro Ala Glu Lys Ala
        355                 360                 365 tta cag gat gaa tca tct gtg gcg ggt gct taa                         1137
Leu Gln Asp Glu Ser Ser Val Ala Gly Ala
    370                 375
```

<210> SEQ ID NO 18
<211> LENGTH: 378
<212> TYPE: PRT
<213> ORGANISM: Bacillus subtilis

<400> SEQUENCE: 18

```
Met Ile Ile Gly Val Pro Lys Glu Ile Lys Asn Asn Glu Asn Arg Val
1               5                   10                  15

Ala Leu Thr Pro Gly Val Ser Gln Leu Ile Ser Asn Gly His Arg
            20                  25                  30

Val Leu Val Glu Thr Gly Ala Gly Leu Gly Ser Gly Phe Glu Asn Glu
        35                  40                  45

Ala Tyr Glu Ser Ala Gly Ala Glu Ile Ile Ala Asp Pro Lys Gln Val
    50                  55                  60

Trp Asp Ala Glu Met Val Met Lys Val Lys Glu Pro Leu Pro Glu Glu
65                  70                  75                  80

Tyr Val Tyr Phe Arg Lys Gly Leu Val Leu Phe Thr Tyr Leu His Leu
                85                  90                  95

Ala Ala Glu Pro Glu Leu Ala Gln Ala Leu Lys Asp Lys Gly Val Thr
            100                 105                 110

Ala Ile Ala Tyr Glu Thr Val Ser Glu Gly Arg Thr Leu Pro Leu Leu
        115                 120                 125

Thr Pro Met Ser Glu Val Ala Gly Arg Met Ala Ala Gln Ile Gly Ala
    130                 135                 140
```

Gln Phe Leu Glu Lys Pro Lys Gly Gly Lys Gly Ile Leu Leu Ala Gly
145                 150                 155                 160

Val Pro Gly Val Ser Arg Gly Lys Val Thr Ile Ile Gly Gly Gly Val
                165                 170                 175

Val Gly Thr Asn Ala Ala Lys Met Ala Val Gly Leu Gly Ala Asp Val
            180                 185                 190

Thr Ile Ile Asp Leu Asn Ala Asp Arg Leu Arg Gln Leu Asp Asp Ile
        195                 200                 205

Phe Gly His Gln Ile Lys Thr Leu Ile Ser Asn Pro Val Asn Ile Ala
    210                 215                 220

Asp Ala Val Ala Glu Ala Asp Leu Leu Ile Cys Ala Val Leu Ile Pro
225                 230                 235                 240

Gly Ala Lys Ala Pro Thr Leu Val Thr Glu Glu Met Val Lys Gln Met
                245                 250                 255

Lys Pro Gly Ser Val Ile Val Asp Val Ala Ile Asp Gln Gly Gly Ile
                260                 265                 270

Val Glu Thr Val Asp His Ile Thr Thr His Asp Gln Pro Thr Tyr Glu
            275                 280                 285

Lys His Gly Val Val His Tyr Ala Val Ala Asn Met Pro Gly Ala Val
    290                 295                 300

Pro Arg Thr Ser Thr Ile Ala Leu Thr Asn Val Thr Val Pro Tyr Ala
305                 310                 315                 320

Leu Gln Ile Ala Asn Lys Gly Ala Val Lys Ala Leu Ala Asp Asn Thr
                325                 330                 335

Ala Leu Arg Ala Gly Leu Asn Thr Ala Asn Gly His Val Thr Tyr Glu
            340                 345                 350

Ala Val Ala Arg Asp Leu Gly Tyr Glu Tyr Val Pro Ala Glu Lys Ala
        355                 360                 365

Leu Gln Asp Glu Ser Ser Val Ala Gly Ala
    370                 375

<210> SEQ ID NO 19
<211> LENGTH: 35
<212> TYPE: DNA
<213> ORGANISM: Artificial Sequence
<220> FEATURE:
<223> OTHER INFORMATION: Synthetic DNA Sequence

<400> SEQUENCE: 19
cacaggaaac agaccatgtt gccacccgaa acaca                                35

<210> SEQ ID NO 20
<211> LENGTH: 40
<212> TYPE: DNA
<213> ORGANISM: Artificial Sequence
<220> FEATURE:
<223> OTHER INFORMATION: Synthetic DNA Sequence

<400> SEQUENCE: 20
gttaatttct cctctttaat ttagaaaaat tcgatatagc                           40

<210> SEQ ID NO 21
<211> LENGTH: 40
<212> TYPE: DNA
<213> ORGANISM: Artificial Sequence
<220> FEATURE:
<223> OTHER INFORMATION: Synthetic DNA Sequence

<400> SEQUENCE: 21
ttaaagagga gaaattaacc atgagcgtca acaacccgca                    40

<210> SEQ ID NO 22
<211> LENGTH: 35
<212> TYPE: DNA
<213> ORGANISM: Artificial Sequence
<220> FEATURE:
<223> OTHER INFORMATION: Synthetic DNA Sequence

<400> SEQUENCE: 22
gagctcgaat tccatttatt gaatcgcctc aaggg                         35

<210> SEQ ID NO 23
<211> LENGTH: 36
<212> TYPE: DNA
<213> ORGANISM: Artificial Sequence
<220> FEATURE:
<223> OTHER INFORMATION: Synthetic DNA Sequence

<400> SEQUENCE: 23
agaggagaaa ttaaccatga acatgcccga aactgg                        36

<210> SEQ ID NO 24
<211> LENGTH: 37
<212> TYPE: DNA
<213> ORGANISM: Artificial Sequence
<220> FEATURE:
<223> OTHER INFORMATION: Synthetic DNA Sequence

<400> SEQUENCE: 24
gagctcgaat tccatttagt cgatcaggtt cagggtt                       37

<210> SEQ ID NO 25
<211> LENGTH: 36
<212> TYPE: DNA
<213> ORGANISM: Artificial Sequence
<220> FEATURE:
<223> OTHER INFORMATION: Synthetic DNA Sequence

<400> SEQUENCE: 25
agaggagaaa ttaaccatga ccagcaacaa cccgca                        36

<210> SEQ ID NO 26
<211> LENGTH: 35
<212> TYPE: DNA
<213> ORGANISM: Artificial Sequence
<220> FEATURE:
<223> OTHER INFORMATION: Synthetic DNA Sequence

<400> SEQUENCE: 26
gagctcgaat tccatttagc cctgcaacgc actca                         35

<210> SEQ ID NO 27
<211> LENGTH: 36
<212> TYPE: DNA
<213> ORGANISM: Artificial Sequence
<220> FEATURE:
<223> OTHER INFORMATION: Synthetic DNA Sequence

<400> SEQUENCE: 27
agaggagaaa ttaaccatga acatgcccga aaacgc                        36

<210> SEQ ID NO 28
<211> LENGTH: 37
<212> TYPE: DNA

```
<213> ORGANISM: Artificial Sequence
<220> FEATURE:
<223> OTHER INFORMATION: Synthetic DNA Sequence

<400> SEQUENCE: 28
gagctcgaat tccatttagt cgatcttgtt cagcact                              37

<210> SEQ ID NO 29
<211> LENGTH: 20
<212> TYPE: DNA
<213> ORGANISM: Artificial Sequence
<220> FEATURE:
<223> OTHER INFORMATION: Synthetic DNA Sequence

<400> SEQUENCE: 29
acggaagatc acttcgcaga                                                 20

<210> SEQ ID NO 30
<211> LENGTH: 26
<212> TYPE: DNA
<213> ORGANISM: Artificial Sequence
<220> FEATURE:
<223> OTHER INFORMATION: Synthetic DNA Sequence

<400> SEQUENCE: 30
gtcgaccaac gcgcggggag aggcgg                                          26

<210> SEQ ID NO 31
<211> LENGTH: 26
<212> TYPE: DNA
<213> ORGANISM: Artificial Sequence
<220> FEATURE:
<223> OTHER INFORMATION: Synthetic DNA Sequence

<400> SEQUENCE: 31
cagctggacc agttgcaatc caaacg                                          26

<210> SEQ ID NO 32
<211> LENGTH: 20
<212> TYPE: DNA
<213> ORGANISM: Artificial Sequence
<220> FEATURE:
<223> OTHER INFORMATION: Synthetic DNA Sequence

<400> SEQUENCE: 32
cggttagcca tttgcctgct                                                 20

<210> SEQ ID NO 33
<211> LENGTH: 20
<212> TYPE: DNA
<213> ORGANISM: Artificial Sequence
<220> FEATURE:
<223> OTHER INFORMATION: Synthetic DNA Sequence

<400> SEQUENCE: 33
ggatgaacta cgaggaaggg                                                 20

<210> SEQ ID NO 34
<211> LENGTH: 20
<212> TYPE: DNA
<213> ORGANISM: Artificial Sequence
<220> FEATURE:
<223> OTHER INFORMATION: Synthetic DNA Sequence

<400> SEQUENCE: 34
agttagtacc tccttatgaa                                                 20
```

<210> SEQ ID NO 35
<211> LENGTH: 20
<212> TYPE: DNA
<213> ORGANISM: Artificial Sequence
<220> FEATURE:
<223> OTHER INFORMATION: Synthetic DNA Sequence

<400> SEQUENCE: 35
ctggcacagc ttcctgctaa                                           20

<210> SEQ ID NO 36
<211> LENGTH: 40
<212> TYPE: DNA
<213> ORGANISM: Artificial Sequence
<220> FEATURE:
<223> OTHER INFORMATION: Synthetic DNA Sequence

<400> SEQUENCE: 36
tctgcgaagt gatcttccgt tacttgctcc ctttgctggg                     40

<210> SEQ ID NO 37
<211> LENGTH: 40
<212> TYPE: DNA
<213> ORGANISM: Artificial Sequence
<220> FEATURE:
<223> OTHER INFORMATION: Synthetic DNA Sequence

<400> SEQUENCE: 37
agcaggcaaa tggctaaccg gctttttacg cctcaaactt                     40

<210> SEQ ID NO 38
<211> LENGTH: 20
<212> TYPE: DNA
<213> ORGANISM: Artificial Sequence
<220> FEATURE:
<223> OTHER INFORMATION: Synthetic DNA Sequence

<400> SEQUENCE: 38
cgaccatttt ccgccaccat                                           20

<210> SEQ ID NO 39
<211> LENGTH: 40
<212> TYPE: DNA
<213> ORGANISM: Artificial Sequence
<220> FEATURE:
<223> OTHER INFORMATION: Synthetic DNA Sequence

<400> SEQUENCE: 39
cccttcctcg tagttcatcc tacttgctcc ctttgctggg                     40

<210> SEQ ID NO 40
<211> LENGTH: 40
<212> TYPE: DNA
<213> ORGANISM: Artificial Sequence
<220> FEATURE:
<223> OTHER INFORMATION: Synthetic DNA Sequence

<400> SEQUENCE: 40
ttcataagga ggtactaact atgatcatag gggttcctaa                     40

<210> SEQ ID NO 41
<211> LENGTH: 39
<212> TYPE: DNA
<213> ORGANISM: Artificial Sequence
<220> FEATURE:

<223> OTHER INFORMATION: Synthetic DNA Sequence

<400> SEQUENCE: 41
aagtttgagg cgtaaaaagc ttaagcaccc gccacagat                             39

<210> SEQ ID NO 42
<211> LENGTH: 39
<212> TYPE: DNA
<213> ORGANISM: Artificial Sequence
<220> FEATURE:
<223> OTHER INFORMATION: Synthetic DNA Sequence

<400> SEQUENCE: 42
atctgtggcg ggtgcttaag cttttttacgc ctcaaactt                            39

<210> SEQ ID NO 43
<211> LENGTH: 20
<212> TYPE: DNA
<213> ORGANISM: Artificial Sequence
<220> FEATURE:
<223> OTHER INFORMATION: Synthetic DNA Sequence

<400> SEQUENCE: 43
gcaatagcca caaagaaacc                                                  20

<210> SEQ ID NO 44
<211> LENGTH: 40
<212> TYPE: DNA
<213> ORGANISM: Artificial Sequence
<220> FEATURE:
<223> OTHER INFORMATION: Synthetic DNA Sequence

<400> SEQUENCE: 44
tctgcgaagt gatcttccgt aatgctctcc tgataatgtt                            40

<210> SEQ ID NO 45
<211> LENGTH: 40
<212> TYPE: DNA
<213> ORGANISM: Artificial Sequence
<220> FEATURE:
<223> OTHER INFORMATION: Synthetic DNA Sequence

<400> SEQUENCE: 45
agcaggcaaa tggctaaccg cagtagcgct gtctggcaac                            40

<210> SEQ ID NO 46
<211> LENGTH: 20
<212> TYPE: DNA
<213> ORGANISM: Artificial Sequence
<220> FEATURE:
<223> OTHER INFORMATION: Synthetic DNA Sequence

<400> SEQUENCE: 46
ggcagccaat acttactggc                                                  20

<210> SEQ ID NO 47
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 47
cccttcctcg tagttcatcc aatgctctcc tgataatgtt                            40

```
<210> SEQ ID NO 48
<211> LENGTH: 40
<212> TYPE: DNA
<213> ORGANISM: Artificial Sequence
<220> FEATURE:
<223> OTHER INFORMATION: Synthetic DNA Sequence

<400> SEQUENCE: 48
ttcataagga ggtactaact atgaatcaac aggatattga                         40

<210> SEQ ID NO 49
<211> LENGTH: 40
<212> TYPE: DNA
<213> ORGANISM: Artificial Sequence
<220> FEATURE:
<223> OTHER INFORMATION: Synthetic DNA Sequence

<400> SEQUENCE: 49
gttgccagac agcgctactg ttaaacaatg cgaaacgcat                         40

<210> SEQ ID NO 50
<211> LENGTH: 40
<212> TYPE: DNA
<213> ORGANISM: Artificial Sequence
<220> FEATURE:
<223> OTHER INFORMATION: Synthetic DNA Sequence

<400> SEQUENCE: 50
atgcgtttcg cattgtttaa cagtagcgct gtctggcaac                         40
```

METHOD FOR PRODUCING THEANINE

CROSS-REFERENCE TO RELATED APPLICATIONS

This patent application is the U.S. national phase of International Patent Application No. PCT/JP2018/015372, filed Apr. 12, 2018, which claims the benefit of Japanese Patent Application No. 2017-079893, filed Apr. 13, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 109,500 bytes ASCII (Text) file named "746101Sequence-Listing.txt," created Oct. 7, 2019.

TECHNICAL FIELD

The present invention relates to a microorganism that produces theanine and a method for efficiently producing theanine without exogenously adding ethylamine and without accumulation or leftover of ethylamine as a byproduct using the microorganism.

BACKGROUND ART

Theanine is a type of amino acid contained in tea, known as a main component of umami, and a substance that is important as a flavor component in foods (Patent Document 1). Moreover, in recent years, theanine has been found to have various physiological effects such as relaxing effect, suppressive effect on excitement caused by caffeine, and antihypertensive effect, and the demand as a food additive is growing.

As methods for producing theanine, a method involving treatment of glutamine and ethylamine with a glutaminase obtained from bacteria in the genus *Pseudomonas* (Patent Document 2), a method involving treatment of glutamine and an ethylamine derivative with a glutaminase or a glutaminase-producing microbe (Patent Document 3), a method involving treatment of glutamic acid and ethylamine in the presence of ATP with a γ-glutamylmethylamide synthetase that a methylotrophic *bacterium* has (Patent Document 1), and the like are disclosed, but these methods require addition of ethylamine as a reaction substrate in the production process. However, ethylamine has a very low boiling point, and therefore volatilization of ethylamine during production is unavoidable and volatilized ethylamine may adversely affect neighboring environment and the body of workers. Moreover, for example, special facilities are required to react ethylamine at a temperature equal to or more than the boiling point for the purpose of improving the reaction efficiency, and therefore the above methods have problems in terms of safety and cost (Patent Document 1). Thus, a method for producing theanine without exogenously adding ethylamine as a substrate and without accumulation or leftover of ethylamine as a byproduct is desired.

Proteins comprising an amino acid sequence set forth in SEQ ID NO: 2, 4, 6, or 8 (respectively corresponding to PP_5182, PP_0596, JM49_01725, and RFLU_RS03325 in FIG. 1 and FIG. 2) described below are proteins that bacteria in the genus *Pseudomonas* have, and all of them are registered as aminotransferase on database (NCBI Reference Sequence ACCESSION NOs.: NP_747283, NP_742759, and WP_012722053, GenBank ACCESSION NO.: AIS10430). However, there has been neither experimental examination of whether these proteins actually function as aminotransferase nor knowledge on their substrates and chemical reaction that they catalyze.

RELATED ART

Patent Document

Patent Document 1: Japanese Unexamined Patent Publication No. 2009-225705
Patent Document 2: Japanese Unexamined Patent Publication No. H05-68578
Patent Document 3: Japanese Unexamined Patent Publication No. H11-225789

DISCLOSURE OF INVENTION

Problems to Be Solved by the Invention

As described above, the existing methods for producing theanine using ethylamine had problems in terms of safety and cost.

Accordingly, an object of the present invention is to provide a method for efficiently producing theanine without exogenously adding ethylamine.

Means for Solving the Problems

The present invention relates to the following (1) to (10).
(1) A microorganism producing acetaldehyde, alanine, glutamic acid, and ATP from a carbon source and having enhanced activity of a protein of any one of the following [1] to [3] and enhanced γ-glutamylmethylamide synthetase activity compared to those of a parent strain:
[1] a protein comprising an amino acid sequence set forth in SEQ ID NO: 2, 4, 6, or 8;
[2] a mutant protein comprising an amino acid sequence modified from an amino acid sequence set forth in SEQ ID NO: 2, 4, 6, or 8 by deletion, substitution, insertion, or addition of 1 to 20 amino acids, and having activity to produce ethylamine with acetaldehyde and alanine as substrates (hereinafter, referred to as ethylamine-producing activity); and
[3] a homologous protein comprising an amino acid sequence having 95% or more identity with an amino acid sequence set forth in SEQ ID NO: 2, 4, 6, or 8, and having ethylamine-producing activity.
(2) A microorganism producing acetaldehyde, alanine, and glutamine from a carbon source and having enhanced activity of a protein of any one of [1] to [3] in the above (1) and enhanced glutaminase activity compared to those of a parent strain.
(3) A method for producing theanine, comprising: providing a protein of any one of [1] to [3] in the above (1) and γ-glutamylmethylamide synthetase together in an aqueous medium comprising acetaldehyde, alanine, glutamic acid, and ATP to produce and accumulate theanine in the aqueous medium; and collecting theanine from the aqueous medium.
(4) A method for producing theanine, comprising: providing a protein of any one of [1] to [3] in the above (1) and glutaminase together in an aqueous medium comprising acetaldehyde, alanine, and glutamine to produce and accumulate theanine in the aqueous medium; and collecting theanine from the aqueous medium.
(5) A method for producing theanine, comprising: culturing a microorganism of the above (1) or (2) in a culture medium to produce and accumulate theanine in a culture; and collecting theanine from the culture.
(6) A method for producing theanine, comprising: providing a culture of the microorganism of the above (1) or a processed product of the culture, acetaldehyde, alanine, glutamic acid, and ATP together in an aqueous medium to produce and accumulate theanine in the aqueous medium; and collecting theanine from the aqueous medium.
(7) A method for producing theanine, comprising: providing a culture of the microorganism of the above (2) or a processed product of the culture, acetaldehyde, alanine, and glutamine together in an aqueous medium to produce and accumulate theanine in the aqueous medium; and collecting theanine from the aqueous medium.
(8) The microorganism of the above (1) or (2), wherein the microorganism is a microorganism belonging to the genus *Escherichia* or the genus *Corynebacterium*.
(9) The method for producing theanine of any one of the above (5) to (7), wherein the microorganism is a microorganism belonging to the genus *Escherichia* or the genus *Corynebacterium*.
(10) The microorganism of the above (1) or (2), wherein the carbon source is sugar.

Effects of the Invention

The present invention provides a microorganism producing theanine and a method for efficiently producing theanine without exogenously adding ethylamine and without accumulation or leftover of ethylamine as a byproduct using the microorganism.

EMBODIMENTS FOR CARRYING OUT THE INVENTION

Figure 1:
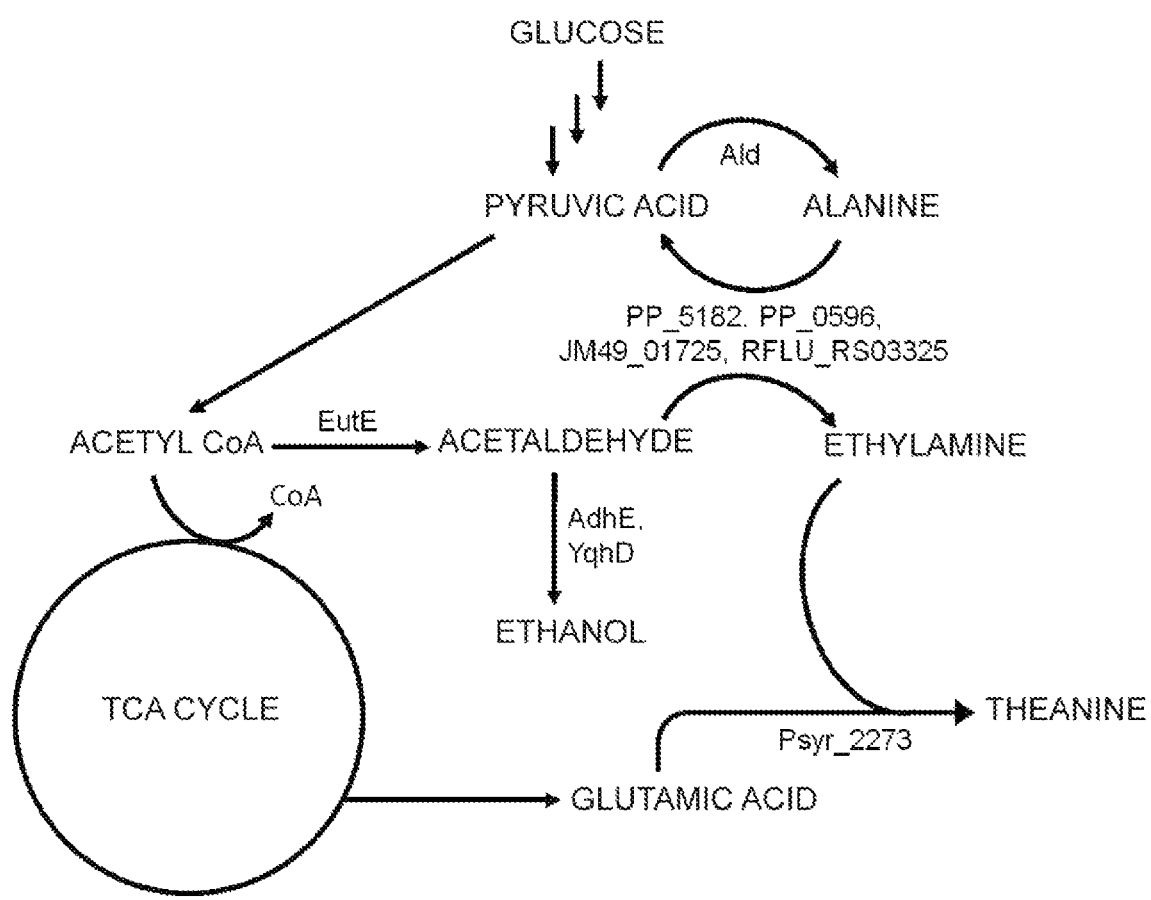
FIG. 1 shows a schematic view of a hypothetical metabolic pathway in a microorganism in a method for producing theanine by fermentation using γ-glutamylmethylamide synthetase. AdhE: alcohol dehydrogenase, YqhD: aldehyde reductase, EutE: aldehyde dehydrogenase, Ald: L-alanine dehydrogenase, Psyr_2273: γ-glutamylmethylamide synthetase, PP_5182, PP_0596, JM49_01725, and RFLU_RS03325: proteins having ethylamine-producing activity, TCA cycle: citric acid cycle.
Figure 2:
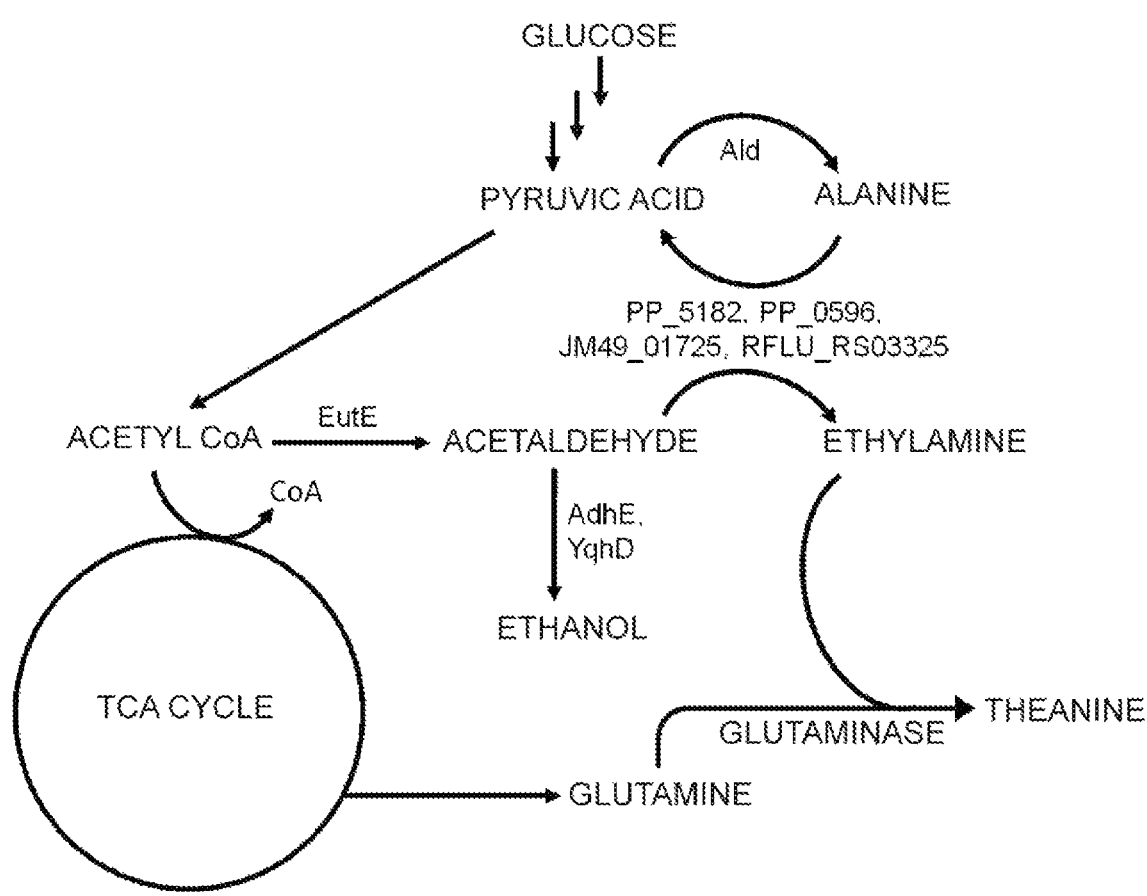
FIG. 2 shows a schematic view of a hypothetical metabolic pathway in a microorganism in a method for producing theanine by fermentation using glutaminase. AdhE: alcohol dehydrogenase, YqhD: aldehyde reductase, EutE: aldehyde dehydrogenase, Ald: L-alanine dehydrogenase, PP_5182, PP_0596, JM49_01725, and RFLU_RS03325: proteins having ethylamine-producing activity, TCA cycle: citric acid cycle.

1. Microorganism of the Present Invention and Method for Creating the Microorganism
1-1. Microorganism Having Enhanced Ethylamine-Producing Activity and γ-glutamylmethylamide Synthetase Activity and Method for Creating the Microorganism Microorganism Having Enhanced Ethylamine-Producing Activity The microorganism of the present invention is a microorganism producing acetaldehyde, alanine, glutamic acid, and ATP from a carbon source and having enhanced activity of a protein of any one of the following [1] to [3] and enhanced γ-glutamylmethylamide synthetase activity:
[1] a protein having an amino acid sequence set forth in SEQ ID NO: 2, 4, 6, or 8;
[2] a mutant protein comprising an amino acid sequence modified from an amino acid sequence set forth in SEQ ID NO: 2, 4, 6, or 8 by deletion, substitution, insertion, or addition of 1 to 20, preferably 1 to 10, and most preferably 1 to 5 amino acids, and having activity to produce ethylamine with acetaldehyde and alanine as substrates (hereinafter, referred to as ethylamine-producing activity); and
[3] a homologous protein comprising an amino acid sequence having 95% or more, preferably 97% or more, more preferably 98% or more, and most preferably 99% or more identity with an amino acid sequence set forth in SEQ ID NO: 2, 4, 6, or 8, and having ethylamine-producing activity.

The "mutant protein" refers to a protein obtained by artificially deleting or substituting amino acid residues in an original protein or artificially inserting or adding amino acid residues into the protein.

The "homologous proteins" refer to a group of proteins that naturally occurring organisms have and that have the same protein as an evolutionary origin. The homologous proteins resemble each other in structure and function.

In the mutant protein, the deletion, substitution, insertion, or addition of amino acids may be deletion, substitution, insertion, or addition of 1 to 20 amino acids at any positions in the same sequence.

The amino acids that are deleted, substituted, inserted, or added may be natural or unnatural amino acids. Examples of the natural amino acids include L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, and L-cysteine.

Examples of amino acids that may be substituted with each other are illustrated below. Amino acids included in the same group may be substituted with each other.
Group A: leucine, isoleucine, norleucine, valine, norvaline, alanine, 2-aminobutanoic acid, methionine, o-methylserine, t-butylglycine, t-butylalanine, cyclohexylalanine;
Group B: aspartic acid, glutamic acid, isoaspartic acid, isoglutamic acid, 2-aminoadipic acid, 2-aminosuberic acid;
Group C: asparagine, glutamine
Group D: lysine, arginine, ornithine, 2,4-diaminobutanoic acid, 2,3-diaminopropionic acid;
Group E: proline, 3-hydroxyproline, 4-hydroxyproline;
Group F: serine, threonine, homoserine;
Group G: phenylalanine, tyrosine.

The identity of amino acid sequences or nucleotide sequences may be determined by using BLAST algorithm by Karlin and Altschul [Pro. Natl. Acad. Sci. USA, 90, 5873 (1993)], or FASTA [Methods Enzymol., 183, 63 (1990)]. Based on this BLAST algorithm, programs called BLASTN and BLASTX have been developed [J. Mol. Biol., 215, 403 (1990)]. When a nucleotide sequence is analyzed by using BLASTN based on BLAST, the parameters are set at, for example, Score=100, wordlength=12. Moreover, when an amino acid sequence is analyzed by using BLASTX based on BLAST, the parameters are set at, for example, score=50, wordlength=3. When BLAST and Gapped BLAST program are used, the default parameters of each program are used. Specific techniques for these methods of analysis are known.

Ethylamine-producing activity of the above mutant protein or homologous protein may be confirmed by constructing a recombinant DNA comprising a DNA encoding the protein by a method described below, transforming a microorganism having no ethylamine-producing activity, for example, *Escherichia coli* strain W3110 with the recombinant DNA, culturing the resultant microorganism, preparing a cell extract comprising the protein from the resultant culture, bringing the fraction in contact with an aqueous solution comprising acetaldehyde and alanine as substrates, and detecting ethylamine produced as a result by high performance liquid chromatography (HPLC) or gas chromatography.

(Specific Examples of Microorganism Having Enhanced Ethylamine-Producing Activity)

Examples of the microorganism having enhanced activity of the protein of any one of the above [1] to [3] include microorganisms having enhanced ethylamine-producing activity compared to that of a parent strain, obtained by transforming the parent strain with a recombinant DNA comprising a DNA of any one of the following [4] to [7]:
[4] a DNA encoding the protein of any one of the above [1] to [3];
[5] a DNA comprising a nucleotide sequence set forth in SEQ ID NO: 1, 3, 5, or 7;
[6] a DNA that hybridizes with a DNA comprising a nucleotide sequence complementary to a nucleotide sequence set forth in SEQ ID NO: 1, 3, 5, or 7 under stringent conditions, and encodes a homologous protein having ethylamine-producing activity;
[7] a DNA comprising a nucleotide sequence having at least 95% or more, preferably 97% or more, more preferably 98% or more, and most preferably 99% or more identity with a nucleotide sequence set forth in SEQ ID NO: 1, 3, 5, or 7, and encoding a homologous protein having ethylamine-producing activity.

In the above, the term "hybridize" refers to a process in which a DNA hybridizes with a DNA having a particular nucleotide sequence or a part of the DNA. Therefore, the nucleotide sequence of the DNA that hybridizes with the DNA having a particular nucleotide sequence or part of the DNA, may be a DNA having a length that is useful as a probe for Northern or Southern blot analysis or that allows for use as an oligonucleotide primer for PCR analysis. Examples of a DNA used as a probe include a DNA of at least 100 nucleotides or more, preferably 200 nucleotides or more, and more preferably 500 nucleotides or more, and examples of a DNA used as a primer include a DNA of at least 10 nucleotides or more and preferably 15 nucleotides or more.

Methods of DNA hybridization experiments are well known, and it is possible to determine hybridization conditions and perform experiments in accordance with a large number of standard textbooks besides, for example, Molecular Cloning, the fourth edition (Cold Spring Harbor Laboratory Press (2012)), Methods for General and Molecular Bacteriology (ASM Press (1994)), and Immunology methods manual (Academic press (1997)).

Moreover, the DNA that hybridizes under stringent conditions may also be obtained by following a manual attached to a commercially available hybridization kit. Examples of the commercially available hybridization kit include Random Primed DNA Labeling Kit (manufactured by Roche Diagnostics K.K.), with which probes are produced by random priming to perform hybridization under stringent conditions.

Examples of the above stringent conditions include conditions of incubating a filter on which a DNA is immobilized with a probe DNA in solution comprising 50% formamide, 5×SSC (750 mM sodium chloride, 75 mM sodium citrate), 50 mM sodium phosphate (pH 7.6), 5×Denhardt's solution, 10% dextran sulfate, and 20 µg/L denatured salmon sperm DNA at 42° C. overnight, and then washing the filter, for example, in a 0.2×SSC solution at about 65° C.

The aforementioned various conditions may also be set by adding or changing a blocking reagent used for reducing the background in hybridization experiments. The aforementioned addition of a blocking reagent may involve changing of the hybridization conditions for adapting the conditions.

Examples of the DNA that can hybridize under the aforementioned stringent conditions include, a DNA comprising nucleotide sequences having at least 95% or more, preferably 97% or more, more preferably 98% or more, and most preferably 99% or more identity with the nucleotide sequence set forth in SEQ ID NO: 1, 3, 5, or 7, as calculated using a program such as BLAST or FASTA described above based on the above parameters.

The recombinant DNA comprising a DNA of any one of the above [4] to [7] is, for example, a DNA that is capable of autonomous replication in a parent strain and has the DNA of any one of the above [4] to [7] incorporated into an expression vector comprising a promoter at the position where the DNA of any one of the above [4] to [7] can be transcribed.

A DNA that can be incorporated into a chromosome in a parent strain and comprises the DNA of any one of the above [4] to [7] is also a recombinant DNA comprising a DNA of any one of the above [4] to [7].

When the recombinant DNA is a DNA that can be incorporated into chromosomal DNA in a parent strain, it does not need to comprise any promoter.

The parent strain refers to an original strain that is to be a subject for genetic modification, transformation, and the like. The original strain to be a subject for transformation by gene transfer is also referred to as a host strain.

The parent strain may be any microorganism, and examples thereof preferably include a prokaryote or a yeast strain, more preferably include a prokaryote belonging to the genus *Escherichia*, the genus *Serratia*, the genus *Bacillus*, the genus *Brevibacterium*, the genus *Corynebacterium*, the genus *Microbacterium*, the genus *Pseudomonas*, or the like, or a yeast strain belonging to the genus *Saccharomyces*, the genus *Schizosaccharomyces*, the genus *Kluyveromyces*, the genus *Trichosporon*, the genus *Schwanniomyces*, the genus *Pichia*, the genus *Candida*, or the like, and most preferably include prokaryotes such as *Escherichia coli* BL21 codon plus, *Escherichia coli* XL1-Blue, *Escherichia coli* XL2-Blue (both manufactured by Agilent Technologies, Inc.), *Escherichia coli* BL21 (DE3) pLysS (manufactured by Merck Millipore Corporation), *Escherichia coli* DH5α, *Escherichia coli* HST08 Premium, *Escherichia coli* HST02, *Escherichia coli* HST04 dam-/dcm-, *Escherichia coli* JM109, *Escherichia coli* HB101, *Escherichia coli* CJ236, *Escherichia coli* BMH71-18 mutS, *Escherichia coli* MV1184, *Escherichia coli* TH2 (all manufactured by Takara Bio Inc.), *Escherichia coli* W, *Escherichia coli* EV1101, *Escherichia coli* DH1, *Escherichia coli* MC1000, *Escherichia coli* MG1655, *Escherichia coli* W1485, *Escherichia coli* No. 49, *Escherichia coli* W3110, *Escherichia coli*

NY49, *Serratia ficaria*, *Serratia fonticola*, *Serratia liquefaciens*, *Serratia marcescens*, *Bacillus subtilis*, *Bacillus amyloliquefaciens*, *Brevibacterium immariophilum* ATCC14068, *Brevibacterium saccharolyticum* ATCC14066, *Corynebacterium ammoniagenes*, *Corynebacterium glutamicum* ATCC13032, *Corynebacterium glutamicum* ATCC14067, *Corynebacterium glutamicum* ATCC13869, *Corynebacterium acetoacidophilum* ATCC13870, *Microbacterium ammoniaphilum* ATCC15354, *Pseudomonas* sp. D-0110, or the like; or a yeast strain such as *Saccharomyces cerevisiae*, *Schizosaccharomyces pombe*, *Kluyveromyces lactis*, *Trichosporon pullulans*, *Schwanniomyces alluvius*, *Pichia pastoris*, *Candida utilis*, or the like.

When a prokaryote such as a *bacterium* is used as the parent strain, the recombinant DNA that is capable of autonomous replication in a parent strain is preferably a recombinant DNA composed of a promoter, a ribosomal binding sequence, a DNA of any one of the above [4] to [7], and a transcription termination sequence. A gene that controls the promoter may be contained.

It is preferable to use a recombinant DNA in which the distance between the Shine-Dalgarno sequence, which is a ribosomal binding sequence, and the initiation codon is adjusted to be an appropriate distance (for example, 6 to 18 nucleotides).

Moreover, in the recombinant DNA capable of autonomous replication in a parent strain, transcription termination sequence is not necessarily required for the expression of the DNA, but it is preferable to place a transcription termination sequence right under the structural gene.

When a microorganism belonging to the genus *Escherichia* is used as a parent strain, examples of the expression vector include pColdI, pSTV28, pUC118 (all manufactured by Takara Bio Inc.), pET21a, pCDF-1b, pRSF-1b (all manufactured by Merck Millipore Corporation), pMAL-c2x (manufactured by New England Biolabs, Inc.), pGEX-4T-1, pTrc99A (both manufactured by GE Healthcare Bioscience Holding Limited), pTrcHis, pSE280 (both manufactured by Thermo Fisher Scientific), pGEMEX-1 (manufactured by Promega Corporation), pQE-30, pQE80L (both manufactured by QIAGEN), pET-3, pBluescript II SK (+), pBluescript II KS (−) (all manufactured by Agilent Technologies, Inc.), pKYP10 (Japanese Unexamined Patent Publication No. S58-110600), pKYP200 [Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pTrS30 [prepared from *Escherichia coli* JM109/pTrS30 (FERM BP-5407)], pTrS32 [prepared from *Escherichia coli* JM109/pTrS32 (FERM BP-5408)], pTK31 [APPLIED AND ENVIRONMENTAL MICROBIOLOGY, 2007, Vol. 73, No. 20, p. 6378-6385], pPAC31 (International Publication No. WO 98/12343), pUC19 [Gene, 33,103 (1985)], pPA1 (Japanese Unexamined Patent Publication No. S63-233798), and the like.

The promoter in the case of using the above expression vector may be any promoter as long it functions in cells of the microorganism belonging to the genus *Escherichia*, and, for example, promoters derived from *Escherichia coli*, phage, or the like, such as promoters of genes involved in the biosynthesis of amino acids such as trp promoter and ilv promoter, lac promoter, $P_L$ promoter, $P_R$ promoter, $P_{SE}$ promoter, and the like may be used. Moreover, promoters artificially designed and modified such as a promoter in which 2 tip promoters are linked in tandem, tac promoter, trc promoter, lacT7 promoter, and let I promoter may also be used.

When a coryneform *bacterium* such as a microorganism belonging to the genus *Corynebacterium*, the genus *Brevibacterium*, the genus *Microbacterium*, or the like as a parent strain, examples of the expression vector include pCG1 (Japanese Unexamined Patent Publication No. S57-134500), pCG2 (Japanese Unexamined Patent Publication No. S58-35197), pCG4 (Japanese Unexamined Patent Publication No. S57-183799), pCG11 (Japanese Unexamined Patent Publication No. S57-134500), pCG116, pCE54, pCB101 (for all, Japanese Unexamined Patent Publication No. S58-105999), pCE51, pCE52, pCE53 [for all, Molecular and General Genetics, 196, 175 (1984)], and the like.

The promoter in the case of using the above expression vector may be any promoter as long as it functions in cells of the coryneform *bacterium*, such as a microorganism belonging to the genus *Corynebacterium*, the genus *Brevibacterium*, or the genus *Microbacterium*, or the like, and, for example, P54-6 promoter [Appl. Microbiol. Biotechnol., 53, 674-679 (2000)] may be used.

When a yeast strain is used as the parent strain, examples of the expression vector include YEp13 (ATCC37115), YEp24 (ATCC37051), YCp50 (ATCC37419), pHS19, pHS15, and the like.

The promoter in the case of using the above expression vector may be any promoter as long as it functions in cells of the yeast strain, and examples thereof include promoters such as PHOS promoter, PGK promoter, GAP promoter, ADH promoter, gall promoter, gal 10 promoter, heat shock polypeptide promoter, MFα1 promoter, and CUP1 promoter.

The "microorganism having enhanced ethylamine-producing activity compared to that of a parent strain obtained by transforming the parent strain with the recombinant DNA" refers to 1) a microorganism in which the transcriptional level of the DNA or the production level of the protein encoded by the DNA is increased by introduction of the recombinant DNA as a plasmid capable of autonomous replication in the parent strain or by incorporation of the recombinant DNA into a chromosome of the parent strain, or 2) a microorganism in which the specific activity of a protein having ethylamine-producing activity is enhanced by producing the mutant protein of the above [2].

Increase in the transcriptional level of the DNA of any one of the above [4] to [7] or the production level of the protein encoded by the DNA may be confirmed, for example, by a method involving measuring the transcriptional level of the DNA by Northern blotting or the production level of the protein by Western blotting, and comparing it with that of the parent strain.

Enhancement of the specific activity of the protein having ethylamine-producing activity may be confirmed, for example, by a method involving: purifying the mutant protein from a transformant obtained by transforming the parent strain with a DNA encoding the mutant protein; providing the protein, acetaldehyde, and alanine in an aqueous medium; measuring the specific activity from the amount of ethylamine produced and accumulated in the aqueous medium and the amount of the protein; and comparing the specific activity with the specific activity of a non-mutated protein having ethylamine-producing activity measured in the same way.

(Method for Creating Microorganism Having Enhanced Ethylamine-Producing Activity)

A microorganism having enhanced ethylamine-producing activity compared to that of a parent strain obtained by transforming the parent strain with a recombinant DNA comprising a DNA of any one of the above [4] to [7] may be created by the following method.

The DNA encoding the protein of the above [1] among the DNAs of the above [4], and the DNA of the above [5] may be obtained, for example, by Southern hybridization of the chromosomal DNA library of a microorganism, preferably a microorganism in the genus *Pseudomonas* and more preferably a microorganism selected from the group consisting of *Pseudomonas putida* strain KT2440, *Pseudomonas chlororaphis*, and *Pseudomonas fluorescens* strain SSW, using a probe DNA that may be designed based on a nucleotide sequence set forth in SEQ ID NO: 1, 3, 5, or 7; or by PCR using a primer DNA that may be designed based on the nucleotide sequence and using the chromosomal DNA of the above microorganism as a template [PCR Protocols, Academic Press (1990)].

*Pseudomonas putida* strain KT2440, *Pseudomonas chlororaphis*, and *Pseudomonas fluorescens* strain SBW may be obtained from National Institute of Technology and Evaluation (Independent Administrative Institution) Biotechnology Center (NITE Biological Resource Center) or the American Type Culture Collection (ATCC).

The DNA encoding the homologous protein of the above [3] among the DNAs of the above [4], and the DNAs of the above [6] and [7] may be obtained, for example, by a method involving: searching a variety of genetic sequence databases for a nucleotide sequence having 95% or more, preferably 97% or more, more preferably 98% or more, and most preferably 99% or more identity with a nucleotide sequence set forth in SEQ ID NO: 1, 3, 5, or 7; or searching a variety of protein sequence databases for an amino acid sequence having 95% or more, preferably 97% or more, more preferably 98% or more, and most preferably 99% or more identity with an amino acid sequence set forth in SEQ ID NO: 2, 4, 6, or 8; and conducting Southern hybridization or PCR in the same way as the above method for obtaining the DNA, using a probe DNA or a primer DNA that may be designed based on the nucleotide sequence or amino acid sequence obtained by the search and using a microorganism having the DNA.

The DNA encoding the mutant protein of the above [2] among the DNAs of the above [4] may be obtained, for example, by conducting error-prone PCR or the like using a DNA comprising a nucleotide sequence set forth in SEQ ID NO: 1, 3, 5, or 7 as a template.

Moreover, the DNA of the above [2] may be obtained also by PCR using 1 set of PCR primers having a nucleotide sequence designed to introduce an intended mutation (deletion, substitution, insertion, or addition) at each 5' end [Gene, 77, 51 (1989)]. More specifically, PCR using the DNA as a template is first performed with a sense primer corresponding to the 5' end of the DNA and an antisense primer having a sequence complementary to the sequence of the mutation at the 5' end and corresponding to the sequence just before (5' side of) the mutation site to amplify Fragment A (a mutation is introduced at 3' end) from the 5' end to the mutation site of the DNA. Then, PCR using the DNA as a template is performed with a sense primer having the sequence of the mutation at 5' end and corresponding to the sequence just after (3' side of) the mutation site and an antisense primer corresponding to the 3' end of the DNA to amplify Fragment B from the mutation site to the 3' end of the DNA, having a mutation at the 5' end. By mixing these amplified fragments after purification and performing PCR without adding any template or primer, the sense strand of the amplified Fragment A and the antisense strand of the amplified Fragment B hybridize because they share the mutation site, and the PCR reaction progresses using the hybrid as a template and primer to amplify the mutant DNA.

The nucleotide sequence of the obtained DNA of any one of the above [4] to [7] may be determined by incorporating the DNA as it is or cut with an appropriate restriction enzyme into a vector by a conventional method, introducing the obtained recombinant DNA into a host cell, and then analyzing the DNA by a method of nucleotide sequence analysis usually used, for example, dideoxy method [Proc. Natl. Acad. Sci., USA, 74, 5463 (1977)] or with a nucleotide sequence analyzer such as 3700DNA analyzer (manufactured by Applied Biosystems).

Examples of the above host cell include *Escherichia coli* XL1-Blue, *Escherichia coli* XL2-Blue (both manufactured by Agilent Technologies, Inc.), *Escherichia coli* DH5α, *Escherichia coli* HST08 Premium, *Escherichia coli* HST02, *Escherichia coli* HST04 dam$^-$/dcm$^-$, *Escherichia coli* JM109, *Escherichia coli* HB101, *Escherichia coli* CJ236, *Escherichia coli* BMH71-18 mutS, *Escherichia coli* MV1184, *Escherichia coli* TH2 (all manufactured by Takara Bio Inc.), *Escherichia coli* DH1, *Escherichia coli* MC1000, *Escherichia coli* W1485, *Escherichia coli* No. 49, *Escherichia coli* W3110, *Escherichia coli* NY49, *Escherichia coli* MP347, *Escherichia coli* NM522, and the like.

Examples of the above vector include pBluescript II KS (+), pPCR-Script Amp SK (+) (both manufactured by Agilent Technologies, Inc.), pT7Blue (manufactured by Merck Millipore Corporation), pCRII (manufactured by Thermo Fisher Scientific), pCR-TRAP (manufactured by GenHunter Corporation), pDIRECT [Nucleic Acids Res., 18, 6069 (1990)], and the like.

Any method of introducing the recombinant DNA may be used as long as it is a method of introducing DNA into a host cell, and examples thereof include methods using the calcium ion [Proc. Natl. Acad. Sci., USA, 69, 2110 (1972)], the protoplast method (Japanese Unexamined Patent Publication No. S63-248394), electroporation [Nucleic Acids Res., 16, 6127 (1988)], and the like.

When the result of nucleotide sequencing indicates that the obtained DNA is a partial length, the full length DNA may be obtained by Southern hybridization or the like of a chromosomal DNA library using the partial length DNA as a probe.

Furthermore, the DNA of the purpose may also be prepared by chemical synthesis using a Model 8905 DNA synthesizer manufactured by Perseptive Biosystems, Inc. or the like, based on the determined DNA nucleotide sequence.

Here, the expression level of the protein encoded by the DNA may also be improved by substituting nucleotides to make the nucleotide sequence of the DNA composed of codons optimal for the expression in the host. The information on the codon usage in the parent strain used in the method of production of the present invention may be obtained from public databases.

By inserting the DNA fragment prepared as described above downstream of the promoter in an appropriate expression vector, a recombinant DNA that a microorganism used in the method of production of the present invention can be produced.

Examples of such a recombinant DNA include pTrc99A_Psyr_2273_PP_5182, pTrc99A_Psyr_2273 PP_0596, pTrc99A_Psyr_2273_JM49_01725, and pTrc99A_Psyr_2273_PFLU_RS03325 described below in Examples.

Examples of the method for introducing a recombinant DNA as a plasmid capable of autonomous replication in a parent strain include methods such as methods using calcium ion, the protoplast method, electroporation, and the like as described above.

Examples of the method for incorporating a recombinant DNA into a chromosome of a parent strain include homologous recombination. Examples of the homologous recombination include methods using plasmid for homologous recombination that may be constructed by ligating the DNA to a plasmid DNA having a drug-resistance gene and being incapable of autonomous replication in host cells in which the DNA is desired to be introduced. Moreover, examples of methods utilizing homologous recombination used frequently with *Escherichia coli* include methods for introducing a recombinant DNA utilizing a homologous recombination system of the lambda phage [Proc. Natl. Acad. Sci. USA, 97, 6641-6645 (2000)].

Furthermore, a microorganism in which a region of interest on chromosomal DNA of the parent strain is replaced with the recombinant DNA may be obtained using: a selection method which takes advantage of the fact that *Escherichia coli* becomes sucrose-sensitive by *Bacillus subtilis* levansucrase incorporated on a chromosome with the recombinant DNA; a selection method which takes advantage of the fact that *Escherichia coli* becomes streptomycin-sensitive by incorporating the wildtype rpsL gene into *Escherichia coli* having a streptomycin-resistance mutant rpsL gene [Mol. Microbiol., 55,137 (2005), Biosci. Biotechnol. Biochem., 71, 2905 (2007)]; or the like.

It may be confirmed that the microorganism created by the above method is a microorganism having enhanced ethylamine-producing activity compared to that of a parent strain by measuring the transcriptional level of the DNA of any one of the above [4] to [7] or the production level of the protein encoded by the DNA, by Northern blotting or Western blotting in accordance with the method described above or measuring the specific activity of the protein, and comparing it with that of the parent strain.

Examples of such a microorganism include the strain W3110/pTrc99A_Psyr_2273_PP_5182, the strain W3110/pTrc99A_Psyr_2273_PP_0596, the strain W3110/pTrc99A_Psyr_2273_JM49_01725, and the strain W3110/pTrc99A_Psyr_2273_PFLU_RS03325 described below in Examples.

Microorganism Having Enhanced γ-Glutamylmethylamide Synthetase Activity

The microorganism of the present invention is a microorganism having enhanced activity of a protein of any one of the above [1] to [3] as well as enhanced γ-glutamylmethylamide synthetase activity.

The γ-glutamylmethylamide synthetase activity refers to the activity that γ-glutamylmethylamide synthetase has and specifically refers to the activity to produce theanine from ethylamine, glutamic acid, and ATP as substrates.

The protein having γ-glutamylmethylamide synthetase activity may be any protein as long as it is a protein having the activity, and examples thereof include the γ-glutamylmethylamide synthetase that Methylovorus mays TGMS No. 9 strain disclosed in Japanese Unexamined Patent Publication No. 2009-225705 has or a protein of any one of the following [8] to [10]:

[8] a protein comprising an amino acid sequence set forth in SEQ ID NO: 10,
[9] a mutant protein comprising an amino acid sequence modified from the amino acid sequence set forth in SEQ ID NO: 10 by deletion, substitution, insertion, or addition of 1 to 20, preferably 1 to 10, and most preferably 1 to 5 amino acids and having γ-glutamylmethylamide synthetase activity,
[10] a homologous protein comprising an amino acid sequence having 95% or more, preferably 97% or more, more preferably 98% or more, and most preferably 99% or more identity with the amino acid sequence set forth in SEQ ID NO: 10, and having γ-glutamylmethylamide synthetase activity.

(Specific Example of Microorganism Having Enhanced γ-Glutamylmethylamide Synthetase Activity)

Examples of the microorganism having enhanced γ-glutamylmethylamide synthetase activity include microorganisms having enhanced γ-glutamylmethylamide synthetase activity compared to that of a parent strain, obtained by transforming the parent strain with a recombinant DNA comprising a DNA encoding the γ-glutamylmethylamide synthetase that the above Methylovorus mays TGMS No. 9 strain has or a DNA of any one of the following [11] to [14]:

[11] a DNA encoding a protein of any one of the above [8] to [10],
[12] a DNA comprising the nucleotide sequence set forth in SEQ ID NO: 9,
[13] a DNA that hybridizes with a DNA comprising a nucleotide sequence complementary to the nucleotide sequence set forth in SEQ ID NO: 9 under stringent conditions and encodes a homologous protein having γ-glutamylmethylamide synthetase activity,
[14] a DNA comprising a nucleotide sequence having at least 95% or more, preferably 97% or more, more preferably 98% or more, and most preferably 99% or more identity with the nucleotide sequence set forth in SEQ ID NO: 9 and encoding a homologous protein having γ-glutamylmethylamide synthetase activity.

The description about hybridization and stringent conditions is the same as described above.

Examples of the above DNA that can hybridize under the stringent conditions include a nucleotide sequence having at least 95% or more, preferably 97% or more, more preferably 98% or more, and most preferably 99% or more identity with the nucleotide sequence set forth in SEQ ID NO: 9, as calculated using a program such as BLAST and FASTA described above based on the above parameters.

The DNA encoding a protein having γ-glutamylmethylamide synthetase activity may be obtained, for example, by a method using Southern hybridization or PCR as described above using a probe DNA that may be designed based on the nucleotide sequence set forth in SEQ ID NO: 9 and genomic DNA from *Pseudomonas syringae* pv. *Syringae* strain B728a as a template.

The recombinant DNA having the DNA may be obtained in accordance with the same method as that described above.

(Method for Creating Microorganism Having Enhanced γ-Glutamylmethylamide Synthetase Activity)

The microorganism having enhanced γ-glutamylmethylamide synthetase compared to that of a parent strain, obtained by transforming the parent strain with the recombinant DNA may be created by the same method as that described above.

It may be confirmed that the microorganism created by the above method is a microorganism having enhanced γ-glutamylmethylamide synthetase activity compared to that of a parent strain by comparing the transcriptional level of a DNA encoding γ-glutamylmethylamide synthetase, the production level of the protein or the specific activity of the protein with that of the parent strain.

Increase in the transcriptional level of the DNA encoding the protein or the production level of the protein encoded by the DNA may be confirmed, for example, by a method involving measuring the transcriptional level of the DNA by Northern blotting or the production level of the protein by Western blotting and comparing it with that of the parent strain.

The specific activity of the protein may be confirmed, for example, by purifying the protein from a transformant obtained by transforming the parent strain with a DNA encoding the protein, providing the protein, ethylamine, glutamic acid, and ATP in an aqueous medium, and measuring the specific activity from the amounts of theanine produced and accumulated in the aqueous medium and the protein.

The above DNA that encodes a protein having ethylamine-producing activity and the DNA that encodes γ-glutamylmethylamide synthetase may be present on the same recombinant DNA or present on separate recombinant DNAs.

Moreover, the microorganism of the present invention preferably has decreased or eliminated theanine-degrading activity, in addition to having enhanced γ-glutamylmethylamide synthetase activity, from the viewpoint of suppressing the degradation of theanine produced. Specific examples of such a microorganism include a microorganism having decreased or eliminated γ-glutamyltranspeptidase activity.

Microorganism Producing Acetaldehyde, Alanine, Glutamic Acid, and ATP from Carbon Source The microorganism of the present invention is a microorganism producing acetaldehyde, alanine, glutamic acid, and ATP from a carbon source, and having enhanced activity of a protein of any one of the above [1] to [3] and enhanced γ-glutamylmethylamide synthetase activity compared to that of a parent strain.

The microorganism producing acetaldehyde, alanine, glutamic acid, and ATP from a carbon source refers to a microorganism producing acetaldehyde, alanine, glutamic acid, and ATP from a carbon source as a starting material in the microorganism when the microorganism is cultured in a culture medium by the method of 2-1 described below.

Such a microorganism is not limited as long as it is a microorganism producing acetaldehyde, alanine, glutamic acid, and ATP from a carbon source as a starting material.

Examples thereof include microorganisms having enhanced ethylamine-producing activity and γ-glutamylmethylamide synthetase activity obtained by using any parent strain. Moreover, examples thereof include the above microorganism having enhanced ethylamine-producing activity and γ-glutamylmethylamide synthetase activity created from a microorganism of any one of the following (A) to (D) as a parent strain, or microorganisms of any one of the following (A) to (D) created from the above microorganism having enhanced ethylamine-producing activity and γ-glutamylmethylamide synthetase activity as a parent strain:

(A) a microorganism having decreased or eliminated activity of at least one or more proteins selected from the group consisting of alcohol dehydrogenase (AdhE) and aldehyde reductase (YqhD) compared to that of the parent strain,
(B) a microorganism having enhanced activity of aldehyde dehydrogenase (EutE) compared to that of a parent strain,
(C) a microorganism having enhanced activity of L-alanine dehydrogenase (Ald) compared to that of a parent strain,
(D) a microorganism having any combination of traits of the microorganisms of the above (A) to (C).

From the viewpoint of increasing supplies of acetaldehyde and alanine, it is preferable that the microorganism of the present invention have a trait of the above (B) or (C), preferably the traits of (B) and (C).

In addition to that, it is more preferable that the microorganism of the present invention have the trait of the above (A) from the viewpoint of suppressing metabolism of acetaldehyde into ethanol.

(Microorganism Having Decreased or Eliminated Activity of at Least One or More Proteins Selected from Group Consisting of Alcohol Dehydrogenase (AdhE) and Aldehyde Reductase (YqhD))

Alcohol dehydrogenase refers to a protein having alcohol dehydrogenase activity. The alcohol dehydrogenase activity refers to an activity to reduce acetaldehyde into ethanol with nicotinamide adenine dinucleotide as a coenzyme.

Aldehyde reductase refers to a protein having aldehyde reductase activity. The aldehyde reductase activity refers to an activity to reduce acetaldehyde to ethanol with nicotinamide adenine dinucleotide phosphate as a coenzyme.

Examples of the microorganism having decreased or eliminated activity of at least one or more proteins selected from the group consisting of alcohol dehydrogenase and aldehyde reductase compared to that of a parent strain include microorganisms of the following (a) and (b), obtained by introducing deletion, substitution, insertion, or addition of nucleotides into the nucleotide sequence of a DNA encoding the non-mutated, wildtype protein present on chromosomal DNA:

(a) a microorganism having a specific activity of the protein decreased to 80% or less, preferably 50% or less, more preferably 30% or less, further preferably 20% or less, particularly preferably 10% or less, and most preferably 0% compared to that of the parent strain,
(b) a microorganism having a transcriptional level of the DNA or production level of the protein decreased to 80% or less, preferably 50% or less, more preferably 30% or less, further preferably 20% or less, particularly preferably 10% or less, and most preferably 0% compared to that of the parent strain.

More preferably, examples thereof include a microorganism having deletion of a part or all of the DNA.

The DNA encoding alcohol dehydrogenase may be any DNA as long as it is a DNA encoding a protein having alcohol dehydrogenase activity that the parent strain has, and examples thereof include a DNA of any one of the following [15] to [18]:

[15] a DNA encoding a protein comprising the amino acid sequence set forth in SEQ ID NO: 12,
[16] a DNA encoding a homologous protein comprising an amino acid sequence having 95% or more, preferably 97% or more, more preferably 98% or more, and most preferably 99% or more identity with the amino acid sequence set forth in SEQ ID NO: 12, and having alcohol dehydrogenase activity,
[17] a DNA comprising the nucleotide sequence set forth in SEQ ID NO: 11,
[18] a DNA comprising a nucleotide sequence having at least 95% or more, preferably 97% or more, more preferably 98% or more, and most preferably 99% or more identity with the nucleotide sequence set forth in SEQ ID NO: 11, and encoding a homologous protein having alcohol dehydrogenase activity.

The DNA encoding aldehyde reductase may be any DNA as long as it is a DNA encoding a protein having aldehyde reductase activity that the parent strain has, and examples thereof include a DNA of any one of the following [19] to [22]:

[19] a DNA encoding a protein comprising the amino acid sequence set forth in SEQ ID NO: 14,

[20] a DNA encoding a homologous protein comprising an amino acid sequence having 95% or more, preferably 97% or more, more preferably 98% or more, and most preferably 99% or more identity with the amino acid sequence set forth in SEQ ID NO: 14, and having aldehyde reductase activity,

[21] a DNA comprising the nucleotide sequence set forth in SEQ ID NO: 13,

[22] a DNA comprising a nucleotide sequence having at least 95% or more, preferably 97% or more, more preferably 98% or more, and most preferably 99% or more identity with the nucleotide sequence set forth in SEQ ID NO: 13, and encoding a homologous protein having aldehyde reductase activity.

The microorganism having decreased or eliminated activity of at least one or more proteins selected from the group consisting of alcohol dehydrogenase and aldehyde reductase compared to that of a parent strain may be obtained, for example, using the above microorganism which has enhanced ethylamine-producing activity and γ-glutamylmethylamide synthetase activity as a parent strain, by decreasing or eliminating activity of at least one or more proteins selected from the group consisting of alcohol dehydrogenase and aldehyde reductase in the parent strain, in accordance with a usual method of mutation, gene replacement by a recombinant DNA technique, or the like.

Examples of the mutation method include a method using N-methyl-N'-nitro-N-nitrosoguanidine (NTG) (Microbiology Laboratory Manual (in Japanese), 1986, page 131, Kodansha Scientific Ltd.), ultraviolet irradiation, and the like.

Examples of the gene replacement by a recombinant DNA technique include: a method involving introducing a mutation into the DNA encoding at least one or more proteins selected from the group consisting of alcohol dehydrogenase and aldehyde reductase by in vitro mutagenesis using a mutagen, or by error-prone PCR or the like, and then replacing a DNA encoding the protein present on chromosomal DNA of the parent strain with the mutagenized DNA by using homologous recombination; a method involving introducing deletion, substitution, insertion, or addition of one or more nucleotides into a DNA encoding at least one or more proteins selected from the group consisting of alcohol dehydrogenase and aldehyde reductase, and then replacing a DNA encoding the protein present on chromosomal DNA of the parent strain with the modified DNA using homologous recombination; or the like.

The DNAs encoding alcohol dehydrogenase and aldehyde reductase may be obtained, for example, by a method using Southern hybridization or PCR as described above using probe DNAs that may be designed based on a nucleotide sequence set forth in SEQ ID NO: 11 and 13, respectively, and using, for example, genomic DNA of *Escherichia coli* strain W3110 as a template.

The method for introducing deletion, substitution, insertion, or addition of one or more nucleotides into a DNA encoding at least one or more proteins selected from the group consisting of alcohol dehydrogenase and aldehyde reductase, and the method for replacing the region of interest on chromosomal DNA of the parent strain by homologous recombination or the like with the DNA prepared by the above method, are the same as described above.

It may be confirmed that a microorganism is a microorganism having decreased or eliminated activity of at least one or more proteins selected from the group consisting of alcohol dehydrogenase and aldehyde reductase compared to that of a parent strain, for example, by culturing the parent strain and the microorganism in a culture medium containing acetaldehyde, and comparing the ratios of ethanol in the culture liquid and in cells of the microorganisms.

It may be confirmed that a microorganism is a microorganism having decreased or eliminated transcriptional level of DNA encoding at least one or more proteins selected from the group consisting of alcohol dehydrogenase and aldehyde reductase or production level of the protein compared to that of a parent strain, for example, by measuring the transcriptional level of the gene in the microorganism by Northern blotting or the production level of the protein in the microorganism by Western blotting, and comparing it with that of the parent strain.

Examples of the microorganism having decreased or eliminated transcriptional level of DNA encoding at least one or more proteins selected from the group consisting of alcohol dehydrogenase and aldehyde reductase or production level of the protein compared to that of a parent strain, include a microorganism having deletion of a part or all of the DNA encoding at least one or more proteins selected from the group consisting of alcohol dehydrogenase and aldehyde reductase. Specific examples thereof include the strain W3110A and strain W3110AE described below in Examples.

(Microorganism Having Enhanced Activity of Aldehyde Dehydrogenase (EutE))

Aldehyde dehydrogenase refers to a protein having aldehyde dehydrogenase activity. The aldehyde dehydrogenase activity refers to an activity to produce acetaldehyde with acetyl CoA as a substrate.

Examples of the microorganism having enhanced aldehyde dehydrogenase activity compared to that of a parent strain include microorganisms of the following (c) and (d):

(c) a microorganism that is obtained by modifying a DNA encoding a protein having aldehyde dehydrogenase activity on chromosomal DNA of the parent strain and
i) has enhanced specific activity of the protein compared to that of the parent strain, or
ii) has an increased transcriptional level of the DNA or production level of the protein compared to that of the parent strain;

(d) a microorganism that is obtained by transforming a microorganism of the parent strain with a recombinant DNA comprising a DNA encoding the protein and has an increased copy number of the DNA compared to that of the parent strain.

Examples of the microorganism of the above (c), that is obtained by modifying a DNA encoding a protein having aldehyde dehydrogenase activity on chromosomal DNA of the parent strain and i) has enhanced specific activity of the protein compared to that of the parent strain, include a microorganism having a protein having an amino acid sequence modified from the amino acid sequence of the protein having aldehyde dehydrogenase activity that the parent strain has by deletion, substitution, insertion, or addition of 1 to 20 amino acids, preferably 1 to 10 amino acids, and most preferably 1 to 5 amino acids, and thereby having a mutant protein having enhanced specific activity compared to that of the protein in the parent strain.

The microorganism of the above (c), that is obtained by modifying a DNA encoding a protein having aldehyde dehydrogenase activity on chromosomal DNA of the parent strain and i) has enhanced specific activity of the protein compared to that of the parent strain, may be obtained, for example, using the microorganism which has enhanced ethylamine-producing activity and γ-glutamylmethylamide synthetase activity as the parent strain, by enhancing the specific activity of the protein having aldehyde dehydrogenase activity in the above microorganism, in accordance with a usual method of mutation, gene replacement by a recombinant DNA technique, or the like.

Examples of the mutation method include the above methods.

Examples of the gene replacement by a recombinant DNA technique include the above methods.

The DNA encoding a protein having aldehyde dehydrogenase activity may be obtained, for example, by the above method using Southern hybridization or PCR using a probe DNA that may be designed based on the nucleotide sequence set forth in SEQ ID NO: 15, and using, for example, genomic DNA of *Escherichia coli* strain W3110 as a template.

It may be confirmed that a microorganism is a microorganism having enhanced specific activity of a protein having aldehyde dehydrogenase activity compared to that of a parent strain, for example, by purifying the mutant protein from a microorganism having the mutant protein; providing the mutant protein, acetyl-CoA, and other substrates in an aqueous medium; measuring the specific activity from the amounts of acetaldehyde produced and accumulated in the aqueous medium and the protein; and comparing the specific activity with the specific activity of the non-mutated protein having aldehyde dehydrogenase activity obtained from the parent strain measured in the same way.

Examples of the microorganism of the above (c), that is obtained by modifying a DNA encoding a protein having aldehyde dehydrogenase activity on chromosomal DNA of the parent strain and ii) has increased transcriptional level of the DNA or production level of the protein compared to that of a parent strain, include a microorganism having a promoter region modified from a nucleotide sequence of a transcriptional regulatory region or a promoter region of the DNA, encoding a protein having aldehyde dehydrogenase activity present on chromosomal DNA of the parent strain by deletion, substitution, insertion, or addition of 1 or more nucleotides, preferably 1 to 20 nucleotides, more preferably 1 to 10 nucleotides, and further preferably 1 to 5 nucleotides, and thereby having increased expression level of the DNA compared to that of the parent strain; or a microorganism having increased expression level of the DNA compared to that of the parent strain obtained by replacing a promoter region of the DNA present on chromosomal DNA of the parent strain with a known strong promoter sequence.

The microorganism of the above (c), that is obtained by modifying a DNA encoding a protein having aldehyde dehydrogenase activity on chromosomal DNA of the parent strain and ii) has increased transcriptional level of the DNA or production level of the protein compared to that of the parent strain, may be obtained, for example, using the microorganism which has enhanced ethylamine-producing activity and γ-glutamylmethylamide synthetase activity as a parent strain, by increasing the transcriptional level of the DNA for the protein having aldehyde dehydrogenase activity or the production level of the protein in the above microorganism, in accordance with a usual method of mutation, or gene replacement by a recombinant DNA technique, or the like.

Examples of the mutation method include the above methods.

Examples of the gene replacement by a recombinant DNA technique include a method involving introducing a mutation into the transcriptional regulatory region and the promoter region of the DNA encoding a protein having aldehyde dehydrogenase activity that the parent strain has, for example, a DNA having a nucleotide sequence 200 bp, preferably 100 bp, upstream of the initiation codon of the protein, by subjecting the DNA to the mutation treatment in vitro, error-prone PCR, or the like, and then replacing the DNA encoding a protein having aldehyde dehydrogenase activity present on chromosomal DNA of the parent strain with the mutant DNA using the above homologous recombination.

Moreover, a microorganism having increased production level of the protein having aldehyde dehydrogenase activity compared to that of a parent strain may also be obtained by replacing a promoter region of the DNA encoding a protein having aldehyde dehydrogenase activity in the parent strain with a known strong promoter sequence.

Examples of such a promoter include the above promoters.

It may be confirmed that the microorganism obtained by the above method is a microorganism having an increased transcriptional level of the DNA encoding a protein having aldehyde dehydrogenase activity or production level of the protein compared to that of a parent strain, for example, by measuring the transcriptional level of the DNA in the microorganism by Northern blotting or the production level of the protein in the microorganism by Western blotting, and comparing it with that of the parent strain.

Examples of the microorganism (d), that is obtained by transforming a microorganism of the parent strain with a recombinant DNA comprising the DNA encoding a protein having aldehyde dehydrogenase activity and has an increased copy number of the DNA compared to that of the parent strain, include a microorganism having an increased copy number of the DNA on chromosomal DNA, and a microorganism having the DNA out of chromosomal DNA as a plasmid DNA resulted from transforming a microorganism of the parent strain with the recombinant DNA comprising the DNA encoding a protein having aldehyde dehydrogenase activity.

The protein having aldehyde dehydrogenase activity may be any protein as long as it is a protein having the activity, and examples thereof include proteins of any one of the following [23] to [25]:

[23] a protein having the amino acid sequence set forth in SEQ ID NO: 16,

[24] a mutant protein comprising an amino acid sequence modified from the amino acid sequence set forth in SEQ ID NO: 16 by deletion, substitution, insertion, or addition of 1 to 20, preferably 1 to 10, and most preferably 1 to 5 amino acids and having aldehyde dehydrogenase activity,

[25] a homologous protein comprising an amino acid sequence having 95% or more, preferably 97% or more, more preferably 98% or more, and most preferably 99% or more identity with the amino acid sequence set forth in SEQ ID NO: 16 and having aldehyde dehydrogenase activity.

In the above description, a mutant protein comprising an amino acid sequence where 1 to 20, preferably 1 to 10, and most preferably 1 to 5 amino acid residues are deleted, substituted, inserted, or added and having aldehyde dehydrogenase activity may be obtained, for example, by introducing a mutation into DNA encoding a protein having the amino acid sequence set forth in SEQ ID NO: 16, using the above error-prone PCR or site-directed mutagenesis.

The deletion, substitution, insertion, or addition of 1 to 20, preferably 1 to 10, and most preferably 1 to 5 or more amino acids in the amino acid sequence set forth in SEQ ID NO: 16 may be deletion, substitution, or addition of one or more amino acid residues at any position(s) in the same sequence.

It may be confirmed that the above mutant protein or homologous protein is a protein having aldehyde dehydrogenase activity, for example, by producing a transformant expressing the protein to be confirmed on its activity using DNA recombination and culturing the transformant in a culture medium and measuring the amount of acetaldehyde in the culture.

The DNA encoding a protein having aldehyde dehydrogenase activity may be any DNA as long as it is a DNA encoding a protein having the activity, and examples thereof include a DNA of any one of the following [26] to [29]:

[26] a DNA encoding a protein of any one of the above [23] to [25],
[27] a DNA having the nucleotide sequence set forth in SEQ ID NO: 15,
[28] a DNA that hybridizes with a DNA comprising a nucleotide sequence complementary to the nucleotide sequence set forth in SEQ ID NO: 15 under stringent conditions, and encodes a homologous protein having aldehyde dehydrogenase activity,
[29] a DNA comprising a nucleotide sequence having at least 95% or more, preferably 97% or more, more preferably 98% or more, and most preferably 99% or more identity with the nucleotide sequence set forth in SEQ ID NO: 15, and encoding a homologous protein having aldehyde dehydrogenase activity.

The description about hybridization and stringent conditions is the same as described above.

Examples of the above DNA that can hybridize under stringent conditions include a DNA having at least 95% or more, preferably 97% or more, more preferably 98% or more, and most preferably 99% or more identity with the DNA comprising the nucleotide sequence set forth in SEQ ID NO: 15, as calculated using BLAST, FASTA, or the like described above based on the above parameters or the like.

The DNA encoding a protein having aldehyde dehydrogenase activity may be obtained, for example, by the above method using Southern hybridization or PCR using a probe DNA that may be designed based on the nucleotide sequence set forth in SEQ ID NO: 15 and using, for example, genomic DNA of *Escherichia coli* strain W3110 as a template.

The microorganism of the above (d), that is obtained by transforming a microorganism of the parent strain with the recombinant DNA comprising the DNA encoding a protein having aldehyde dehydrogenase activity and has an increased copy number of the gene encoding the protein compared to that of the parent strain, may be obtained by the following method.

Based on the DNA encoding a protein having aldehyde dehydrogenase activity obtained by the above method, a DNA fragment with an appropriate length comprising a part encoding the protein is prepared as needed. Also, a transformant having increased productivity may be obtained by substituting nucleotides to make the nucleotide sequence of the part encoding the protein composed of codons optimal for the expression in host cells.

By inserting the DNA fragment downstream of a promoter in an appropriate expression vector, a recombinant DNA capable of autonomous replication in a parent strain is constructed. By transforming the above microorganism having enhanced ethylamine-producing activity and γ-glutamylmethylamide synthetase activity with the recombinant DNA, a microorganism having an increased copy number of the DNA encoding the protein compared to that of the parent strain can be obtained.

Moreover, the microorganism having an increased copy number of the DNA encoding the protein compared to that of the parent strain may also be obtained, by transforming the parent strain with the recombinant DNA that comprises the prepared DNA fragment and can be incorporated into a chromosome to incorporate the DNA encoding aldehyde dehydrogenase at any position of the chromosomes. When the DNA is incorporated into a chromosome, the recombinant DNA may not comprise a promoter.

When a prokaryote is used as a host cell, the recombinant DNA capable of autonomous replication in a parent strain is preferably a recombinant DNA composed of a promoter, a ribosomal binding sequence, the DNA, and a transcription termination sequence. A DNA that controls the promoter may be contained.

When the recombinant DNA capable of autonomous replication in a parent strain is used, examples of the expression vector and the promoter when the expression vector is used include the same expression vectors and promoters as described above.

When the recombinant DNA capable of autonomous replication in a parent strain is used, it is preferable to use a plasmid in which the distance between the Shine-Dalgarno sequence, which is a ribosomal binding sequence, and the initiation codon is adjusted to be an appropriate distance (for example, 6 to 18 nucleotides).

When the recombinant DNA capable of autonomous replication in a parent strain is used, a transcription termination sequence is not necessarily required, but it is preferable to place a transcription termination sequence right under the structural gene.

It may be confirmed that the microorganism obtained by the above method is a microorganism having an increased copy number of the DNA encoding a protein having aldehyde dehydrogenase activity compared to that of a parent strain, for example, by measuring the transcriptional level of the DNA in the microorganism by Northern blotting or the production level of the protein in the microorganism by Western blotting and comparing it with that of the parent strain.

Examples of such a microorganism include the strain W3110AE, which is described below in Examples.

(Microorganism Having Enhanced Activity of L-Alanine Dehydrogenase (Ald))

L-alanine dehydrogenase refers to a protein having a L-alanine dehydrogenase activity. The L-alanine dehydrogenase activity refers to an activity to produce L-alanine with pyruvic acid as a substrate.

Examples of the microorganism having enhanced L-alanine dehydrogenase activity compared to that of a parent strain include a microorganism that is obtained by transforming a microorganism of the parent strain with a recombinant DNA comprising a DNA encoding the protein and has an increased copy number of the DNA compared to that of the parent strain.

Examples of the microorganism that is obtained by transforming a microorganism of the parent strain with a recombinant DNA comprising a DNA encoding a protein having L-alanine dehydrogenase activity and has an increased copy number of the DNA compared to that of the parent strain, include a microorganism having an increased copy number of the DNA on chromosomal DNA and a microorganism having the DNA out of chromosomal DNA as a plasmid DNA resulted from transforming a microorganism of the parent strain with the recombinant DNA comprising the DNA encoding a protein having L-alanine dehydrogenase activity.

The protein having L-alanine dehydrogenase activity may be any protein as long as it is a protein having the activity, and examples thereof include proteins of any one of the following [30] to [32]:
[30] a protein having the amino acid sequence set forth in SEQ ID NO: 18,
[31] a mutant protein comprising an amino acid sequence modified from the amino acid sequence set forth in SEQ ID NO: 18 by deletion, substitution, insertion, or addition of 1 to 20, preferably 1 to 10, and most preferably 1 to 5 amino acids, and having L-alanine dehydrogenase activity,
[32] a homologous protein comprising an amino acid sequence having 95% or more, preferably 97% or more, more preferably 98% or more, and most preferably 99% or more identity with the amino acid sequence set forth in SEQ ID NO: 18, and having L-alanine dehydrogenase activity.

In the above description, a mutant protein comprising an amino acid sequence where 1 to 20, preferably 1 to 10, and most preferably 1 to 5 amino acid residues are deleted, substituted, inserted, or added and having L-alanine dehydrogenase activity may be obtained, for example, by introducing a mutation into DNA encoding a protein having the amino acid sequence set forth in SEQ ID NO: 18, using the above error-prone PCR or site-directed mutagenesis.

The deletion, substitution, insertion, or addition of 1 to 20, preferably 1 to 10, and most preferably 1 to 5 amino acids in the amino acid sequence set forth in SEQ ID NO: 18 may be deletion, substitution, insertion, or addition of one or more amino acid residues at any position(s) in the same sequence.

It may be confirmed that the above mutant protein or homologous protein is a protein having L-alanine dehydrogenase activity, for example, by producing a transformant expressing the protein to be confirmed on its activity using DNA recombination and culturing the transformant in a culture medium, and measuring the amount of alanine in the culture.

The DNA encoding a protein having L-alanine dehydrogenase activity may be any DNA as long as it is a DNA encoding a protein having the activity, and examples thereof include a DNA of any one of the following [33] to [36]:
[33] a DNA encoding a protein of any one of the above [30] to [32],
[34] a DNA having the nucleotide sequence set forth in SEQ ID NO: 17,
[35] a DNA that hybridizes with a DNA comprising a nucleotide sequence complementary to the nucleotide sequence set forth in SEQ ID NO: 17 under stringent conditions, and encodes a homologous protein having L-alanine dehydrogenase activity,
[36] a DNA comprising a nucleotide sequence having at least 95% or more, preferably 97% or more, more preferably 98% or more, and most preferably 99% or more identity with the nucleotide sequence set forth in SEQ ID NO: 17, and encoding a homologous protein having L-alanine dehydrogenase activity.

The description about hybridization and stringent conditions is the same as described above.

Examples of the above DNA that can hybridize under stringent conditions include a DNA having at least 95% or more, preferably 97% or more, more preferably 98% or more, and most preferably 99% or more identity with the DNA comprising the nucleotide sequence set forth in SEQ ID NO: 17, as calculated using BLAST, FASTA, or the like described above based on the above parameters or the like.

The DNA encoding a protein having L-alanine dehydrogenase activity may be obtained, for example, by the above method using Southern hybridization or PCR using a probe DNA that may be designed based on the nucleotide sequence set forth in SEQ ID NO: 17 and using, for example, genomic DNA of *Bacillus subtilis* strain 168 as a template.

The microorganism that is obtained by transforming a microorganism of the parent strain with a recombinant DNA comprising a DNA encoding a protein having L-alanine dehydrogenase activity and has an increased copy number of the gene encoding the protein compared to that of the parent strain, may be obtained by the same method as described above.

It may be confirmed that the microorganism obtained by the above method is a microorganism having an increased copy number of the DNA encoding a protein having L-alanine dehydrogenase activity compared to that of the parent strain, for example, by measuring the transcriptional level of the DNA in the microorganism by Northern blotting or the production level of the protein in the microorganism by Western blotting, and comparing it with that of the parent strain.

Examples of such a microorganism include the strain W3110A and strain W3110AE described below in Examples.

1-2. Microorganism Having Enhanced Ethylamine-Producing Activity and Glutaminase Activity and Method for Creating the Microorganism Microorganism Having Enhanced Ethylamine-Producing Activity Examples of the microorganism of the present invention include a microorganism producing acetaldehyde, alanine, and glutamine from a carbon source and having enhanced activity of a protein of any one of the above [1] to [3] and enhanced glutaminase activity compared to those of a parent strain, other than the microorganism in the above 1-1.

The microorganism having enhanced activity of a protein of any one of the above [1] to [3] compared to that of a parent strain and the method for creating the microorganism are the same as those in the above 1-1.

Microorganism Having Enhanced Glutaminase Activity

The microorganism of the present invention in 1-2 is a microorganism having enhanced activity of a protein of any one of the above [1] to [3] as well as enhanced glutaminase activity.

A glutaminase refers to a protein having glutaminase activity. The glutaminase activity refers to an activity to produce theanine with ethylamine and glutamine as substrates.

Examples of the glutaminase include a glutaminase that microorganisms belonging to the genus *Pseudomonas*, more specifically *Pseudomonas nitroreducens* strain IFO 12694 (Japanese Unexamined Patent Publication No. H11-225789), has.

Examples of the microorganism having enhanced glutaminase activity compared to that of a parent strain include a microorganism having enhanced glutaminase activity compared to that of the parent strain, obtained by transforming the parent strain with a recombinant DNA comprising a DNA encoding glutaminase.

Examples of the DNA encoding glutaminase include a DNA encoding glutaminase preferably from prokaryotes such as bacteria or from yeast, more preferably from prokaryotes, and particularly preferably from *Pseudomonas nitroreducens* strain IFO 12694 (Japanese Unexamined Patent Publication No. H11-225789).

The DNA encoding glutaminase may be obtained in accordance with the same method as that in the above 1-1.

The recombinant DNA having the DNA may be obtained in accordance with the same method as that in the above 1-1.

The microorganism having enhanced glutaminase activity compared to that of a parent strain, obtained by transforming the parent strain with the recombinant DNA, may be created in accordance with the same method as that in the above 1-1.

It may be confirmed that the microorganism created by the above method is a microorganism having enhanced glutaminase activity compared to that of a parent strain by comparing the transcriptional level of the DNA encoding glutaminase, the production level of the protein, or the specific activity of the protein with that of the parent strain.

Increase in the transcriptional level of the DNA encoding the protein, or the production level of the protein encoded by the DNA may be confirmed, for example, by a method involving measuring the transcriptional level of the DNA by Northern blotting or the production level of the protein by Western blotting and comparing it with that of the parent strain.

The specific activity of glutaminase may be confirmed, for example, by purifying the protein from a transformant obtained by transforming the parent strain with a DNA encoding the protein, providing the protein, ethylamine, and glutamine in an aqueous medium, and measuring the specific activity from the amounts of theanine produced and accumulated in the aqueous medium and the protein.

Moreover, the microorganism of the present invention in 1-2 preferably has decreased or eliminated theanine-degrading activity, in addition to having enhanced glutaminase activity, from the viewpoint of suppressing the degradation of theanine produced. Specific examples of such a microorganism include a microorganism having decreased or eliminated activity of γ-glutamyltranspeptidase.

Microorganism Producing Acetaldehyde, Alanine, and Glutamine from Carbon Source

The microorganism of the present invention in 1-2 is a microorganism producing acetaldehyde, alanine, and glutamine from a carbon source and having enhanced activity of a protein of any one of the above [1] to [3] and enhanced glutaminase activity compared to those of a parent strain.

The microorganism producing acetaldehyde, alanine, and glutamine from a carbon source refers to a microorganism producing acetaldehyde, alanine, and glutamine from a carbon source as a starting material in the microorganism when the microorganism is cultured in a culture medium by a method in 2-1 described below.

Such a microorganism is not limited as long as it is a microorganism producing acetaldehyde, alanine, and glutamine from a carbon source as a starting material.

Examples thereof include a microorganism having enhanced ethylamine-producing activity and glutaminase activity, obtained by using any parent strain. Moreover, examples thereof include the above microorganism having enhanced ethylamine-producing activity and glutaminase activity created from a microorganism of any one of the following (E) to (H) as a parent strain or a microorganism of any one of the following (E) to (H) created from the above microorganism having enhanced ethylamine-producing activity and glutaminase activity as a parent strain:

(E) a microorganism having decreased or eliminated activity of at least one or more proteins selected from the group consisting of alcohol dehydrogenase (AdhE) and aldehyde reductase (YqhD) compared to that of a parent strain,
(F) a microorganism having enhanced aldehyde dehydrogenase (EutE) activity compared to that of a parent strain,
(G) a microorganism having enhanced L-alanine dehydrogenase (Ald) activity compared to that of a parent strain,
(H) a microorganism having any combination of traits that the microorganisms in the above (E) to (G) have.

From the viewpoint of increasing supplies of acetaldehyde and alanine, it is preferable that the microorganism of the present invention in 1-2 have a trait of the above (F) or (G), preferably the traits of the above (F) and (G).

In addition to that, it is more preferable that the microorganism have the trait of the above (E) from the viewpoint of suppressing metabolism of acetaldehyde into ethanol.

The methods for creating the above microorganism (E) having decreased or eliminated activity of at least one or more proteins selected from the group consisting of alcohol dehydrogenase and aldehyde reductase compared to that of a parent strain, microorganism (F) having enhanced aldehyde dehydrogenase activity compared to that of a parent strain, microorganism (G) having enhanced L-alanine dehydrogenase activity compared to that of a parent strain, and microorganism (H) having any combination of traits that the microorganisms in the above (E) to (G) have are the same as those in the above 1-1.

2. Method for Producing Theanine of the Present Invention

The methods for producing theanine of the present invention are methods of the following 2-1 and 2-2.

2-1. Method for Producing Theanine by Fermentation

Examples of the method for producing theanine of the present invention include a method for producing theanine, comprising culturing a microorganism in the above 1-1 or the above 1-2 in a culture medium to produce and accumulate theanine in the culture, and collecting theanine from the culture.

The method for culturing microorganisms in the above 1-1 and the above 1-2 may be performed by a usual method used for culturing a microorganism.

As the culture medium for culturing the microorganism, either natural media or synthetic media may be used as long as it is a culture medium that comprises a carbon source, a nitrogen source, an inorganic salt, and the like that the microorganism may utilize and in which the culture of the microorganism may efficiently be performed.

The carbon source may be any carbon source that the microorganism can utilize, and sugar such as glucose, fructose, sucrose, syrup comprising these, starch, or starch hydrolysates; organic acids such as acetic acid or propionic acid; and alcohols such as glycerol, ethanol, or propanol, or the like may be used.

As the nitrogen source, an ammonium salt of an inorganic acid or an organic acid such as ammonia, ammonium chloride, ammonium sulfate, ammonium acetate, or ammonium phosphate; other nitrogen-containing compounds; peptone, meat extract, yeast extract, corn steep liquor, a casein hydrolysate, a soybean cake, a soybean cake hydrolysate, or various fermentative cells and digests thereof, or the like may be used.

As the inorganic salt, monopotassium phosphate, dipotassium hydrogenphosphate, magnesium phosphate, magnesium sulfate, sodium chloride, ferrous sulfate, manganese sulfate, copper sulfate, calcium carbonate, or the like may be used.

The culture may usually be performed under aerobic conditions, such as shaking culture, deep-aerated spinner culture, or the like. Culture temperature is usually 15 to 40° C. and culture time is usually 5 hours to 7 days. The pH of a culture liquid during culture is usually maintained between 3.0 and 9.0. The adjustment of pH may be performed using inorganic or organic acid, an alkaline solution, urea, calcium carbonate, ammonia, or the like.

Moreover, antibiotics such as ampicillin or tetracycline may be added to the culture medium as needed during the culture. When culturing a microorganism transformed with an expression vector with an inducible promoter as a promoter, an inducer may be added to the culture medium as needed. For example, isopropyl-β-D-thiogalactopyranoside (IPTG) or the like may be added to the culture medium when culturing a microorganism transformed with an expression vector with a lac promoter, and indoleacrylic acid or the like may be added to the culture medium when culturing a microorganism transformed with an expression vector with a trp promoter.

According to the the above culture, theanine may be manufactured by producing and accumulating theanine in the culture and collecting theanine from the culture.

The produced theanine may be derivatized with (9-fluorenylmethyl) chloroformate (manufactured by Tokyo Chemical Industry Co., Ltd. and hereinafter referred to as Fmoc) and analyzed by HPLC. The collection of the theanine produced in a reaction solution may be performed by a usual method using active carbon, ion exchange resin, or the like.

The collection of theanine from the culture may usually be carried out by combining ion exchange resin techniques, precipitation, and other known methods. When theanine accumulates in cells, theanine may be collected, for example, by an ion exchange resin technique or the like from supernatant obtained by homogenizing the cells by sonication or the like and removing the cells by centrifugation.

2-2. Method for Producing Theanine Using Acetaldehyde, Alanine, Glutamic Acid, and ATP or Acetaldehyde, Alanine, and Glutamine as Substrates Examples of the method for producing theanine of the present invention also include methods for producing theanine using acetaldehyde, alanine, glutamic acid, and ATP or acetaldehyde, alanine, and glutamine as substrates.

Specifically, by providing a protein of any one of the above [1] to [3] and γ-glutamylmethylamide synthetase together in an aqueous medium comprising acetaldehyde, alanine, glutamic acid, and ATP, theanine may be produced and accumulated in the aqueous medium and collected from the aqueous medium.

Moreover, by providing a protein of any one of the above [1] to [3] and glutaminase together in an aqueous medium comprising acetaldehyde, alanine, and glutamine, theanine may also be produced and accumulated in the aqueous medium and collected from the aqueous medium.

The concentrations of the protein of any one of the above [1] to [3], γ-glutamylmethylamide synthetase, and glutaminase in the aqueous medium used in the method for producing theanine of the present invention are usually 0.001 to 500 g/L and preferably 0.01 to 300 g/L each.

The concentrations of acetaldehyde, alanine, glutamic acid, ATP, and glutamine in the aqueous medium are usually 0.1 mM to 10 M and preferably 1 mM to 1 M each.

Examples of the aqueous medium include water; buffer solutions such as phosphate, carbonate, acetate, borate, citrate, and tris; alcohols such as methanol and ethanol; esters such as ethyl acetate; ketones such as acetone; and amides such as acetamide. Moreover, the culture liquid of the microorganism used as the enzyme source described below may also be used as an aqueous medium.

Chelating agents such as phytic acid, a surfactant, or an organic solvent may be added in the reaction of producing theanine, as needed.

The surfactant may be any surfactant, such as non-ionic surfactants such as octadecylamine polyoxyethylene (for example, NYMEEN S-215, manufactured by Nippon Oil and Fats Company, Limited); cationic surfactants such as cetyltrimethylammonium bromide or alkyldimethyl benzyl ammonium chloride (for example, Cation F2-40E, manufactured by Nippon Oil and Fats Company, Limited); anion surfactants such as lauroyl sarcosinate; tertiary amines such as alkyldimethylamine (for example, Tertiary Amine FB, manufactured by Nippon Oil and Fats Company, Limited), as long as it promotes the production of theanine and may be used alone or as a mixture of several surfactants. The surfactant may usually be used at a concentration of 0.1 to 50 g/L.

Examples of the organic solvent include xylene, toluene, aliphatic alcohol, acetone, and ethyl acetate, and the organic solvent may usually be used at a concentration of 0.1 to 50 ml/L.

The reaction of producing theanine may be performed in an aqueous medium for 1 to 96 hours usually under conditions of pH 5 to 10, preferably pH 6 to 8, and 20 to 50° C. To promote the reaction of production, adenine, adenosine-5'-monophosphate (AMP), ADP, ATP, magnesium sulfate, magnesium chloride, or the like may be added. Adenine and AMP may usually be used at concentrations of 0.01 to 100 mmol/L.

As the protein of any one of the above [1] to [3], γ-glutamylmethylamide synthetase, and glutaminase, for example, those purified from the culture of the microorganism in the above 1-1 or the microorganism in the above 1-2 may be used.

The acetaldehyde, alanine, glutamic acid, ATP, and glutamine used as substrates are not particularly limited and, for example, commercially available acetaldehyde, alanine, glutamic acid, ATP, and glutamine may be used.

Moreover, the acetaldehyde, alanine, glutamic acid, ATP, and glutamine obtained by using the culture of any one or more microorganisms of the microorganisms in the above 1-1 and the above 1-2 or a processed product of the culture as an enzyme source and providing the enzyme source and an energy donor in an aqueous medium to produce and accumulate them in the microorganism cells or the aqueous medium may be used.

Examples of the energy donor include the carbon source in the above 2-1.

Moreover, acetaldehyde, alanine, glutamic acid, ATP, and glutamine obtained by using a culture of any microorganism that produces and accumulates a substance selected from the group consisting of acetaldehyde, alanine, glutamic acid, ATP, and glutamine or a processed product of the culture as an enzyme source and providing the enzyme source and an energy donor in an aqueous medium to produce and accumulate them in the microorganism cells or the aqueous medium may be used.

Method for Producing Theanine Using Culture of Microorganism Having Enhanced Ethylamine-Producing Activity and γ-Glutamylmethylamide Synthetase Activity or Glutaminase Activity or a Processed Product of the Culture Moreover, cultures of the microorganisms in the above 1-1 and the above 1-2 or processed products of the cultures may also be used as an enzyme source instead of the purified protein of any one of the above [1] to [3], γ-glutamylmethylamide synthetase, and glutaminase.

The method of culturing the microorganism and the culture medium for culturing the microorganism are the same as those in the above 2-1.

Theanine may be produced by using a culture of the microorganism obtained by the above culture or a processed product of the culture as an enzyme source, providing the enzyme source, acetaldehyde, alanine, glutamic acid, and ATP, or acetaldehyde, alanine, and glutamine in an aqueous medium to produce and accumulate theanine in the aqueous medium, and collecting theanine from the medium.

Examples of the processed product of the culture include a condensate of the above culture, a dried product of the culture, cells obtained by centrifugation, filtration, or the like of the culture, a dried product of the cells, a freeze-dried product of the cells, a product of the cells processed with a surfactant, a product of the cells processed with a solvent, a product of the cells processed with an enzyme, and a product comprising living cells maintaining the same function as the culture as an enzyme source such as a fixed product of the cells, and a product of the cells processed with sonication, a product of the cells processed with mechanical attrition, a crude enzyme extract obtained from the processed cells, and a purified enzyme obtained from the processed cells; preferably a condensate of the above culture, a dried product of the culture, or cells obtained by centrifugation, filtration, or the like of the culture, a dried product of the cells, a freeze-dried product of the cells, a product of the cells processed with a surfactant, a product of the cells processed with a solvent, a product of the cells processed with an enzyme, and a product comprising living cells maintaining the same function as the culture as an enzyme source such as a fixed product of the cells, and a product of the cells processed with sonication, a product of the cells processed with mechanical attrition; more preferably a condensate of the above culture, a dried product of the culture, cells obtained by centrifugation, filtration, or the like of the culture, a dried product of the cells, a freeze-dried product of the cells, a product of the cells processed with a surfactant, a product of the cells processed with a solvent, a product of the cells processed with an enzyme, and a product comprising living cells maintaining the same function as the culture as an enzyme source such as a fixed product of the cells.

The analysis and the collection of produced theanine are the same as those in the above 2-1.

Preferred embodiments of the present invention include the following.

(I) A microorganism producing acetaldehyde, alanine, glutamic acid, and ATP from a sugar, and having enhanced activity of a protein of any one of the following [1] to [3] and enhanced γ-glutamylmethylamide synthetase activity compared to those of a parent strain, the microorganism belonging to the genus *Escherichia*:

[1] a protein comprising an amino acid sequence set forth in SEQ ID NO: 2, 4, 6, or 8;

[2] a mutant protein comprising an amino acid sequence modified from an amino acid sequence set forth in SEQ ID NO: 2, 4, 6, or 8 by deletion, substitution, insertion, or addition of 1 to 20 amino acids, and having activity to produce ethylamine with acetaldehyde and alanine as substrates (hereinafter, referred to as ethylamine-producing activity); and

[3] a homologous protein comprising an amino acid sequence having 95% or more identity with an amino acid sequence set forth in SEQ ID NO: 2, 4, 6, or 8, and having ethylamine-producing activity.

(II) The microorganism of the above (I), the microorganism having enhanced L-alanine dehydrogenase activity and decreased or eliminated aldehyde reductase activity compared to those of the parent strain.

(III) The microorganism of the above (I) or (II), the microorganism having enhanced aldehyde dehydrogenase activity and decreased or eliminated alcohol dehydrogenase activity compared to those of the parent strain.

(IV) The microorganism of the above (I), the microorganism having enhanced aldehyde dehydrogenase activity and/or L-alanine dehydrogenase activity compared to that of the parent strain.

(V) The microorganism of the above (IV), the microorganism having decreased or eliminated alcohol dehydrogenase activity and/or aldehyde reductase activity compared to that of the parent strain.

(VI) A method for producing theanine, comprising: culturing a microorganism of any of the above (I) to (V) in a culture medium to produce and accumulate theanine in a culture; and collecting theanine from the culture.

(VII) A method for producing theanine, comprising: providing a culture of the microorganism of any of the above (I) to (V) or a processed product of the culture, acetaldehyde, alanine, glutamic acid, and ATP together in an aqueous medium to produce and accumulate theanine in the aqueous medium; and collecting theanine from the aqueous medium.

(VIII) A microorganism producing acetaldehyde, alanine, and glutamine from a sugar, having enhanced activity of a protein of any one of the [1] to [3] in the above (I) and enhanced glutaminase activity compared to those of a parent strain, and the microorganism belonging to the genus *Escherichia*.

(IX) The microorganism of the above (VIII), the microorganism having enhanced L-alanine dehydrogenase activity and decreased or eliminated aldehyde reductase activity compared to those of the parent strain.

(X) The microorganism of the above (VIII) or (IX), the microorganism having enhanced aldehyde dehydrogenase activity and decreased or eliminated alcohol dehydrogenase activity compared to those of the parent strain.

(XI) The microorganism of the above (VIII), the microorganism having enhanced aldehyde dehydrogenase activity and/or L-alanine dehydrogenase activity compared to that of the parent strain.

(XII) The microorganism of the above (XI), the microorganism having decreased or eliminated alcohol dehydrogenase activity and/or aldehyde reductase activity compared to that of the parent strain.

(XIII) A method for producing theanine, comprising: culturing a microorganism of any of the above (VIII) to (XII) in a culture medium to produce and accumulate theanine in a culture; and collecting theanine from the culture.

(XIV) A method for producing theanine, comprising: providing a culture of a microorganism of any of the above (VIII) to (XII) or a processed product of the culture, acetaldehyde, alanine, and glutamine together in an aqueous medium to produce and accumulate theanine in the aqueous medium; and collecting theanine from the aqueous medium.

Examples of the present invention will be described below, but the present invention is not limited to these Examples.

EXAMPLE

Example 1

Production of Theanine Using Acetaldehyde, Alanine, Glutamic Acid, and ATP as Substrates (1) Creation of Microorganism Having Enhanced Ethylamine-Producing Activity and γ-Glutamylmethylamide Synthetase Activity Pseudomonas syringae pv. Syringae strain B728a was cultured by a well-known method of culturing, and chromosomal DNA of the microorganism was isolated and purified. PCR was performed using the oligonucleotides comprising the nucleotide sequences set forth in SEQ ID NOs: 19 and 20 as a primer set and the chromosomal DNA as a template to amplify the DNA fragment encoding γ-glutamylmethylamide synthetase Psyr_2273 (protein comprising the amino acid sequence set forth in SEQ ID NO: 10).

Similarly, chromosomal DNA was isolated and purified from Pseudomonas putida strain KT2440 by the same method as that described above. PCR was performed using the oligonucleotides comprising the nucleotide sequences set forth in SEQ ID NOs: 21 and 22 as a primer set and the chromosomal DNA as a template to amplify a DNA fragment encoding the protein PP_5182 (the protein comprising, the amino acid sequence set forth in SEQ ID NO: 2) having ethylamine-producing activity. Moreover, PCR was performed using the oligonucleotides comprising the nucleotide sequences set forth in SEQ ID NOs: 23 and 24 as a primer set and the chromosomal DNA as a template to amplify a DNA fragment encoding the protein PP_0596 (the protein comprising the amino acid sequence set forth in SEQ ID NO: 4) having ethylamine-producing activity.

Similarly, chromosomal DNA was isolated and purified from Pseudomonas chlororaphis by the same method as that described above. PCR was performed using the oligonucleotides comprising the nucleotide sequences set forth in SEQ ID NOs: 25 and 26 as a primer set and the chromosomal DNA as a template to amplify a DNA fragment encoding the protein JM49_01725 (the protein comprising the amino acid sequence set forth in SEQ ID NO: 6) having ethylamine-producing activity.

Similarly, chromosomal DNA was isolated and purified from Pseudomonas fluorescens strain SBW25 by the same method as that described above. PCR was performed using the oligonucleotides comprising the nucleotide sequences set forth in SEQ ID NOs: 27 and 28 as a primer set and the chromosomal DNA as a template to amplify a DNA fragment encoding the protein PFLU_RS03325 (the protein comprising the amino acid sequence set forth in SEQ ID NO: 8) having ethylamine-producing activity.

The DNA fragments encoding Psyr_2273 and PP_5182 obtained in the above were ligated to the expression vector pTrc99A (manufactured by GE Healthcare Bioscience Holding Limited) using In-Fusion HD Cloning Kit (manufactured by Takara Bio Inc.) to obtain an expression plasmid pTrc99A_Psyr_2273_PP_5182.

Similarly, the DNA fragments encoding Psyr_2273 and PP_0596 obtained in the above were ligated to the expression vector pTrc99A (manufactured by GE Healthcare Bioscience Holding Limited) using In-Fusion HD Cloning Kit (manufactured by Takara Bio Inc.) to obtain an expression plasmid pTrc99A_Psyr_2273_PP_0596.

Similarly, the DNA fragments encoding Psyr_2273 and JM49_01725 obtained in the above were ligated to the expression vector pTrc99A (manufactured by GE Healthcare Bioscience Holding Limited) using In-Fusion HD Cloning Kit (manufactured by Takara Bio Inc.) to obtain an expression plasmid pTrc99A_Psyr_2273_JM49_01725.

Similarly, the DNA fragments encoding Psyr_2273 and PFLU_RS03325 obtained in the above were ligated to the expression vector pTrc99A (manufactured by GE Healthcare Bioscience Holding Limited) using In-Fusion HD Cloning Kit (manufactured by Takara Bio Inc.) to obtain an expression plasmid pTrc99A_Psyr_2273_PFLU_RS03325.

Escherichia coli strain W3110 was transformed with the obtained pTrc99A_Psyr_2273_PP_5182, pTrc99A_Psyr_2273_PP_0596, pTrc99A_Psyr_2273_JM49_01725, pTrc99A_Psyr_2273_PFLU_RS03325, or pTrc99A to obtain the strain W3110/pTrc99A_Psyr_2273_PP_5182, the strain W3110/pTrc99A_Psyr_2273_PP_0596, the strain W3110/pTrc99A_Psyr_2273_JM49_01725, the strain W3110/pTrc99A_Psyr_2273_PFLU_RS03325, and the strain W3110/pTrc99A, respectively, as recombinant Escherichia coli carrying those expression plasmids.

(2) Production of Theanine Using Acetaldehyde, Alanine, Glutamic Acid, and ATP as Substrates The strain W3110/pTrc99A_Psyr_2273_PP_5182, the strain W3110/pTrc99A_Psyr_2273_PP_0596, the strain W3110/pTrc99A_Psyr_2273_JM49_01725, the strain W3110/pTrc99A_Psyr_2273_PFLU_RS03325, and the strain W3110/pTrc99A obtained in Example 1 (1) were each cultured at 30° C. on LB plates overnight, and 5 mL of LB culture medium containing 100 mg/L ampicillin in a large test tube was inoculated with the strains and cultured with shaking at 30° C. for 12 hours.

Subsequently, with 0.05 mL of the culture, 5 mL each of the in vitro production culture medium [30 g/L glucose, 2 g/L magnesium sulfate heptahydrate, 5 g/L casamino acid, 2 g/L ammonium sulfate, 1 g/L citric acid, 14 g/L potassium dihydrogenphosphate, 16 g/L dipotassium hydrogenphosphate, 10 mg/L thiamine hydrochloride, 50 mg/L ferrous sulfate heptahydrate, 10 mg/L manganese sulfate pentahydrate (ingredients other than glucose and magnesium sulfate heptahydrate were autoclaved after adjustment of pH to 7.2 with an aqueous solution of sodium hydroxide, and glucose and magnesium sulfate heptahydrate were autoclaved after separate preparation of aqueous solutions containing glucose and magnesium sulfate heptahydrate and mixed after cooling thereof)] in a large test tube was inoculated and cultured at 30° C. for 5 hours, to which IPTG at a final concentration of 1 mM, alanine at a final concentration of 10 mM, and acetaldehyde at a final concentration of 10 mM were then added. The resulting mixture was further cultured with shaking at 30° C. for 21 hours.

After the completion of the culture, cells were removed by centrifugation of the culture liquid, and theanine contained in the supernatant was derivatized with Fmoc (manufactured by Tokyo Chemical Industry Co., Ltd.) and analyzed by HPLC. The result is shown in Table 1.

TABLE 1

| Strain | Theanine [g/L] |
|---|---|
| W3110/pTrc99A | Not detected |
| W3110/pTrc99A_Psyr_2273_PP_5182 | 0.11 |
| W3110/pTrc99A_Psyr_2273_PP_0596 | 0.06 |
| W3110/pTrc99A_Psyr_2273_JM49_01725 | 0.12 |
| W3110/pTrc99A_Psyr_2273_PFLU_RS03325 | 0.04 |

As the result, while the strain W3110/pTrc99A did not produce theanine, the strain W3110/pTrc99A_Psyr_2273_PP_5182, the strain W3110/pTrc99A_Psyr_2273_PP_0596, the strain W3110/pTrc99A_Psyr_2273_JM49_01725, and the strain W3110/pTrc99A_Psyr_2273_PFLU_RS03325 produced theanine.

From the foregoing, it has been found that theanine can be produced without exogenously adding ethylamine, using the microorganisms having enhanced ethylamine-producing activity and γ-glutamylmethylamide synthetase activity compared to those of the strain W3110, obtained by transforming the strain W3110 with a recombinant DNA having DNAs encoding a protein having ethylamine-producing activity (PP_5182, PP_0596, JM49_01725, or PFLU_RS03325) and γ-glutamylmethylamide synthetase (Psyr_2273).

Example 2

Creation of Microorganism to be Used in Production of Theanine by Fermentation (1) Acquisition of DNA Fragment to be Used as Marker in Gene Deletion and Gene Replacement PCR was performed using DNAs comprising nucleotide sequences indicated as "Primer set" in Table 2 as a primer set and a DNA indicated as "Template" in Table 2 as a template to amplify each DNA fragment.

TABLE 2

| Primer set (SEQ ID NO) | Template | Amplified DNA fragment |
| --- | --- | --- |
| 29 and 30 | pHSG396 (manufactured by Takara Bio Inc.) | Cat |
| 31 and 32 | Genomic DNA of *Bacillus subtilis* strain 168 | sacB |

Genomic DNA of *Bacillus subtilis* strain 168 was prepared by a routine method. The amplified DNA fragment cat contains from about 200 bp upstream to about 100 bp downstream of the cat gene. The amplified DNA fragment sacB contains from about 300 bp upstream to about 100 bp downstream of the sacB gene. The SalI recognition site is provided to DNAs comprising the nucleotide sequences set forth in SEQ ID NOs: 30 and 31.

The amplified DNA fragments cat and sacB were cut with the restriction enzyme SalI and ligated using DNA ligation Kit Ver.2 (manufactured by Takara Bio Inc.). PCR was performed using the ligation reaction solution as a template and the DNAs comprising the nucleotide sequences set forth in SEQ ID NOs: 29 and 32 as a primer set to obtain a DNA fragment containing the cat gene and the sacB gene (hereinafter, referred to as cat-sacB).

(2) Creation of Microorganism Having Enhanced L-Alanine Dehydrogenase Activity and Eliminated Aldehyde Reductase Activity

*Escherichia coli* in which the DNA encoding aldehyde reductase (hereinafter, referred to as yqhD gene) is replaced with a DNA encoding L-alanine dehydrogenase derived from *Bacillus subtilis* (hereinafter, referred to as ald gene) having a promoter that controls the expression of the ilvGMEDA operon (hereinafter, referred to as ilv promoter) added to upstream thereof, was created by the following method.

PCR using DNAs comprising nucleotide sequences indicated as "Primer set" in Table 3 as primer sets was performed with genomic DNA of *Bacillus subtilis* strain 168 as a template to amplify the ald gene, and with genomic DNA of *Escherichia coli* strain W3110 as a template to amplify other DNA fragments.

TABLE 3

| Primer set (SEQ ID NO) | Amplified DNA fragment | Note |
| --- | --- | --- |
| 33 and 34 | ilv promoter | |
| 35 and 36 | Upstream 1 of yqhD | 5' terminal sequences of nucleotide sequences set forth in SEQ ID NOs: 36 and 29 are complementary |
| 37 and 38 | Downstream 1 of yqhD | 5' terminal sequences of nucleotide sequences set forth in SEQ ID NOs: 37 and 32 are complementary |
| 35 and 39 | Upstream 2 of yqhD | 5' terminal sequences of nucleotide sequences set forth in SEQ ID NOs: 39 and 33 are complementary |
| 40 and 41 | ald | 5' terminal sequences of nucleotide sequences set forth in SEQ ID NOs: 40 and 34 are complementary |
| 42 and 38 | Downstream 2 of yqhD | 5' terminal sequences of nucleotide sequences set forth in SEQ ID NOs: 42 and 41 are complementary |

Upstream 1 of yqhD and Upstream 2 of yqhD contain from the initiation codon to about 1500 bp upstream thereof in the yqhD gene. Downstream 1 of yqhD and Downstream 2 of yqhD contain from the stop codon to about 1500 bp downstream thereof in the yqhD gene.

PCR was performed using a mixture of the fragment Upstream 1 of yqhD, the fragment Downstream 1 of yqhD, and cat-sacB fragment at the equimolar ratio as a template, and the DNAs comprising the nucleotide sequences set forth in SEQ ID NOs: 35 and 38 as a primer set, to obtain a DNA fragment containing yqhD gene flanking regions having the cat-sacB fragment inserted therebetween (hereinafter, referred to as yqhD::cat-sacB).

PCR was performed using a mixture of the fragment Upstream 2 of yqhD, the fragment Downstream 2 of yqhD, the ilv promoter fragment, and the ald fragment at the equimolar ratio as a template, and the DNAs comprising the nucleotide sequences set forth in SEQ ID NOs: 35 and 38 as a primer set, to obtain a DNA fragment containing yqhD gene flanking regions having the ald gene having the ilv promoter added to upstream thereof inserted therebetween (hereinafter, referred to as yqhD::Pilv-ald).

The yqhD::cat-sacB fragment was introduced into *Escherichia coli* strain W3110 carrying pKD46, a plasmid containing a gene encoding λ recombinase [Datsenko, K. A., Warner, B. L., Proc. Natl. Acad. Sci., USA, Vol. 97, 6640-6645 (2000)], by electroporation to obtain a transformant that exhibits chloramphenicol resistance and sucrose sensitivity. (a transformant in which the yqhD gene has been replaced with yqhD::cat-sacB).

The yqhD::Pilv-ald fragment was introduced into the transformant by electroporation to obtain a transformant that exhibits chloramphenicol sensitivity and sucrose resistance (a transformant in which the yqhD::cat-sacB has been replaced with Pilv-ald). Furthermore, a transformant from which pKD46 has been eliminated was obtained. The microorganism was named the strain W3110A.

(3) Creation of Microorganism Having Enhanced Aldehyde Dehydrogenase Activity and Eliminated Alcohol Dehydrogenase Activity

*Escherichia coli* in which a DNA encoding alcohol dehydrogenase (hereinafter, referred to as adhE gene) has been replaced with a gene encoding aldehyde dehydrogenase (hereinafter, referred to as eutE gene) having the ilv promoter added to upstream thereof, was created by the following method.

PCR was performed using genomic DNA of *Escherichia coli* strain W3110 prepared by a conventional method as a template and DNAs comprising nucleotide sequences indicated as "Primer set" in Table 4 as a primer set to amplify each DNA fragment.

TABLE 4

| Primer set (SEQ ID NO) | Amplified DNA fragment | Note |
| --- | --- | --- |
| 33 and 34 | ilv promoter | |
| 43 and 44 | Upstream 1 of adhE | 5' terminal sequences of nucleotide sequences set forth in SEQ ID NOs: 44 and 29 are complementary |
| 45 and 46 | Downstream 1 of adhE | 5' terminal sequences of nucleotide sequences set forth in SEQ ID NOs: 45 and 32 are complementary |
| 43 and 47 | Upstream 2 of adhE | 5' terminal sequences of nucleotide sequences set forth in SEQ ID NOs: 47 and 33 are complementary |
| 48 and 49 | eutE | 5' terminal sequences of nucleotide sequences set forth in SEQ ID NOs: 48 and 34 are complementary |
| 50 and 46 | Downstream 2 of adhE | 5' terminal sequences of nucleotide sequences set forth in SEQ ID NOs: 50 and 49 are complementary |

Upstream 1 of adhE and Upstream 2 of adhE contain from the initiation codon to about 1000 bp upstream thereof in the adhE gene. Downstream 1 of adhE and Downstream 2 of adhE contain from the stop codon to about 1500 bp downstream thereof in the adhE gene.

PCR was performed using a mixture of the fragment Upstream 1 of adhE, the fragment Downstream 1 of adhE, and cat-sacB fragment at the equimolar ratio as a template, and the DNAs comprising the nucleotide sequences set forth in SEQ ID NOs: 43 and 46 as a primer set, to obtain a DNA fragment containing adhE gene flanking regions having the cat-sacB fragment inserted therebetween (hereinafter, referred to as adhE::cat-sacB).

PCR was performed using a mixture of the fragment Upstream 2 of adhE, the fragment Downstream 2 of adhE, the ilv promoter fragment, the eutE fragment at the equimolar ratio as a template, and the DNAs comprising the nucleotide sequences set forth in SEQ ID NOs: 43 and 46 as a primer set, to obtain a DNA fragment containing the adhE gene flanking regions having the eutE gene having the ilv promoter added to upstream thereof inserted therebetween (hereinafter, referred to as adhE::Pilv-eutE).

The adhE::cat-sacB fragment was introduced into *Escherichia coli* strain W3110A carrying pKD46, a plasmid containing a gene encoding λ recombinase, by electroporation to obtain a transformant that exhibits chloramphenicol resistance and sucrose sensitivity (a transformant in which the adhE gene has been replaced with adhE::cat-sacB).

The adhE::Pilv-eutE fragment was introduced into the transformant by electroporation to obtain a transformant that exhibits chloramphenicol sensitivity and sucrose resistance (a transformant in which the adhE::cat-sacB has been replaced with Pilv-eutE). Furthermore, a transformant from which pKD46 has been eliminated was obtained. The microorganism was named the strain W3110AE.

Example 3

Production of Theanine from Glucose by Fermentation-1

The strain W3110AE obtained in Example 2 was transformed with pTrc99A_Psyr_2273_PP_5182, pTrc99A_Psyr_2273_PP_0596, pTrc99A_Psyr_2273_JM49_01725, pTrc99A_Psyr_2273_PFLU_RS03325, or pTrc99A described in Example 1 to obtain the strain W3110AE/pTrc99A_Psyr_2273_PP_5182, the strain W3110AE/pTrc99A_Psyr_2273_PP_0596, the strain W3110AE/pTrc99A_Psyr_2273_JM49_01725, the strain W3110AE/pTrc99A_Psyr_2273_PFLU_RS03325, and the strain W3110AE/pTrc99A, respectively.

The microorganisms were each cultured at 30° C. on LB plates overnight and 5 mL of LB culture medium containing 100 mg/L ampicillin in a large test tube was inoculated with the strains and cultured with shaking at 30° C. for 12 hours.

Subsequently, with 0.05 mL of the culture, 5 mL each of the in vitro production culture medium [30 g/L glucose, 2 g/L magnesium sulfate heptahydrate, 5 g/L casamino acid, 2 g/L ammonium sulfate, 1 g/L citric acid, 14 g/L potassium dihydrogenphosphate, 16 g/L dipotassium hydrogenphosphate, 10 mg/L thiamine hydrochloride, 50 mg/L ferrous sulfate heptahydrate, 10 mg/L manganese sulfate pentahydrate (ingredients other than glucose and magnesium sulfate heptahydrate were autoclaved after adjustment of pH to 7.2 with an aqueous solution of sodium hydroxide, and glucose and magnesium sulfate heptahydrate were autoclaved after separate preparation of aqueous solutions containing glucose and magnesium sulfate heptahydrate and mixed after cooling thereof)] in a large test tube was inoculated and cultured at 30° C. for 5 hours, to which IPTG at a final concentration of 1 mM was then added. The resulting mixture was further cultured with shaking at 30° C. for 21 hours.

After the completion of the culture, cells were removed by centrifugation of the culture liquid, and theanine contained in the supernatant was derivatized with Fmoc (manufactured by Tokyo Chemical Industry Co., Ltd.) and analyzed by HPLC. The result is shown in Table 5.

TABLE 5

| Strain | Theanine [g/L] |
| --- | --- |
| W3110AE/pTrc99A | Not detected |
| W3110AE/pTrc99A_Psyr_2273_PP_5182 | 1.48 |
| W3110AE/pTrc99A_Psyr_2273_PP_0596 | 1.29 |
| W3110AE/pTrc99A_Psyr_2773_JM49_01725 | 1.12 |
| W3110AE/pTrc99A_Psyr_2273_PFLU_RS03325 | 1.00 |

As the result, while the strain W3110AE/pTrc99A did not produce theanine, the strain W3110AE/pTrc99A_Psyr_2273_PP_5182, the strain W3110AE/pTrc99A_Psyr_2273_PP_0596, the strain W3110AE/pTrc99A_Psyr_2273_JM49_01725, and the strain W3110AE/pTrc99A_Psyr_2273_PFLU_RS03325 produced theanine.

From the foregoing, it has been found that theanine can efficiently be produced from sugar by using the microorganisms having enhanced ethylamine-producing activity and γ-glutamylmethylamide synthetase activity compared to those of the strain W3110AE, obtained by transforming the strain W3110AE with a recombinant DNA having DNAs encoding a protein having ethylamine-producing activity (PP_5182, PP_0596, JM49_01725, or PFLU_RS03325) and γ-glutamylmethylamide synthetase (Psyr_2273).

Moreover, no ethylamine was left in the culture medium at this time and it has been found that theanine can be produced by this method without exogenously adding ethylamine and without accumulation of ethylamine in a culture medium as a byproduct.

Example 4

Production of Theanine Using Acetaldehyde, Alanine, and Glutamine as Substrates (1) Creation of Microorganism Having Enhanced Ethylamine-Producing Activity and Glutaminase Activity

*Pseudomonas nitroreducens* strain IFO 12694 (Japanese Unexamined Patent Publication No. H11-225789) is cultured by a well-known method of culturing and chromosomal DNA of the microorganism is isolated and purified. Primers are designed based on the nucleotide sequence of the DNA encoding glutaminase in Japanese Unexamined Patent Publication No. H11-225789, and PCR is performed using chromosomal DNA as a template in accordance with the method of the above 1-2 to amplify a DNA fragment encoding glutaminase GLN.

The DNA fragments encoding GLN and PP_5182 obtained in Example 1 (1) are ligated to the expression vector pTrc99A (manufactured by GE Healthcare Bioscience Holding Limited) using In-Fusion HD Cloning Kit (manufactured by Takara Bio Inc.) to obtain an expression plasmid pTrc99A_GLN_PP_5182.

Similarly, the DNA fragments encoding GLN and PP_0596 obtained in Example 1 (1) are ligated to the expression vector pTrc99A (manufactured by GE Healthcare Bioscience Holding Limited) using In-Fusion HD Cloning Kit (manufactured by Takara Bio Inc.) to obtain an expression plasmid pTrc99A_GLN_PP_0596.

Similarly, the DNA fragments encoding GLN and JM49_01725 obtained in Example 1 (1) are ligated to the expression vector pTrc99A (manufactured by GE Healthcare Bioscience Holding Limited) using In-Fusion HD Cloning Kit (manufactured by Takara Bio Inc.) to obtain an expression plasmid pTrc99A_GLN_JM49_01725.

Similarly, the DNA fragments encoding GLN and PFLU_RS03325 obtained in Example 1 (1) are ligated to the expression vector pTrc99A (manufactured by GE Healthcare Bioscience Holding Limited) using In-Fusion HD Cloning Kit (manufactured by Takara Bio Inc.) to obtain an expression plasmid pTrc99A_GLN_PFLU_RS03325.

*Escherichia coli* strain W3110 are transformed with pTrc99A_GLN_PP_5182, pTrc99A_GLN_PP_0596, pTrc99A_GLN_JM49_01725, pTrc99A_GLN_PFLU_RS03325, or pTrc99A to obtain the strain W3110/pTrc99A_GLN_PP_5182, the strain W3110/pTrc99A_GLN_PP_0596, the strain W3110/pTrc99A_GLN_JM49_01725, the strain W3110/pTrc99A_GLN_PFLU_RS03325, and the strain W3110/pTrc99A, respectively, as recombinant *Escherichia coli* carrying those expression plasmids.

(2) Production of Theanine Using Acetaldehyde, Alanine, and Glutamine as Substrates The strain W3110/pTrc99A_GLN_PP_5182, the strain W3110/pTrc99A_GLN_PP_0596, the strain W3110/pTrc99A_GLN_JM49_01725, the strain W3110/pTrc99A_GLN_PFLU_RS03325, and the strain W3110/pTrc99A are each cultured at 30° C. on LB plates overnight and 5 mL of LB culture medium containing 100 mg/L ampicillin in a large test tube is inoculated with the strains, and cultured with shaking at 30° C. for 12 hours.

Subsequently, with 0.05 mL of the culture, 5 mL each of the in vitro production culture medium [30 g/L glucose, 2 g/L magnesium sulfate heptahydrate, 5 g/L casamino acid, 2 g/L ammonium sulfate, 1 g/L citric acid, 14 g/L potassium dihydrogenphosphate, 16 g/L dipotassium hydrogenphosphate, 10 mg/L thiamine hydrochloride, 50 mg/L ferrous sulfate heptahydrate, 10 mg/L manganese sulfate pentahydrate (ingredients other than glucose and magnesium sulfate heptahydrate are autoclaved after adjustment of pH to 7.2 with an aqueous solution of sodium hydroxide, and glucose and magnesium sulfate heptahydrate are autoclaved after separate preparation of aqueous solutions containing glucose and magnesium sulfate heptahydrate and mixed after cooling thereof)] in a large test tube is inoculated and cultured at 30° C. for 5 hours, to which IPTG at a final concentration of 1 mM, alanine at a final concentration of 10 mM, and acetaldehyde at a final concentration of 10 mM are then added. The resulting mixture is further cultured with shaking at 30° C. for 21 hours.

After the completion of the culture, cells are removed by centrifugation of the culture liquid, and theanine contained in the supernatant is derivatized with Fmoc (manufactured by Tokyo Chemical Industry Co., Ltd.) and analyzed by HPLC.

As a result, it is found that theanine can be produced without exogenously adding ethylamine, using the microorganisms having enhanced ethylamine-producing activity and glutaminase activity compared to those of the strain W3110 obtained by transforming the strain W3110 with a recombinant DNA having DNAs encoding a protein having ethylamine-producing activity (PP_5182, PP_0596, JM49_01725, or PFLU_RS03325) and glutaminase GLN.

Example 5

Production of Theanine from Glucose by Fermentation-2

The strain W3110AE obtained in Example 2 is transformed with pTrc99A_GLN_PP_5182, pTrc99A_GLN_PP_0596, pTrc99A_GLN_JM49_01725, pTrc99A_GLN_PFLU_RS03325, or pTrc99A described in Example 4 to obtain the strain W3110AE/pTrc99A_GLN_PP_5182, the strain W3110AE/pTrc99A_GLN_PP_0596, the strain W3110AE/pTrc99A_GLN_JM49_01725, the strain W3110AE/pTrc99A_GLN_PFLU_RS03325, and the strain W3110AE/pTrc99A, respectively.

The microorganisms are each cultured at 30° C. on LB plates overnight and 5 mL of LB culture medium containing 100 mg/L ampicillin in a large test tube is inoculated with the strains, and cultured with shaking at 30° C. for 12 hours.

Subsequently, with 0.05 mL of the culture, 5 mL each of the in vitro production culture medium [30 g/L glucose, 2 g/L magnesium sulfate heptahydrate, 5 g/L casamino acid, 2 g/L ammonium sulfate, 1 g/L citric acid, 14 g/L potassium dihydrogenphosphate, 16 g/L dipotassium hydrogenphosphate, 10 mg/L thiamine hydrochloride, 50 mg/L ferrous sulfate heptahydrate, 10 mg/L manganese sulfate pentahydrate (ingredients other than glucose and magnesium sulfate heptahydrate are autoclaved after adjustment of pH to 7.2 with an aqueous solution of sodium hydroxide, and glucose and magnesium sulfate heptahydrate are autoclaved after separate preparation of aqueous solutions containing glucose and magnesium sulfate heptahydrate and mixed after cooling thereof)] in a large test tube is inoculated and cultured at 30° C. for 5 hours, to which IPTG at a final concentration of 1 mM is then added. The resulting mixture is further cultured with shaking at 30° C. for 21 hours.

After the completion of the culture, cells are removed by centrifugation of the culture liquid, and theanine contained in the supernatant is derivatized with Fmoc (manufactured by Tokyo Chemical Industry Co., Ltd.) and analyzed by HPLC.

As a result, it is found that theanine can efficiently be produced from sugar by using the microorganisms having enhanced ethylamine-producing activity and glutaminase activity compared to those of the strain W3110AE, obtained by transforming the strain W3110AE with a recombinant DNA having DNAs encoding a protein having ethylamine-producing activity (PP_5182, PP_0596, JM49_01725, or PFLU_RS03325) and glutaminase GLN.

Moreover, by confirming that no ethylamine is left in the culture medium at this time, it is found that theanine can be produced by this method without exogenously adding ethylamine and without accumulation of ethylamine in a culture medium as a byproduct.

INDUSTRIAL APPLICABILITY

The present invention provides a microorganism producing theanine and a method for efficiently producing theanine without exogenously adding ethylamine and without accumulation or leftover of ethylamine as a byproduct using the microorganism.

Sequence Listing Free Text
SEQ ID NO: 19—Description of artificial sequence: Synthetic DNA
SEQ ID NO: 20—Description of artificial sequence: Synthetic DNA
SEQ ID NO: 21—Description of artificial sequence: Synthetic DNA
SEQ ID NO: 22—Description of artificial sequence: Synthetic DNA
SEQ ID NO: 23—Description of artificial sequence: Synthetic DNA
SEQ ID NO: 24—Description of artificial sequence: Synthetic DNA
SEQ ID NO: 25—Description of artificial sequence: Synthetic DNA
SEQ ID NO: 26—Description of artificial sequence: Synthetic DNA
SEQ ID NO: 27—Description of artificial sequence: Synthetic DNA
SEQ ID NO: 28—Description of artificial sequence: Synthetic DNA
SEQ ID NO: 29—Description of artificial sequence: Synthetic DNA
SEQ ID NO: 30—Description of artificial sequence: Synthetic DNA
SEQ ID NO: 31—Description of artificial sequence: Synthetic DNA
SEQ ID NO: 32—Description of artificial sequence: Synthetic DNA
SEQ ID NO: 33—Description of artificial sequence: Synthetic DNA
SEQ ID NO: 34—Description of artificial sequence: Synthetic DNA
SEQ ID NO: 35—Description of artificial sequence: Synthetic DNA
SEQ ID NO: 36—Description of artificial sequence: Synthetic DNA
SEQ ID NO: 37—Description of artificial sequence: Synthetic DNA
SEQ ID NO: 38—Description of artificial sequence: Synthetic DNA
SEQ ID NO: 39—Description of artificial sequence: Synthetic DNA
SEQ ID NO: 40—Description of artificial sequence: Synthetic DNA
SEQ ID NO: 41—Description of artificial sequence: Synthetic DNA
SEQ ID NO: 42—Description of artificial sequence: Synthetic DNA
SEQ ID NO: 43—Description of artificial sequence: Synthetic DNA
SEQ ID NO: 44—Description of artificial sequence: Synthetic DNA
SEQ ID NO: 45—Description of artificial sequence: Synthetic DNA
SEQ ID NO: 46—Description of artificial sequence: Synthetic DNA
SEQ ID NO: 47—Description of artificial sequence: Synthetic DNA
SEQ ID NO: 48—Description of artificial sequence: Synthetic DNA
SEQ ID NO: 49—Description of artificial sequence: Synthetic DNA
SEQ ID NO: 50—Description of artificial sequence: Synthetic DNA

The invention claimed is:

1. A microorganism that has been transformed with:
   [1] a polynucleotide encoding a polypeptide (i) having ethylamine-producing activity to produce ethylamine with acetaldehyde and alanine as substrates and (ii) comprising (a) the amino acid sequence of SEQ ID NO: 2, 4, 6, or 8, (b) the amino acid sequence of SEQ ID NO: 2, 4, 6, or 8 in which no more than 1-20 amino acids have been deleted, substituted, inserted, or added, or (c) an amino acid sequence that has 95% or more sequence identity to the amino acid sequence of SEQ ID NO: 2, 4, 6, or 8, and
   [2] a polynucleotide encoding a γ-glutamylmethylamide synthetase,
   wherein the microorganism produces acetaldehyde, alanine, glutamic acid, and ATP from a carbon source, and
   wherein the microorganism produces theanine.

2. A method for producing theanine, comprising:
   culturing the microorganism according to claim 1 in a culture medium to produce and accumulate theanine in a culture; and
   collecting theanine from the culture.

3. A method for producing theanine, comprising:
   providing a culture comprising the microorganism according to claim 1, acetaldehyde, alanine, glutamic acid, and ATP together in an aqueous medium to produce and accumulate theanine in the aqueous medium; and
   collecting theanine from the aqueous medium.

4. The microorganism according to claim 1, wherein the microorganism is a microorganism belonging to the genus *Escherichia* or the genus *Corynebacterium*.

5. The method for producing theanine according to claim 2, wherein the microorganism is a microorganism belonging to the genus *Escherichia* or the genus *Corynebacterium*.

6. The microorganism according to claim 1, wherein the carbon source is sugar.

7. The method for producing theanine according to claim 3, wherein the microorganism is a microorganism belonging to the genus *Escherichia* or the genus *Corynebacterium*.

8. The microorganism of claim 1, wherein the polypeptide consists of the amino acid sequence of SEQ ID NO: 2, 4, 6, or 8.

9. The microorganism of claim 1, wherein the polypeptide consists of the amino acid sequence of SEQ ID NO: 2, 4, 6, or 8 in which no more than 1-20 amino acids have been deleted, substituted, inserted, or added.

10. The microorganism of claim 1, wherein the polypeptide consists of an amino acid sequence that has 95% or more sequence identity to the amino acid sequence of SEQ ID NO: 2, 4, 6, or 8.

* * * * *